United States Patent
Nyan

(10) Patent No.: US 10,072,309 B1
(45) Date of Patent: Sep. 11, 2018

(54) METHODS FOR REAL-TIME MULTIPLEX ISOTHERMAL DETECTION AND IDENTIFICATION OF BACTERIAL, VIRAL, AND PROTOZOAN NUCLEIC ACIDS

(71) Applicant: Dougbeh-Chris Nyan, Germantown, MD (US)

(72) Inventor: Dougbeh-Chris Nyan, Germantown, MD (US)

( * ) Notice: Subject to any disclaimer, the term of this patent is extended or adjusted under 35 U.S.C. 154(b) by 101 days.

(21) Appl. No.: 15/148,450

(22) Filed: May 6, 2016

Related U.S. Application Data

(60) Provisional application No. 62/158,664, filed on May 8, 2015.

(51) Int. Cl.
*C12Q 1/68* (2018.01)
*C12Q 1/70* (2006.01)

(52) U.S. Cl.
CPC ....... *C12Q 1/707* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

CN 102140538 A * 8/2011
CN 103060472 A * 4/2013
WO WO-2015160536 A1 * 10/2015 ............. C12Q 1/703

* cited by examiner

*Primary Examiner* — Aaron A Priest
(74) *Attorney, Agent, or Firm* — Daniel S. Polley, P.A.

(57) ABSTRACT

Herein disclosed are rapid real-time isothermal multiplex methods of detecting, identifying and quantifying bacterial, viral, and protozoan nucleic acids in a sample. These include contacting the sample with two or more sets of pathogen-specific reverse transcription loop-mediated isothermal amplification primers and novel oligofluorophores specific for the target bacterial, viral, and parasitic nucleic acids of interest such as human immunodeficiency virus, Ebola virus, Marburg virus, Yellow fever virus, hepatitis-B virus, Lassa fever virus, *Plasmodium*, hepatitis-C virus, hepatitis-E virus, dengue virus, Chikungunya virus, Japanese Encephalitis virus, Middle Eastern Respiratory Syndrome Corona virus, *Mycobacterium*, West Nile virus, Cytomegalovirus, Parvovirus, *Leishmania, Trypanosoma*, and Zika virus nucleic acids, under conditions sufficient to produce detectable real-time amplification signals in about 10 to 40 minutes. The amplification signals are produced by pathogen-specific fluorogenic labels included in one or more of the primers. Also, novel reaction and sample lysis buffers, primers, and kits for rapid multiplex detection, quantification, and identification of bacterial, viral, and protozoan nucleic acids by real-time isothermal amplification are herein disclosed.

15 Claims, 18 Drawing Sheets

Figure 1:
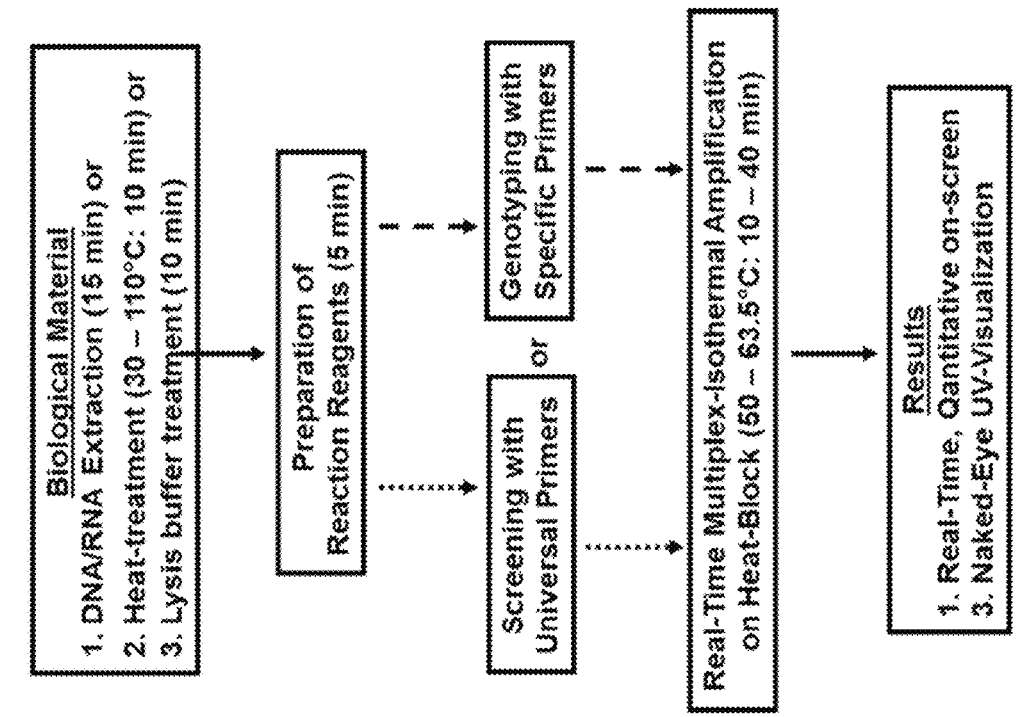

Specification includes a Sequence Listing.

SEQUENCE LISTING

```
<160> NUMBER OF SEQ ID NOS: 306

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide: N5F3

<400> SEQUENCE: 1
catagtggtc tgcggaacc                                                 19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide: N5R3

<400> SEQUENCE: 2
cacggtctac gagacctcc                                                 19

<210> SEQ ID NO 3
<211> LENGTH: 46
<212> TYPE: DNA
<213> ORGANISM: Artificial Sequence
<220> FEATURE:
<223> OTHER INFORMATION: Synthetic oligonucleotide: N5FIP

<400> SEQUENCE: 3
cgggcattga gcgggtttat cctttggtg agtacaccgg aattgc                    46

<210> SEQ ID NO 4
<211> LENGTH: 44
<212> TYPE: DNA
<213> ORGANISM: Artificial Sequence
<220> FEATURE:
<223> OTHER INFORMATION: Synthetic oligonucleotide: N5RIP

<400> SEQUENCE: 4
cgcgagactg ctagccgagt ttttagcacc ctatcaggca gtac                     44

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide: N5LF

<400> SEQUENCE: 5
aaaggacccg gtcatccc                                                  18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide: N5LR
```

<400> SEQUENCE: 6
gtcgcgaaag gccttgtg                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide: N6F3a

<400> SEQUENCE: 7
tagtggtctg cggaaccg                                                 18

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide: N6R3a

<400> SEQUENCE: 8
caccgtctac gagacctcc                                                19

<210> SEQ ID NO 9
<211> LENGTH: 45
<212> TYPE: DNA
<213> ORGANISM: Artificial Sequence
<220> FEATURE:
<223> OTHER INFORMATION: Synthetic oligonucleotide: N6FIPa

<400> SEQUENCE: 9
ggcattgagc gggtttgatc cattttgagt acaccggaat tgcca                   45

<210> SEQ ID NO 10
<211> LENGTH: 44
<212> TYPE: DNA
<213> ORGANISM: Artificial Sequence
<220> FEATURE:
<223> OTHER INFORMATION: Synthetic oligonucleotide: N6RIPa

<400> SEQUENCE: 10
gcaagactgc tagccgagta gcttttcact cgcaagcacc gtat                    44

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide: N6LFa

<400> SEQUENCE: 11
aaaggacccg gtcgtcc                                                  17

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide: N6LRa

<400> SEQUENCE: 12
gttgggttgc gaaaggcc                                                 18

<210> SEQ ID NO 13
<211> LENGTH: 18

<212> TYPE: DNA
<213> ORGANISM: Artificial Sequence
<220> FEATURE:
<223> OTHER INFORMATION: Synthetic oligonucleotide: N6F3b

<400> SEQUENCE: 13
cgggagagcc atagtggt                                                 18

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide: N6R3b

<400> SEQUENCE: 14
caccgtctac gagacctcc                                                19

<210> SEQ ID NO 15
<211> LENGTH: 44
<212> TYPE: DNA
<213> ORGANISM: Artificial Sequence
<220> FEATURE:
<223> OTHER INFORMATION: Synthetic oligonucleotide: N6FIPb

<400> SEQUENCE: 15
tgagcgggtt tgatccaatg gattttttgcg gaaccggtga gtac                   44

<210> SEQ ID NO 16
<211> LENGTH: 44
<212> TYPE: DNA
<213> ORGANISM: Artificial Sequence
<220> FEATURE:
<223> OTHER INFORMATION: Synthetic oligonucleotide: N6RIPb

<400> SEQUENCE: 16
ccgcaagact gctagccgag ttttaccgta tcaggcagta ccac                    44

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide: N6LFb

<400> SEQUENCE: 17
tcgtcctggc aattccgg                                                 18

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide: N6LRb:

<400> SEQUENCE: 18
tagcgttggg ttgcgaaag                                                19

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide: N4F3b

<400> SEQUENCE: 19
accgggtcct ttcttggatt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide: N4R3b:

<400> SEQUENCE: 20
cggttggtgt tacgtttggt                                               20

<210> SEQ ID NO 21
<211> LENGTH: 44
<212> TYPE: DNA
<213> ORGANISM: Artificial Sequence
<220> FEATURE:
<223> OTHER INFORMATION: Synthetic oligonucleotide: N4FIPb

<400> SEQUENCE: 21
gacccaacac tactcggcta gcttttcgct caatgcccgg aaat                    44

<210> SEQ ID NO 22
<211> LENGTH: 43
<212> TYPE: DNA
<213> ORGANISM: Artificial Sequence
<220> FEATURE:
<223> OTHER INFORMATION: Synthetic oligonucleotide: N4RIPb

<400> SEQUENCE: 22
gccttgcggt actgcctgat ttttgattcg tgctcatggt gca                     43

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide: TF3

<400> SEQUENCE: 23
cgggagagcc atagtggt                                                 18

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide: TR3

<400> SEQUENCE: 24
cacggtctac gagacctcc                                                19

<210> SEQ ID NO 25
<211> LENGTH: 44
<212> TYPE: DNA
<213> ORGANISM: Artificial Sequence
<220> FEATURE:
<223> OTHER INFORMATION: Synthetic oligonucleotide: TFIP

<400> SEQUENCE: 25
aggcattgag cgggtttatc cattttttgcg gaaccggtga gtac                   44

<210> SEQ ID NO 26
<211> LENGTH: 44
<212> TYPE: DNA
<213> ORGANISM: Artificial Sequence

```
<220> FEATURE:
<223> OTHER INFORMATION: Synthetic oligonucleotide: TRIP

<400> SEQUENCE: 26
ccgcaagact gctagccgag ttttacccta tcaggcagta ccac            44

<210> SEQ ID NO 27
<211> LENGTH: 17
<212> TYPE: DNA
<213> ORGANISM: Artificial Sequence
<220> FEATURE:
<223> OTHER INFORMATION: Synthetic oligonucleotide: TLF

<400> SEQUENCE: 27
aaaggacccg gtcgtcc                                          17

<210> SEQ ID NO 28
<211> LENGTH: 17
<212> TYPE: DNA
<213> ORGANISM: Artificial Sequence
<220> FEATURE:
<223> OTHER INFORMATION: Synthetic oligonucleotide: TLR

<400> SEQUENCE: 28
gttgggtcgc gaaaggc                                          17

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide: 2F3

<400> SEQUENCE: 32 aatagggcg acactccg                                          18

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide: 2R3

<400> SEQUENCE: 33
gtcttcccgg caattccg                                         18

<210> SEQ ID NO 34
<211> LENGTH: 43
```

```
<212> TYPE: DNA
<213> ORGANISM: Artificial Sequence
<220> FEATURE:
<223> OTHER INFORMATION: Synthetic oligonucleotide: 2FIP

<400> SEQUENCE: 34
acgccatggc tagacgcttt ttttatgaac cactcccctg tga          43

<210> SEQ ID NO 35
<211> LENGTH: 44
<212> TYPE: DNA
<213> ORGANISM: Artificial Sequence
<220> FEATURE:
<223> OTHER INFORMATION: Synthetic oligonucleotide: 2RIP

<400> SEQUENCE: 35
tgagtgtcgt acagcctcca ggttttcggt tccgcagacc acta          44

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide: 2LF

<400> SEQUENCE: 36
gtactcaccg gttccgca                                        18

<210> SEQ ID NO 37
<211> LENGTH: 17
<212> TYPE: DNA
<213> ORGANISM: Artificial Sequence
<220> FEATURE:
<223> OTHER INFORMATION: Synthetic oligonucleotide: 2LR

<400> SEQUENCE: 37
cccccgcaag actgcta                                         17

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide: SF3

<400> SEQUENCE: 38
cccctgtgag gaactactgt                                      20

<210> SEQ ID NO 39
<211> LENGTH: 43
<212> TYPE: DNA
<213> ORGANISM: Artificial Sequence
<220> FEATURE:
<223> OTHER INFORMATION: Synthetic oligonucleotide: SFIP

<400> SEQUENCE: 39
actatggctc tcccgggagg ttttcgtcta gccatggcgt tag            43

<210> SEQ ID NO 40
<211> LENGTH: 44
<212> TYPE: DNA
<213> ORGANISM: Artificial Sequence
<220> FEATURE:
<223> OTHER INFORMATION: Synthetic oligonucleotide: SRIP

<400> SEQUENCE: 40
```
ggaaccggtg agtacaccgg ttttcccaaa tctccaggca ttga           44

<210> SEQ ID NO 41
<211> LENGTH: 19
<212> TYPE: DNA
<213> ORGANISM: Artificial Sequence
<220> FEATURE:
<223> OTHER INFORMATION: Synthetic oligonucleotide: SLF

<400> SEQUENCE: 41
aggctgcacg acactcata                                      19

<210> SEQ ID NO 42
<211> LENGTH: 19
<212> TYPE: DNA
<213> ORGANISM: Artificial Sequence
<220> FEATURE:
<223> OTHER INFORMATION: Synthetic oligonucleotide: SLR

<400> SEQUENCE: 42
gaccgggtcc tttcttgga                                      19

<210> SEQ ID NO 43
<211> LENGTH: 19
<212> TYPE: DNA
<213> ORGANISM: Artificial Sequence
<220> FEATURE:
<223> OTHER INFORMATION: Synthetic oligonucleotide: 2-F3-1

<400> SEQUENCE: 43
agtgtcgtac agcctccag                                      19

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide: 2-R3-1

<400> SEQUENCE: 44
accctatcag gcagtaccac                                     20

<210> SEQ ID NO 45
<211> LENGTH: 43
<212> TYPE: DNA
<213> ORGANISM: Artificial Sequence
<220> FEATURE:
<223> OTHER INFORMATION: Synthetic oligonucleotide: 2-FIP-1

<400> SEQUENCE: 45
acccagtctt cccggcaatt cttttcggga gagccatagt ggt           43

<210> SEQ ID NO 46
<211> LENGTH: 42
<212> TYPE: DNA
<213> ORGANISM: Artificial Sequence
<220> FEATURE:
<223> OTHER INFORMATION: Synthetic oligonucleotide: 2-BIP-1

<400> SEQUENCE: 46
ccactctatg cccggccatt ttttcaaccc aacgctactc gg            42

<210> SEQ ID NO 47
<211> LENGTH: 19
<212> TYPE: DNA
<213> ORGANISM: Artificial Sequence
<220> FEATURE:
<223> OTHER INFORMATION: Synthetic oligonucleotide: 2-LF-1

<400> SEQUENCE: 47
tgtactcacc ggttccgca                                                19

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide: 2-LR-1

<400> SEQUENCE: 48
tgcccccgca agactgcta                                                19

<210> SEQ ID NO 49
<211> LENGTH: 18
<212> TYPE: DNA
<213> ORGANISM: Artificial Sequence
<220> FEATURE:
<223> OTHER INFORMATION: Synthetic oligonucleotide: 2-F3-2

<400> SEQUENCE: 49
cgggagagcc atagtggt                                                 18

<210> SEQ ID NO 50
<211> LENGTH: 19
<212> TYPE: DNA
<213> ORGANISM: Artificial Sequence
<220> FEATURE:
<223> OTHER INFORMATION: Synthetic oligonucleotide: 2-R3-2

<400> SEQUENCE: 50
cacggtctac gagacctcc                                                19

<210> SEQ ID NO 51
<211> LENGTH: 42
<212> TYPE: DNA
<213> ORGANISM: Artificial Sequence
<220> FEATURE:
<223> OTHER INFORMATION: Synthetic oligonucleotide: 2-FIP-2

<400> SEQUENCE: 51
aatggccggg catagagtgg ttttgcggaa ccggtgagta ca                      42

<210> SEQ ID NO 52
<211> LENGTH: 44
<212> TYPE: DNA
<213> ORGANISM: Artificial Sequence
<220> FEATURE:
<223> OTHER INFORMATION: Synthetic oligonucleotide: 2-RIP-2

<400> SEQUENCE: 52
ccgcaagact gctagccgag ttttcaccct atcaggcagt acca                    44

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide: 2-LF-2

<400> SEQUENCE: 53
ccagtcttcc cggcaattcc g                                             21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide: 2-LR-2

<400> SEQUENCE: 54
tagcgttggg ttgcgaaagg c        21

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide: HCaF3

<400> SEQUENCE: 55
cccctgtgag gaactactgt        20

<210> SEQ ID NO 56
<211> LENGTH: 18
<212> TYPE: DNA
<213> ORGANISM: Artificial Sequence
<220> FEATURE:
<223> OTHER INFORMATION: Synthetic oligonucleotide: HCaR3

<400> SEQUENCE: 56
ctcggctagc agtcttgc        18

<210> SEQ ID NO 57
<211> LENGTH: 43
<212> TYPE: DNA
<213> ORGANISM: Artificial Sequence
<220> FEATURE:
<223> OTHER INFORMATION: Synthetic oligonucleotide: HCaFIP

<400> SEQUENCE: 57
actatggctc tcccgggagg ttttcgtcta gccatggcgt tag        43

<210> SEQ ID NO 58
<211> LENGTH: 44
<212> TYPE: DNA
<213> ORGANISM: Artificial Sequence
<220> FEATURE:
<223> OTHER INFORMATION: Synthetic oligonucleotide: HCaRIP

<400> SEQUENCE: 58
ggtctgcgga accggtgagt attttgaccg gacatagagt gggt        44

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide: HCaLF

<400> SEQUENCE: 59
ggaggctgta cgacactcat a        21

<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide: HCaLR
<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide: HCa2R3

<400> SEQUENCE: 61
cgtactcgca agcaccctat c                                    21

<210> SEQ ID NO 62

<400> SEQUENCE: 62

000

<210> SEQ ID NO 63
<211> LENGTH: 18
<212> TYPE: DNA
<213> ORGANISM: Artificial Sequence
<220> FEATURE:
<223> OTHER INFORMATION: Synthetic oligonucleotide: DF3-2n

<400> SEQUENCE: 63
gccatagtgg tctgcgga                                        18

<210> SEQ ID NO 64
<211> LENGTH: 18
<212> TYPE: DNA
<213> ORGANISM: Artificial Sequence
<220> FEATURE:
<223> OTHER INFORMATION: Synthetic oligonucleotide: DR3-2n

<400> SEQUENCE: 64
aagcacccta tcaggcag                                        18

<210> SEQ ID NO 65
<211> LENGTH: 44
<212> TYPE: DNA
<213> ORGANISM: Artificial Sequence
<220> FEATURE:
<223> OTHER INFORMATION: Synthetic oligonucleotide: DFIP-2n

<400> SEQUENCE: 65
tattgagcgg gttgctccaa gttttccgtg agtacaccgg aatc            44

<210> SEQ ID NO 66
<211> LENGTH: 43
<212> TYPE: DNA
<213> ORGANISM: Artificial Sequence
<220> FEATURE:
<223> OTHER INFORMATION: Synthetic oligonucleotide: DRIP-2n

<400> SEQUENCE: 66
ccagaaattt gggcgtgccc ttttaccaca aggcctttcg cga             43

<210> SEQ ID NO 67
<211> LENGTH: 19
<212> TYPE: DNA
<213> ORGANISM: Artificial Sequence
<220> FEATURE:
<223> OTHER INFORMATION: Synthetic oligonucleotide: DLF-2n

<400> SEQUENCE: 67
aggacccggt cacccagc                                                     19

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide: DLR-2n

<400> SEQUENCE: 68
cgcgagatca ctagccgagt agtg                                              24

<210> SEQ ID NO 69
<211> LENGTH: 22
<212> TYPE: DNA
<213> ORGANISM: Artificial Sequence
<220> FEATURE:
<223> OTHER INFORMATION: Synthetic oligonucleotide: HBF3

<400> SEQUENCE: 69
gaacatggag aacatcacat ca                                                22

<210> SEQ ID NO 70
<211> LENGTH: 22
<212> TYPE: DNA
<213> ORGANISM: Artificial Sequence
<220> FEATURE:
<223> OTHER INFORMATION: Synthetic oligonucleotide: HBR3

<400> SEQUENCE: 70
gataaaacgc cgcagacaca tc                                                22

<210> SEQ ID NO 71
<211> LENGTH: 48
<212> TYPE: DNA
<213> ORGANISM: Artificial Sequence
<220> FEATURE:
<223> OTHER INFORMATION: Synthetic oligonucleotide: HBFIP

<400> SEQUENCE: 71
gggtgatccc cctagaaaat tgttttgaat cctcacaata ccgcagag                    48

<210> SEQ ID NO 72
<211> LENGTH: 48
<212> TYPE: DNA
<213> ORGANISM: Artificial Sequence
<220> FEATURE:
<223> OTHER INFORMATION: Synthetic oligonucleotide: HBRIP

<400> SEQUENCE: 72
gtgtgtcttg gccaaaattc gcttttcagc gataaccagg acaaattg                    48

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide: HBLF

<400> SEQUENCE: 73
agaagtccac cacgagtcta g                                                 21

<210> SEQ ID NO 74

```
<211> LENGTH: 22
<212> TYPE: DNA
<213> ORGANISM: Artificial Sequence
<220> FEATURE:
<223> OTHER INFORMATION: Synthetic oligonucleotide: HBLR

<400> SEQUENCE: 74
tcactcacca acctcctgtc ct                                              22

<210> SEQ ID NO 75
<211> LENGTH: 19
<212> TYPE: DNA
<213> ORGANISM: Artificial Sequence
<220> FEATURE:
<223> OTHER INFORMATION: Synthetic oligonucleotide: HBF3c

<400> SEQUENCE: 75
aacatcacta ccagcacgg                                                  19

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide: HBR3c

<400> SEQUENCE: 76
accactgaac aaatggcact                                                 20

<210> SEQ ID NO 77
<211> LENGTH: 45
<212> TYPE: DNA
<213> ORGANISM: Artificial Sequence
<220> FEATURE:
<223> OTHER INFORMATION: Synthetic oligonucleotide: HBFIP3c

<400> SEQUENCE: 77
tgcagtttcc gtccgaaggt tttttttgca agacctgcac gattc                     45

<210> SEQ ID NO 78
<211> LENGTH: 44
<212> TYPE: DNA
<213> ORGANISM: Artificial Sequence
<220> FEATURE:
<223> OTHER INFORMATION: Synthetic oligonucleotide: HBRIP3c

<400> SEQUENCE: 78
ccatcccatc atcctgggct tttttaggag aaacggactg aggc                      44

<210> SEQ ID NO 79
<211> LENGTH: 23
<212> TYPE: DNA
<213> ORGANISM: Artificial Sequence
<220> FEATURE:
<223> OTHER INFORMATION: Synthetic oligonucleotide: HBLF3c

<400> SEQUENCE: 79
aaacatagag gttccttgag cag                                             23

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide: HBLR3c

<400> SEQUENCE: 80
```
tcgcaagatt cctatgggag t                    21

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide: HBF3n

<400> SEQUENCE: 81
catcactacc agcacgggac                      20

<210> SEQ ID NO 82
<211> LENGTH: 22
<212> TYPE: DNA
<213> ORGANISM: Artificial Sequence
<220> FEATURE:
<223> OTHER INFORMATION: Synthetic oligonucleotide: HBR3n

<400> SEQUENCE: 82
ccactgaaca aatggcacta gt                   22

<210> SEQ ID NO 83
<211> LENGTH: 45
<212> TYPE: DNA
<213> ORGANISM: Artificial Sequence
<220> FEATURE:
<223> OTHER INFORMATION: Synthetic oligonucleotide: HBFIP3n

<400> SEQUENCE: 83
tgcagtttcc gtccgaaggt tttttttgca agacctgcac gattc    45

<210> SEQ ID NO 84
<211> LENGTH: 45
<212> TYPE: DNA
<213> ORGANISM: Artificial Sequence
<220> FEATURE:
<223> OTHER INFORMATION: Synthetic oligonucleotide: HBRIP3n

<400> SEQUENCE: 84
ccatcccatc atcctgggct tttttcagga gaaacggact gaggc    45

<210> SEQ ID NO 85
<211> LENGTH: 24
<212> TYPE: DNA
<213> ORGANISM: Artificial Sequence
<220> FEATURE:
<223> OTHER INFORMATION: Synthetic oligonucleotide: HBLF3n

<400> SEQUENCE: 85
gaaacataga ggttccttga gcag                 24

<210> SEQ ID NO 86
<211> LENGTH: 21
<212> TYPE: DNA
<213> ORGANISM: Artificial Sequence
<220> FEATURE:
<223> OTHER INFORMATION: Synthetic oligonucleotide: HBLR3n

<400> SEQUENCE: 86
tcgcaagatt cctatgggag t                    21

<210> SEQ ID NO 87
<211> LENGTH: 23
<212> TYPE: DNA

```
<213> ORGANISM: Artificial Sequence
<220> FEATURE:
<223> OTHER INFORMATION: Synthetic oligonucleotide: HE1F3

<400> SEQUENCE: 87
gttgctgctc ctcatgtttt tgc                                         23

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide: HE1R3

<400> SEQUENCE: 88
tggcgaacac gaggtccagc                                             20

<210> SEQ ID NO 89
<211> LENGTH: 44
<212> TYPE: DNA
<213> ORGANISM: Artificial Sequence
<220> FEATURE:
<223> OTHER INFORMATION: Synthetic oligonucleotide: HE1FIP

<400> SEQUENCE: 89
accgccgctg cgccgcccac ttttatgctg cccgcgccac cgcc                  44

<210> SEQ ID NO 90
<211> LENGTH: 44
<212> TYPE: DNA
<213> ORGANISM: Artificial Sequence
<220> FEATURE:
<223> OTHER INFORMATION: Synthetic oligonucleotide: HE1RIP

<400> SEQUENCE: 90
ggcggtggtt tctggggtga ttttcggccg cagcggtgac atcg                  44

<210> SEQ ID NO 91
<211> LENGTH: 19
<212> TYPE: DNA
<213> ORGANISM: Artificial Sequence
<220> FEATURE:
<223> OTHER INFORMATION: Synthetic oligonucleotide: HE1LF

<400> SEQUENCE: 91
cggcggccag acggctgac                                              19

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide: HE1LR

<400> SEQUENCE: 92
ggttgattct cagcccttcg                                             20

<210> SEQ ID NO 93
<211> LENGTH: 22
<212> TYPE: DNA
<213> ORGANISM: Artificial Sequence
<220> FEATURE:
<223> OTHER INFORMATION: Synthetic oligonucleotide: HE3-F3

<400> SEQUENCE: 93
gcccttcgcc ctccccctata tt                                         22
```

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide: HE3-R3a

<400> SEQUENCE: 94
aggtacaggg gctgtgtcag                                               20

<210> SEQ ID NO 95
<211> LENGTH: 21
<212> TYPE: DNA
<213> ORGANISM: Artificial Sequence
<220> FEATURE:
<223> OTHER INFORMATION: Synthetic oligonucleotide: HE3-R3b

<400> SEQUENCE: 95
caacatcagg tacaggggct g                                             21

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide: HE3-R3b

<400> SEQUENCE: 96
caacatcagg tacaggggct g                                             21

<210> SEQ ID NO 97
<211> LENGTH: 48
<212> TYPE: DNA
<213> ORGANISM: Artificial Sequence
<220> FEATURE:
<223> OTHER INFORMATION: Synthetic oligonucleotide: HE3-FIP

<400> SEQUENCE: 97
cggctgccga gggcgagttc cattttgatt ctcagccctt cgccctcc                48

<210> SEQ ID NO 98
<211> LENGTH: 46
<212> TYPE: DNA
<213> ORGANISM: Artificial Sequence
<220> FEATURE:
<223> OTHER INFORMATION: Synthetic oligonucleotide: HE3-RIP

<400> SEQUENCE: 98
gtgaccagtc ccagcgcccc tcttttgaga tagcagtcaa cggcgc                  46

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide: HE3-LFc

<400> SEQUENCE: 99
gattgtgaaa cgacatcggc                                               20

<210> SEQ ID NO 100
<211> LENGTH: 22
<212> TYPE: DNA
<213> ORGANISM: Artificial Sequence
<220> FEATURE:

<223> OTHER INFORMATION: Synthetic oligonucleotide: HE3-LRc

<400> SEQUENCE: 100
ctgccccagc tggggctgcg cc                                    22

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide: HI1F3

<400> SEQUENCE: 101
caccatgcta aacacagtgg                                       20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide: HI1R3

<400> SEQUENCE: 102
tcctgaaggg tactagtagt                                       20

<210> SEQ ID NO 103
<211> LENGTH: 48
<212> TYPE: DNA
<213> ORGANISM: Artificial Sequence
<220> FEATURE:
<223> OTHER INFORMATION: Synthetic oligonucleotide: HI1FIP

<400> SEQUENCE: 103
tctgcagctt cctcattgat ggttttcaca gtgggggac atcaagca         48

<210> SEQ ID NO 104
<211> LENGTH: 48
<212> TYPE: DNA
<213> ORGANISM: Artificial Sequence
<220> FEATURE:
<223> OTHER INFORMATION: Synthetic oligonucleotide: HI1RIP

<400> SEQUENCE: 104
atgggataga ttgcatccag tgttttcttc cccttggttc tctcatct        48

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide: HI1LF

<400> SEQUENCE: 105
tcttttaaca tttgcatggc                                       20

<210> SEQ ID NO 106
<211> LENGTH: 22
<212> TYPE: DNA
<213> ORGANISM: Artificial Sequence
<220> FEATURE:
<223> OTHER INFORMATION: Synthetic oligonucleotide: HI1LR

<400> SEQUENCE: 106
catgcagggc ctattgcacc ag                                    22

```
<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide: HI2F3

<400> SEQUENCE: 107
cagggacttt ccagaagggg c                                          21

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide: HI2R3

<400> SEQUENCE: 108
aggtctttaa gcaagcaagc g                                          21

<210> SEQ ID NO 109
<211> LENGTH: 44
<212> TYPE: DNA
<213> ORGANISM: Artificial Sequence
<220> FEATURE:
<223> OTHER INFORMATION: Synthetic oligonucleotide: HI2FIP

<400> SEQUENCE: 109
aagcgggtac atttatacag ttttccaagg gagggacatg ggag                 44

<210> SEQ ID NO 110
<211> LENGTH: 41
<212> TYPE: DNA
<213> ORGANISM: Artificial Sequence
<220> FEATURE:
<223> OTHER INFORMATION: Synthetic oligonucleotide: HI2RIP

<400> SEQUENCE: 110
tgcattgtat tcagtcgctt tttgctctac ctgctagtgc t                    41

<210> SEQ ID NO 111
<211> LENGTH: 18
<212> TYPE: DNA
<213> ORGANISM: Artificial Sequence
<220> FEATURE:
<223> OTHER INFORMATION: Synthetic oligonucleotide: HI2LF

<400> SEQUENCE: 111
ggcgttcccc accagctc                                              18

<210> SEQ ID NO 112
<211> LENGTH: 18
<212> TYPE: DNA
<213> ORGANISM: Artificial Sequence
<220> FEATURE:
<223> OTHER INFORMATION: Synthetic oligonucleotide: HI2LR

<400> SEQUENCE: 112
gcggagaggc tggcagat                                              18

<210> SEQ ID NO 113
<211> LENGTH: 22
<212> TYPE: DNA
<213> ORGANISM: Artificial Sequence
<220> FEATURE:
<223> OTHER INFORMATION: Synthetic oligonucleotide: WNF3
```

```
<400> SEQUENCE: 113
gttggctctc ttggcgttct tc                                              22

<210> SEQ ID NO 114
<211> LENGTH: 22
<212> TYPE: DNA
<213> ORGANISM: Artificial Sequence
<220> FEATURE:
<223> OTHER INFORMATION: Synthetic oligonucleotide: WNR3

<400> SEQUENCE: 114
tcataagtga tagtatcatc gc                                              22

<210> SEQ ID NO 115
<211> LENGTH: 46
<212> TYPE: DNA
<213> ORGANISM: Artificial Sequence
<220> FEATURE:
<223> OTHER INFORMATION: Synthetic oligonucleotide: WNFIP

<400> SEQUENCE: 115
agcactggtc aaggtcccta gttttaggt tcacagcaat tgctcc                     46

<210> SEQ ID NO 116
<211> LENGTH: 48
<212> TYPE: DNA
<213> ORGANISM: Artificial Sequence
<220> FEATURE:
<223> OTHER INFORMATION: Synthetic oligonucleotide: WNRIP

<400> SEQUENCE: 116
cagtcatgat tggcctgatc gcttttcatc accttcccttt ggaagtta                 48

<210> SEQ ID NO 117
<211> LENGTH: 22
<212> TYPE: DNA
<213> ORGANISM: Artificial Sequence
<220> FEATURE:
<223> OTHER INFORMATION: Synthetic oligonucleotide: WNLF

<400> SEQUENCE: 117
ccttcttaaa actcagaagg tg                                              22

<210> SEQ ID NO 118
<211> LENGTH: 21
<212> TYPE: DNA
<213> ORGANISM: Artificial Sequence
<220> FEATURE:
<223> OTHER INFORMATION: Synthetic oligonucleotide: WNLR

<400> SEQUENCE: 118
gcgtaggagc agttaccctc t                                               21

<210> SEQ ID NO 119
<211> LENGTH: 22
<212> TYPE: DNA
<213> ORGANISM: Artificial Sequence
<220> FEATURE:
<223> OTHER INFORMATION: Synthetic oligonucleotide: D1F3

<400> SEQUENCE: 119
gccacggttt gagcaaaccg tg                                              22

<210> SEQ ID NO 120
<211> LENGTH: 22
```

```
<212> TYPE: DNA
<213> ORGANISM: Artificial Sequence
<220> FEATURE:
<223> OTHER INFORMATION: Synthetic oligonucleotide: D1R3

<400> SEQUENCE: 120
ttattgttat gccggggtc tc                                              22

<210> SEQ ID NO 121
<211> LENGTH: 48
<212> TYPE: DNA
<213> ORGANISM: Artificial Sequence
<220> FEATURE:
<223> OTHER INFORMATION: Synthetic oligonucleotide: D1FIP

<400> SEQUENCE: 121
gctaccccat gcgtacagct tcttttgcct gtagcttcat cgtgggga                 48

<210> SEQ ID NO 122
<211> LENGTH: 48
<212> TYPE: DNA
<213> ORGANISM: Artificial Sequence
<220> FEATURE:
<223> OTHER INFORMATION: Synthetic oligonucleotide: D1RIP

<400> SEQUENCE: 122
agactagtgg ttagaggaga cctttcagg atacagcttc ccctggtg                  48

<210> SEQ ID NO 123
<211> LENGTH: 21
<212> TYPE: DNA
<213> ORGANISM: Artificial Sequence
<220> FEATURE:
<223> OTHER INFORMATION: Synthetic oligonucleotide: D1LF

<400> SEQUENCE: 123
catgggttgc agcctcccag g                                              21

<210> SEQ ID NO 124
<211> LENGTH: 22
<212> TYPE: DNA
<213> ORGANISM: Artificial Sequence
<220> FEATURE:
<223> OTHER INFORMATION: Synthetic oligonucleotide: D1LR

<400> SEQUENCE: 124
aacataacgc agcagcgggg cc                                             22

<210> SEQ ID NO 125
<211> LENGTH: 20
<212> TYPE: DNA
<213> ORGANISM: Artificial Sequence
<220> FEATURE:
<223> OTHER INFORMATION: Synthetic oligonucleotide: D2-F3

<400> SEQUENCE: 125
caggaggaag ctgggttgac                                                20

<210> SEQ ID NO 126
<211> LENGTH: 19
<212> TYPE: DNA
<213> ORGANISM: Artificial Sequence
<220> FEATURE:
<223> OTHER INFORMATION: Synthetic oligonucleotide: D2-R3

<400> SEQUENCE: 126
```
accatggagt gtttgcaga                                                19

<210> SEQ ID NO 127
<211> LENGTH: 42
<212> TYPE: DNA
<213> ORGANISM: Artificial Sequence
<220> FEATURE:
<223> OTHER INFORMATION: Synthetic oligonucleotide: D2-FIP

<400> SEQUENCE: 127
cttccatgtt ccaagactat tttctgggtt gacatagtct tg                      42

<210> SEQ ID NO 128
<211> LENGTH: 41
<212> TYPE: DNA
<213> ORGANISM: Artificial Sequence
<220> FEATURE:
<223> OTHER INFORMATION: Synthetic oligonucleotide: D2-RIPa

<400> SEQUENCE: 128
ctgtgtgacg acgatggcgt tttggcttct gtttttatca g                       41

<210> SEQ ID NO 129
<211> LENGTH: 43
<212> TYPE: DNA
<213> ORGANISM: Artificial Sequence
<220> FEATURE:
<223> OTHER INFORMATION: Synthetic oligonucleotide: D2-RIPb

<400> SEQUENCE: 129
ctgtgtgacg acgatggcgt tttgtcagct ttgcctctat aca                     43

<210> SEQ ID NO 130
<211> LENGTH: 21
<212> TYPE: DNA
<213> ORGANISM: Artificial Sequence
<220> FEATURE:
<223> OTHER INFORMATION: Synthetic oligonucleotide: D2-LF

<400> SEQUENCE: 130
cagttcaaaa tccaatgttg g                                             21

<210> SEQ ID NO 131
<211> LENGTH: 22
<212> TYPE: DNA
<213> ORGANISM: Artificial Sequence
<220> FEATURE:
<223> OTHER INFORMATION: Synthetic oligonucleotide: CKF3

<400> SEQUENCE: 131
gactcaacca tcctggatat cg                                            22

<210> SEQ ID NO 132
<211> LENGTH: 23
<212> TYPE: DNA
<213> ORGANISM: Artificial Sequence
<220> FEATURE:
<223> OTHER INFORMATION: Synthetic oligonucleotide: CKR3

<400> SEQUENCE: 132
gcgtctccgt gtctggcacg gcc                                           23

<210> SEQ ID NO 133
<211> LENGTH: 22
<212> TYPE: DNA
<213> ORGANISM: Artificial Sequence

```
<220> FEATURE:
<223> OTHER INFORMATION: Synthetic oligonucleotide: CKR3a

<400> SEQUENCE: 133
ctgtctacat gagacgtctg tg                                                    22

<210> SEQ ID NO 134
<211> LENGTH: 48
<212> TYPE: DNA
<213> ORGANISM: Artificial Sequence
<220> FEATURE:
<223> OTHER INFORMATION: Synthetic oligonucleotide: CKFIP

<400> SEQUENCE: 134
ctctcgggat cttccgcact gcttttcagc aaggaggatg atgtcgga                        48

<210> SEQ ID NO 135
<211> LENGTH: 48
<212> TYPE: DNA
<213> ORGANISM: Artificial Sequence
<220> FEATURE:
<223> OTHER INFORMATION: Synthetic oligonucleotide: CKRIP

<400> SEQUENCE: 135
ctcgccaatt atgcgagaaa gcttttttact gcttgtaagt ccccgatc                       48

<210> SEQ ID NO 136
<211> LENGTH: 22
<212> TYPE: DNA
<213> ORGANISM: Artificial Sequence
<220> FEATURE:
<223> OTHER INFORMATION: Synthetic oligonucleotide: CKLF

<400> SEQUENCE: 136
gcagacgcag tggtacttcc tg                                                    22

<210> SEQ ID NO 137
<211> LENGTH: 22
<212> TYPE: DNA
<213> ORGANISM: Artificial Sequence
<220> FEATURE:
<223> OTHER INFORMATION: Synthetic oligonucleotide: CKLR

<400> SEQUENCE: 137
gcatctgccg caggaaaagt cc                                                    22

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide: CV-F3

<400> SEQUENCE: 138
cctggatatc ggcagtgcgc                                                       20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide: CV-R3

<400> SEQUENCE: 139
ggcacggcca ttactgcttg                                                       20
```

<210> SEQ ID NO 140
<211> LENGTH: 44
<212> TYPE: DNA
<213> ORGANISM: Artificial Sequence
<220> FEATURE:
<223> OTHER INFORMATION: Synthetic oligonucleotide: CV-FIP

<400> SEQUENCE: 140
gggatcttcc gcactgcgca ttttaggagg atgatgtcgg acag          44

<210> SEQ ID NO 141
<211> LENGTH: 44
<212> TYPE: DNA
<213> ORGANISM: Artificial Sequence
<220> FEATURE:
<223> OTHER INFORMATION: Synthetic oligonucleotide: CV-RIP

<400> SEQUENCE: 141
tatgcgagaa agctagcatc ttttctttcc agagatgttt ctgt          44

<210> SEQ ID NO 142
<211> LENGTH: 20
<212> TYPE: DNA
<213> ORGANISM: Artificial Sequence
<220> FEATURE:
<223> OTHER INFORMATION: Synthetic oligonucleotide: CV-LF

<400> SEQUENCE: 142
gggcagacgc agtggtactt                                     20

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide: CV-LR

<400> SEQUENCE: 143
tgccgcagga aaagtcctgg                                     20

<210> SEQ ID NO 144
<211> LENGTH: 20
<212> TYPE: DNA
<213> ORGANISM: Artificial Sequence
<220> FEATURE:
<223> OTHER INFORMATION: Synthetic oligonucleotide: CMF3

<400> SEQUENCE: 144
ccgacaagaa gaggccggcg                                     20

<210> SEQ ID NO 145
<211> LENGTH: 22
<212> TYPE: DNA
<213> ORGANISM: Artificial Sequence
<220> FEATURE:
<223> OTHER INFORMATION: Synthetic oligonucleotide: CMR3

<400> SEQUENCE: 145
cgatctgtcg tagtgcccac tg                                  22

<210> SEQ ID NO 146
<211> LENGTH: 48
<212> TYPE: DNA
<213> ORGANISM: Artificial Sequence
<220> FEATURE:
<223> OTHER INFORMATION: Synthetic oligonucleotide: CMFIP

<400> SEQUENCE: 146
ggtgtttgtg agaggcaggt gattttgccc tagaccgcca ggccgcac            48

<210> SEQ ID NO 147
<211> LENGTH: 49
<212> TYPE: DNA
<213> ORGANISM: Artificial Sequence
<220> FEATURE:
<223> OTHER INFORMATION: Synthetic oligonucleotide: CMRIP

<400> SEQUENCE: 147
cgtggacctg gccaaacgag ccctttatg tagaccaggc gtacgaggc            49

<210> SEQ ID NO 148
<211> LENGTH: 50
<212> TYPE: DNA
<213> ORGANISM: Artificial Sequence
<220> FEATURE:
<223> OTHER INFORMATION: Synthetic oligonucleotide: CMRIPa

<400> SEQUENCE: 148
cgtggacctg gccaaacgag ccctttttag atgttgctga ttctgtttag           50

<210> SEQ ID NO 149
<211> LENGTH: 22
<212> TYPE: DNA
<213> ORGANISM: Artificial Sequence
<220> FEATURE:
<223> OTHER INFORMATION: Synthetic oligonucleotide: CMLF

<400> SEQUENCE: 149
cataaattct tgtatttgta ag                                        22

<210> SEQ ID NO 150
<211> LENGTH: 22
<212> TYPE: DNA
<213> ORGANISM: Artificial Sequence
<220> FEATURE:
<223> OTHER INFORMATION: Synthetic oligonucleotide: CMLR

<400> SEQUENCE: 150
tcaccgacat caccagcctc gt                                        22

<210> SEQ ID NO 151
<211> LENGTH: 20
<212> TYPE: DNA
<213> ORGANISM: Artificial Sequence
<220> FEATURE:
<223> OTHER INFORMATION: Synthetic oligonucleotide: PFF3

<400> SEQUENCE: 151
gcttccttca gtaccttatg                                           20

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide: PFR3

<400> SEQUENCE: 152
gcatcaccat ccaagaaatc                                           20

<210> SEQ ID NO 153

```
<211> LENGTH: 44
<212> TYPE: DNA
<213> ORGANISM: Artificial Sequence
<220> FEATURE:
<223> OTHER INFORMATION: Synthetic oligonucleotide: PFFIP

<400> SEQUENCE: 153
ttccgtcaat tcttttaact ttttatcaaa gtctttgggt tctg            44

<210> SEQ ID NO 154
<211> LENGTH: 44
<212> TYPE: DNA
<213> ORGANISM: Artificial Sequence
<220> FEATURE:
<223> OTHER INFORMATION: Synthetic oligonucleotide: PFRIP

<400> SEQUENCE: 154
gggcaccacc aggcgtggag tttttcttgt cttaaactag tgag            44

<210> SEQ ID NO 155
<211> LENGTH: 18
<212> TYPE: DNA
<213> ORGANISM: Artificial Sequence
<220> FEATURE:
<223> OTHER INFORMATION: Synthetic oligonucleotide: PFLF

<400> SEQUENCE: 155
tcgcttgcgc gaatactc                                         18

<210> SEQ ID NO 156
<211> LENGTH: 20
<212> TYPE: DNA
<213> ORGANISM: Artificial Sequence
<220> FEATURE:
<223> OTHER INFORMATION: Synthetic oligonucleotide: PFLR

<400> SEQUENCE: 156
gcggcttaat ttgactcaac                                       20

<210> SEQ ID NO 157
<211> LENGTH: 20
<212> TYPE: DNA
<213> ORGANISM: Artificial Sequence
<220> FEATURE:
<223> OTHER INFORMATION: Synthetic oligonucleotide: EZgF3

<400> SEQUENCE: 157
ccacaagatc ttgacagcag                                       20

<210> SEQ ID NO 158
<211> LENGTH: 22
<212> TYPE: DNA
<213> ORGANISM: Artificial Sequence
<220> FEATURE:
<223> OTHER INFORMATION: Synthetic oligonucleotide: EZgR3

<400> SEQUENCE: 158
ccgcactctc ttgaaaatca ac                                    22

<210> SEQ ID NO 159
<211> LENGTH: 22
<212> TYPE: DNA
<213> ORGANISM: Artificial Sequence
<220> FEATURE:
<223> OTHER INFORMATION: Synthetic oligonucleotide: EZgR

<400> SEQUENCE: 159
```

```
gcatgagaag gaaactgtcc gc                                              22

<210> SEQ ID NO 160
<211> LENGTH: 41
<212> TYPE: DNA
<213> ORGANISM: Artificial Sequence
<220> FEATURE:
<223> OTHER INFORMATION: Synthetic oligonucleotide: EZgFIP

<400> SEQUENCE: 160
acttgataca ctgggatgat tttgtctgtc cgttcaacag g                         41

<210> SEQ ID NO 161
<211> LENGTH: 44
<212> TYPE: DNA
<213> ORGANISM: Artificial Sequence
<220> FEATURE:
<223> OTHER INFORMATION: Synthetic oligonucleotide: EZgRIP

<400> SEQUENCE: 161
acaatcttga ggaaatttgc ttttactctc ttgaaaatca acac                      44

<210> SEQ ID NO 162
<211> LENGTH: 18
<212> TYPE: DNA
<213> ORGANISM: Artificial Sequence
<220> FEATURE:
<223> OTHER INFORMATION: Synthetic oligonucleotide: EZgLF

<400> SEQUENCE: 162
ctctttgccg aacaatcc                                                   18

<210> SEQ ID NO 163
<211> LENGTH: 22
<212> TYPE: DNA
<213> ORGANISM: Artificial Sequence
<220> FEATURE:
<223> OTHER INFORMATION: Synthetic oligonucleotide: EZgLR

<400> SEQUENCE: 163
caacttatca tacaggcctt tg                                              22

<210> SEQ ID NO 164
<211> LENGTH: 20
<212> TYPE: DNA
<213> ORGANISM: Artificial Sequence
<220> FEATURE:
<223> OTHER INFORMATION: Synthetic oligonucleotide: EBZ-F3

<400> SEQUENCE: 164
gcatcaagca tcatggcacc                                                 20

<210> SEQ ID NO 165
<211> LENGTH: 22
<212> TYPE: DNA
<213> ORGANISM: Artificial Sequence
<220> FEATURE:
<223> OTHER INFORMATION: Synthetic oligonucleotide: EBZ-R3

<400> SEQUENCE: 165
ctgacatgca tataacactg tg                                              22

<210> SEQ ID NO 166
<211> LENGTH: 44
<212> TYPE: DNA
```

<213> ORGANISM: Artificial Sequence
<220> FEATURE:
<223> OTHER INFORMATION: Synthetic oligonucleotide: EBZ-FIP

<400> SEQUENCE: 166
tacctaaatg caagattgta ttttcatgcc acagttagag ggag          44

<210> SEQ ID NO 167
<211> LENGTH: 44
<212> TYPE: DNA
<213> ORGANISM: Artificial Sequence
<220> FEATURE:
<223> OTHER INFORMATION: Synthetic oligonucleotide: EBZ-RIP

<400> SEQUENCE: 167
gagtttacag cacctttat tttttaaaa acattcttaa cacc             44

<210> SEQ ID NO 168
<211> LENGTH: 21
<212> TYPE: DNA
<213> ORGANISM: Artificial Sequence
<220> FEATURE:
<223> OTHER INFORMATION: Synthetic oligonucleotide: EBZ-LF

<400> SEQUENCE: 168
tctctaaatc agttacaaag c                                    21

<210> SEQ ID NO 169
<211> LENGTH: 20
<212> TYPE: DNA
<213> ORGANISM: Artificial Sequence
<220> FEATURE:
<223> OTHER INFORMATION: Synthetic oligonucleotide: EBZ-LR

<400> SEQUENCE: 169
gaatattgca accgttgcta                                      20

<210> SEQ ID NO 170
<211> LENGTH: 21
<212> TYPE: DNA
<213> ORGANISM: Artificial Sequence
<220> FEATURE:
<223> OTHER INFORMATION: Synthetic oligonucleotide: MBVF3

<400> SEQUENCE: 170
gacacacaaa aacaagagat g                                    21

<210> SEQ ID NO 171
<211> LENGTH: 22
<212> TYPE: DNA
<213> ORGANISM: Artificial Sequence
<220> FEATURE:
<223> OTHER INFORMATION: Synthetic oligonucleotide: MBVR3

<400> SEQUENCE: 171
tccctgagtt tattgcatct at                                   22

<210> SEQ ID NO 172
<211> LENGTH: 46
<212> TYPE: DNA
<213> ORGANISM: Artificial Sequence
<220> FEATURE:
<223> OTHER INFORMATION: Synthetic oligonucleotide: MBVFIP

<400> SEQUENCE: 172
ggggctgtgg gttttgtacc ttttatgatt ttgtgtatca tataaa         46

<210> SEQ ID NO 173
<211> LENGTH: 47
<212> TYPE: DNA
<213> ORGANISM: Artificial Sequence
<220> FEATURE:
<223> OTHER INFORMATION: Synthetic oligonucleotide: MBVRIP

<400> SEQUENCE: 173
catgttcgta ataagaaggt gattttttta cagatactaa cctgatg     47

<210> SEQ ID NO 174
<211> LENGTH: 22
<212> TYPE: DNA
<213> ORGANISM: Artificial Sequence
<220> FEATURE:
<223> OTHER INFORMATION: Synthetic oligonucleotide: MVBLF

<400> SEQUENCE: 174
aatgtcaatg ttaatattct tc     22

<210> SEQ ID NO 175
<211> LENGTH: 22
<212> TYPE: DNA
<213> ORGANISM: Artificial Sequence
<220> FEATURE:
<223> OTHER INFORMATION: Synthetic oligonucleotide: MBVLR

<400> SEQUENCE: 175
gcccctcatg ttcgtaataa ga     22

<210> SEQ ID NO 176
<211> LENGTH: 22
<212> TYPE: DNA
<213> ORGANISM: Artificial Sequence
<220> FEATURE:
<223> OTHER INFORMATION: Synthetic oligonucleotide: YF2F3

<400> SEQUENCE: 176
cagagatgga gactcatact ac     22

<210> SEQ ID NO 177
<211> LENGTH: 22
<212> TYPE: DNA
<213> ORGANISM: Artificial Sequence
<220> FEATURE:
<223> OTHER INFORMATION: Synthetic oligonucleotide: YF2R3

<400> SEQUENCE: 177
acaattcctc actagttctc tg     22

<210> SEQ ID NO 178
<211> LENGTH: 48
<212> TYPE: DNA
<213> ORGANISM: Artificial Sequence
<220> FEATURE:
<223> OTHER INFORMATION: Synthetic oligonucleotide: YF2FIP

<400> SEQUENCE: 178
cacctccatg ttgtccaaga gcttttcaag tgaagataat gcccacca     48

<210> SEQ ID NO 179
<211> LENGTH: 48
<212> TYPE: DNA
<213> ORGANISM: Artificial Sequence
<220> FEATURE:

<223> OTHER INFORMATION: Synthetic oligonucleotide: YF2RIP

<400> SEQUENCE: 179
gccccactct atggcgttga agtttttcct ctggtcatcc ctcagtct          48

<210> SEQ ID NO 180
<211> LENGTH: 20
<212> TYPE: DNA
<213> ORGANISM: Artificial Sequence
<220> FEATURE:
<223> OTHER INFORMATION: Synthetic oligonucleotide: YF2LF

<400> SEQUENCE: 180
gaggcctcca accagcagac                                         20

<210> SEQ ID NO 181
<211> LENGTH: 22
<212> TYPE: DNA
<213> ORGANISM: Artificial Sequence
<220> FEATURE:
<223> OTHER INFORMATION: Synthetic oligonucleotide: YF2LR

<400> SEQUENCE: 181
caccagtttc ccctggtgaa at                                      22

<210> SEQ ID NO 182
<211> LENGTH: 23
<212> TYPE: DNA
<213> ORGANISM: Artificial Sequence
<220> FEATURE:
<223> OTHER INFORMATION: Synthetic oligonucleotide: LEF3

<400> SEQUENCE: 182
cacgcgaaag ctttgaggtt aca                                     23

<210> SEQ ID NO 183
<211> LENGTH: 23
<212> TYPE: DNA
<213> ORGANISM: Artificial Sequence
<220> FEATURE:
<223> OTHER INFORMATION: Synthetic oligonucleotide: LER3

<400> SEQUENCE: 183
gcttggatct cgtccgttga cgg                                     23

<210> SEQ ID NO 184
<211> LENGTH: 48
<212> TYPE: DNA
<213> ORGANISM: Artificial Sequence
<220> FEATURE:
<223> OTHER INFORMATION: Synthetic oligonucleotide: LEFIP

<400> SEQUENCE: 184
attaaaccgc acgctccacg tcttttgtct caggggggag tacgttcg          48

<210> SEQ ID NO 185
<211> LENGTH: 48
<212> TYPE: DNA
<213> ORGANISM: Artificial Sequence
<220> FEATURE:
<223> OTHER INFORMATION: Synthetic oligonucleotide: LERIP

<400> SEQUENCE: 185
gtaaagttcc ccgtgttgag tcttttttgca ccaccattca gggaatcg         48

<210> SEQ ID NO 186
<211> LENGTH: 22
<212> TYPE: DNA
<213> ORGANISM: Artificial Sequence
<220> FEATURE:
<223> OTHER INFORMATION: Synthetic oligonucleotide: LELF

<400> SEQUENCE: 186
gtggtgccat tccgtcaatt tc                                              22

<210> SEQ ID NO 187
<211> LENGTH: 22
<212> TYPE: DNA
<213> ORGANISM: Artificial Sequence
<220> FEATURE:
<223> OTHER INFORMATION: Synthetic oligonucleotide: LELR

<400> SEQUENCE: 187
atcctcatcc tgtccggatc tg                                              22

<210> SEQ ID NO 188
<211> LENGTH: 21
<212> TYPE: DNA
<213> ORGANISM: Artificial Sequence
<220> FEATURE:
<223> OTHER INFORMATION: Synthetic oligonucleotide: LA1F3

<400> SEQUENCE: 188
gaggctgaac taaaatgctt c                                               21

<210> SEQ ID NO 189
<211> LENGTH: 22
<212> TYPE: DNA
<213> ORGANISM: Artificial Sequence
<220> FEATURE:
<223> OTHER INFORMATION: Synthetic oligonucleotide: LA1R3

<400> SEQUENCE: 189
aatgctcatt tgtgcttcag ct                                              22

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

```
<210> SEQ ID NO 195
<400> SEQUENCE: 195

000

<210> SEQ ID NO 196
<400> SEQUENCE: 196

000

<210> SEQ ID NO 197
<400> SEQUENCE: 197

000

<210> SEQ ID NO 198
<400> SEQUENCE: 198

000

<210> SEQ ID NO 199
<400> SEQUENCE: 199

000

<210> SEQ ID NO 200
<211> LENGTH: 48
<212> TYPE: DNA
<213> ORGANISM: Artificial Sequence
<220> FEATURE:
<223> OTHER INFORMATION: Synthetic oligonucleotide: LA1FIP

<400> SEQUENCE: 200
ttgaagtcaa acagcctcag cattttgaac acagctgtgg caaaatgt          48

<210> SEQ ID NO 201
<211> LENGTH: 48
<212> TYPE: DNA
<213> ORGANISM: Artificial Sequence
<220> FEATURE:
<223> OTHER INFORMATION: Synthetic oligonucleotide: LA1RIP

<400> SEQUENCE: 201
aacaagccat tcaaaggctg aattttaatg ctcatttgtg cttcagct          48

<210> SEQ ID NO 202
<211> LENGTH: 22
<212> TYPE: DNA
<213> ORGANISM: Artificial Sequence
<220> FEATURE:
<223> OTHER INFORMATION: Synthetic oligonucleotide: LA1LF

<400> SEQUENCE: 202
tgtcacaaaa ttcctcatca tg                                      22

<210> SEQ ID NO 203
<211> LENGTH: 22
<212> TYPE: DNA
<213> ORGANISM: Artificial Sequence
```

```
<220> FEATURE:
<223> OTHER INFORMATION: Synthetic oligonucleotide: LA1LR

<400> SEQUENCE: 203
agctgaagca caaatgagca tt                                          22

<210> SEQ ID NO 204
<211> LENGTH: 20
<212> TYPE: DNA
<213> ORGANISM: Artificial Sequence
<220> FEATURE:
<223> OTHER INFORMATION: Synthetic oligonucleotide: LA2F3

<400> SEQUENCE: 204
ttccggggga gtgcatcaat                                             20

<210> SEQ ID NO 205
<211> LENGTH: 22
<212> TYPE: DNA
<213> ORGANISM: Artificial Sequence
<220> FEATURE:
<223> OTHER INFORMATION: Synthetic oligonucleotide: LA2R3

<400> SEQUENCE: 205
gcaacttgac ccaaatgcta ag                                          22

<210> SEQ ID NO 206
<211> LENGTH: 48
<212> TYPE: DNA
<213> ORGANISM: Artificial Sequence
<220> FEATURE:
<223> OTHER INFORMATION: Synthetic oligonucleotide: LA2FIP

<400> SEQUENCE: 206
aagcaggatg ctaagtactc acttttcagc actggtcaag cccggttg              48

<210> SEQ ID NO 207
<211> LENGTH: 46
<212> TYPE: DNA
<213> ORGANISM: Artificial Sequence
<220> FEATURE:
<223> OTHER INFORMATION: Synthetic oligonucleotide: LA2RIP

<400> SEQUENCE: 207
aatcagtagg ttcacggaag aatttttgaa ggaagacctg aagatc                46

<210> SEQ ID NO 208
<211> LENGTH: 22
<212> TYPE: DNA
<213> ORGANISM: Artificial Sequence
<220> FEATURE:
<223> OTHER INFORMATION: Synthetic oligonucleotide: LA2LF

<400> SEQUENCE: 208
ttgatgtcac agacctcttc gc                                          22

<210> SEQ ID NO 209
<211> LENGTH: 22
<212> TYPE: DNA
<213> ORGANISM: Artificial Sequence
<220> FEATURE:
<223> OTHER INFORMATION: Synthetic oligonucleotide: LA2LR

<400> SEQUENCE: 209
aagttcaggc tgctacatac ac                                          22
```

```
<210> SEQ ID NO 210
<211> LENGTH: 22
<212> TYPE: DNA
<213> ORGANISM: Artificial Sequence
<220> FEATURE:
<223> OTHER INFORMATION: Synthetic oligonucleotide: TB1F3

<400> SEQUENCE: 210
cggttcaggc ttcaccacag tg                                              22

<210> SEQ ID NO 211
<211> LENGTH: 22
<212> TYPE: DNA
<213> ORGANISM: Artificial Sequence
<220> FEATURE:
<223> OTHER INFORMATION: Synthetic oligonucleotide: TB1R3

<400> SEQUENCE: 211
gagttggatc tgatgtccga gt                                              22

<210> SEQ ID NO 212
<211> LENGTH: 48
<212> TYPE: DNA
<213> ORGANISM: Artificial Sequence
<220> FEATURE:
<223> OTHER INFORMATION: Synthetic oligonucleotide: TB1FIP

<400> SEQUENCE: 212
attgagccaa gccctttgct gattttcggc gaccctaagg ttgacgac                  48

<210> SEQ ID NO 213
<211> LENGTH: 48
<212> TYPE: DNA
<213> ORGANISM: Artificial Sequence
<220> FEATURE:
<223> OTHER INFORMATION: Synthetic oligonucleotide: TB1RIP

<400> SEQUENCE: 213
cgtccagcca ttgaccatcg tcttttgcgc tcgatttcgt tttggaca                  48

<210> SEQ ID NO 214
<211> LENGTH: 22
<212> TYPE: DNA
<213> ORGANISM: Artificial Sequence
<220> FEATURE:
<223> OTHER INFORMATION: Synthetic oligonucleotide: TB1LF

<400> SEQUENCE: 214
cgctgagatt agcatcactg ct                                              22

<210> SEQ ID NO 215
<211> LENGTH: 22
<212> TYPE: DNA
<213> ORGANISM: Artificial Sequence
<220> FEATURE:
<223> OTHER INFORMATION: Synthetic oligonucleotide: TB1LR

<400> SEQUENCE: 215
gctctgttat ccgtgccgag ca                                              22

<210> SEQ ID NO 216
<211> LENGTH: 22
<212> TYPE: DNA
<213> ORGANISM: Artificial Sequence
<220> FEATURE:
<223> OTHER INFORMATION: Synthetic oligonucleotide: TB2F3
```

-continued

<210> SEQ ID NO 217
<211> LENGTH: 23
<212> TYPE: DNA
<213> ORGANISM: Artificial Sequence
<220> FEATURE:
<223> OTHER INFORMATION: Synthetic oligonucleotide: TB2R3

<400> SEQUENCE: 217
agaacgttgt cggaagaaca cgc                                          23

<210> SEQ ID NO 218
<211> LENGTH: 48
<212> TYPE: DNA
<213> ORGANISM: Artificial Sequence
<220> FEATURE:
<223> OTHER INFORMATION: Synthetic oligonucleotide: TB2FIP

<400> SEQUENCE: 218
atcttgcgtt gggcgtacat gattttcgtg agctcaccga tctttcgt               48

<210> SEQ ID NO 219
<211> LENGTH: 48
<212> TYPE: DNA
<213> ORGANISM: Artificial Sequence
<220> FEATURE:
<223> OTHER INFORMATION: Synthetic oligonucleotide: TB2RIP

<400> SEQUENCE: 219
ctgtccgaga tggccgagcg cctttttagcg cttggagcgc tgacggat              48

<210> SEQ ID NO 220
<211> LENGTH: 22
<212> TYPE: DNA
<213> ORGANISM: Artificial Sequence
<220> FEATURE:
<223> OTHER INFORMATION: Synthetic oligonucleotide: TB2LF

<400> SEQUENCE: 220
ggttgtgtga tcacggccga ac                                           22

<210> SEQ ID NO 221
<211> LENGTH: 22
<212> TYPE: DNA
<213> ORGANISM: Artificial Sequence
<220> FEATURE:
<223> OTHER INFORMATION: Synthetic oligonucleotide: TB2LR

<400> SEQUENCE: 221
gtgaggtctt tgatcacgtc aa                                           22

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide: ME1F3

<400> SEQUENCE: 222
caaggtgcgc gcggtacgta                                              20

<210> SEQ ID NO 223

-continued

```
<211> LENGTH: 20
<212> TYPE: DNA
<213> ORGANISM: Artificial Sequence
<220> FEATURE:
<223> OTHER INFORMATION: Synthetic oligonucleotide: ME1R3

<400> SEQUENCE: 223
gcaatgagcc tctcaaccag                                               20

<210> SEQ ID NO 224
<211> LENGTH: 44
<212> TYPE: DNA
<213> ORGANISM: Artificial Sequence
<220> FEATURE:
<223> OTHER INFORMATION: Synthetic oligonucleotide: ME1FIP

<400> SEQUENCE: 224
ttcctgaacc acagagtggc ttttgagcag cgctcaactc tgaa                    44

<210> SEQ ID NO 225
<211> LENGTH: 44
<212> TYPE: DNA
<213> ORGANISM: Artificial Sequence
<220> FEATURE:
<223> OTHER INFORMATION: Synthetic oligonucleotide: ME1RIP

<400> SEQUENCE: 225
gcctatgaag tggtgaaggc ttttggaggt gtctagtgtg tcca                    44

<210> SEQ ID NO 226
<211> LENGTH: 20
<212> TYPE: DNA
<213> ORGANISM: Artificial Sequence
<220> FEATURE:
<223> OTHER INFORMATION: Synthetic oligonucleotide: ME1LF

<400> SEQUENCE: 226
gttagagaca catggtcttg                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic oligonucleotide: ME1LR

<400> SEQUENCE: 227
ctatgtgccc atccggctgg                                               20

<210> SEQ ID NO 228
<211> LENGTH: 21
<212> TYPE: DNA
<213> ORGANISM: Artificial Sequence
<220> FEATURE:
<223> OTHER INFORMATION: Synthetic oligonucleotide: ME2F3

<400> SEQUENCE: 228
cgttgtcaac gatgttgtcc t                                             21

<210> SEQ ID NO 229
<211> LENGTH: 22
<212> TYPE: DNA
<213> ORGANISM: Artificial Sequence
<220> FEATURE:
<223> OTHER INFORMATION: Synthetic oligonucleotide: ME2R3

<400> SEQUENCE: 229
```

```
cacctaagcc agtgagaact ac                                              22

<210> SEQ ID NO 230
<211> LENGTH: 22
<212> TYPE: DNA
<213> ORGANISM: Artificial Sequence
<220> FEATURE:
<223> OTHER INFORMATION: Synthetic oligonucleotide: ME2R3a

<400> SEQUENCE: 230
acagagttgc aaaccttgta cg                                              22

<210> SEQ ID NO 231
<211> LENGTH: 44
<212> TYPE: DNA
<213> ORGANISM: Artificial Sequence
<220> FEATURE:
<223> OTHER INFORMATION: Synthetic oligonucleotide: ME2FIP

<400> SEQUENCE: 231
cacgcaactt gtcaagggtg ttttcgcaat tctctctgga acca                      44

<210> SEQ ID NO 232
<211> LENGTH: 45
<212> TYPE: DNA
<213> ORGANISM: Artificial Sequence
<220> FEATURE:
<223> OTHER INFORMATION: Synthetic oligonucleotide: ME2RIP

<400> SEQUENCE: 232
cgtagcagtc actgccggcc tttttaatgg cggcatactg taatc                     45

<210> SEQ ID NO 233
<211> LENGTH: 21
<212> TYPE: DNA
<213> ORGANISM: Artificial Sequence
<220> FEATURE:
<223> OTHER INFORMATION: Synthetic oligonucleotide: ME2LF

<400> SEQUENCE: 233
cacctttgag aagctggcgt a                                               21

<210> SEQ ID NO 234
<211> LENGTH: 22
<212> TYPE: DNA
<213> ORGANISM: Artificial Sequence
<220> FEATURE:
<223> OTHER INFORMATION: Synthetic oligonucleotide: ME2LR

<400> SEQUENCE: 234
gctattaatg ttggtggtac ag                                              22

<210> SEQ ID NO 235
<211> LENGTH: 23
<212> TYPE: DNA
<213> ORGANISM: Artificial Sequence
<220> FEATURE:
<223> OTHER INFORMATION: Synthetic oligonucleotide: PV1F3

<400> SEQUENCE: 235
agttatctga ccaccccat gcc                                              23

<210> SEQ ID NO 236
<211> LENGTH: 22
<212> TYPE: DNA
```

<213> ORGANISM: Artificial Sequence
<220> FEATURE:
<223> OTHER INFORMATION: Synthetic oligonucleotide: PV1R3

<400> SEQUENCE: 236
ggatttattc ccaacttagc ca             22

<210> SEQ ID NO 237
<211> LENGTH: 48
<212> TYPE: DNA
<213> ORGANISM: Artificial Sequence
<220> FEATURE:
<223> OTHER INFORMATION: Synthetic oligonucleotide: PV1FIP

<400> SEQUENCE: 237
cccaacatag ttagtaccgg gttttttgca gtattatcta gtgaagac             48

<210> SEQ ID NO 238
<211> LENGTH: 48
<212> TYPE: DNA
<213> ORGANISM: Artificial Sequence
<220> FEATURE:
<223> OTHER INFORMATION: Synthetic oligonucleotide: PV1RIP

<400> SEQUENCE: 238
acccggtact aactatgttg ggttttcatg aatccttgca gcactgtc             48

<210> SEQ ID NO 239
<211> LENGTH: 19
<212> TYPE: DNA
<213> ORGANISM: Artificial Sequence
<220> FEATURE:
<223> OTHER INFORMATION: Synthetic oligonucleotide: PV1LF

<400> SEQUENCE: 239
cttgcccagg cttgtgtaa             19

<210> SEQ ID NO 240
<211> LENGTH: 20
<212> TYPE: DNA
<213> ORGANISM: Artificial Sequence
<220> FEATURE:
<223> OTHER INFORMATION: Synthetic oligonucleotide: PV1LR

<400> SEQUENCE: 240
cctggcaatg agctacaagc             20

<210> SEQ ID NO 241
<211> LENGTH: 23
<212> TYPE: DNA
<213> ORGANISM: Artificial Sequence
<220> FEATURE:
<223> OTHER INFORMATION: Synthetic oligonucleotide: PV2F3

<400> SEQUENCE: 241
agttatctga ccaccccat gcc             23

<210> SEQ ID NO 242
<211> LENGTH: 22
<212> TYPE: DNA
<213> ORGANISM: Artificial Sequence
<220> FEATURE:
<223> OTHER INFORMATION: Synthetic oligonucleotide: PV2R3

<400> SEQUENCE: 242
ccaacttagc cagttggcta ta             22

<210> SEQ ID NO 243
<211> LENGTH: 48
<212> TYPE: DNA
<213> ORGANISM: Artificial Sequence
<220> FEATURE:
<223> OTHER INFORMATION: Synthetic oligonucleotide: PV2FIP

<400> SEQUENCE: 243
cccaacatag ttagtaccgg gttttcatc cagtagcagt catgcaga        48

<210> SEQ ID NO 244
<211> LENGTH: 48
<212> TYPE: DNA
<213> ORGANISM: Artificial Sequence
<220> FEATURE:
<223> OTHER INFORMATION: Synthetic oligonucleotide: PV2RIP

<400> SEQUENCE: 244
cctggcaatg agctacaagc tgttttaact tagccagttg gctatacc        48

<210> SEQ ID NO 245
<211> LENGTH: 22
<212> TYPE: DNA
<213> ORGANISM: Artificial Sequence
<220> FEATURE:
<223> OTHER INFORMATION: Synthetic oligonucleotide: PV2LF

<400> SEQUENCE: 245
ccaggcttgt gtaagtcttc ac        22

<210> SEQ ID NO 246
<211> LENGTH: 23
<212> TYPE: DNA
<213> ORGANISM: Artificial Sequence
<220> FEATURE:
<223> OTHER INFORMATION: Synthetic oligonucleotide: PV2LR

<400> SEQUENCE: 246
cagtgctgca aggattcatg act        23

<210> SEQ ID NO 247
<211> LENGTH: 20
<212> TYPE: DNA
<213> ORGANISM: Artificial Sequence
<220> FEATURE:
<223> OTHER INFORMATION: Synthetic oligonucleotide: JEF3

<400> SEQUENCE: 247
cacggcccaa gcctcgtcta        20

<210> SEQ ID NO 248
<211> LENGTH: 23
<212> TYPE: DNA
<213> ORGANISM: Artificial Sequence
<220> FEATURE:
<223> OTHER INFORMATION: Synthetic oligonucleotide: JER3

<400> SEQUENCE: 248
cggcgctctg tgcctagtag ctg        23

<210> SEQ ID NO 249
<211> LENGTH: 44
<212> TYPE: DNA
<213> ORGANISM: Artificial Sequence
<220> FEATURE:

```
<223> OTHER INFORMATION: Synthetic oligonucleotide: JEFIP

<400> SEQUENCE: 249 tcgaggggc ttgggccgca ttttgtgtaa ggactagagg ttag                44

<210> SEQ ID NO 250
<211> LENGTH: 44
<212> TYPE: DNA
<213> ORGANISM: Artificial Sequence
<220> FEATURE:
<223> OTHER INFORMATION: Synthetic oligonucleotide: JERIP

<400> SEQUENCE: 250
gaggaggtgg aaggactaga ttttgttgag atagagcaga agat                44

<210> SEQ ID NO 251
<211> LENGTH: 22
<212> TYPE: DNA
<213> ORGANISM: Artificial Sequence
<220> FEATURE:
<223> OTHER INFORMATION: Synthetic oligonucleotide: JELF

<400> SEQUENCE: 251
tgttgtttcc acggggtctc ct                                       22

<210> SEQ ID NO 252
<211> LENGTH: 22
<212> TYPE: DNA
<213> ORGANISM: Artificial Sequence
<220> FEATURE:
<223> OTHER INFORMATION: Synthetic oligonucleotide: JELR

<400> SEQUENCE: 252
ttgacacctg ggaatagact gg                                       22

<210> SEQ ID NO 253
<211> LENGTH: 20
<212> TYPE: DNA
<213> ORGANISM: Artificial Sequence
<220> FEATURE:
<223> OTHER INFORMATION: Synthetic oligonucleotide: JE1F3

<400> SEQUENCE: 253
ccaggaggac tgggttaaca                                          20

<210> SEQ ID NO 254
<211> LENGTH: 20
<212> TYPE: DNA
<213> ORGANISM: Artificial Sequence
<220> FEATURE:
<223> OTHER INFORMATION: Synthetic oligonucleotide: JE1R3

<400> SEQUENCE: 254
agtagctgat gttgagatag                                          20

<210> SEQ ID NO 255
<211> LENGTH: 44
<212> TYPE: DNA
<213> ORGANISM: Artificial Sequence
<220> FEATURE:
<223> OTHER INFORMATION: Synthetic oligonucleotide: JE1FIP

<400> SEQUENCE: 255
ttgtttccac ggggtctcct ttttcacggc ccaagcctcg tcta                44
```

-continued

```
<210> SEQ ID NO 256
<211> LENGTH: 44
<212> TYPE: DNA
<213> ORGANISM: Artificial Sequence
<220> FEATURE:
<223> OTHER INFORMATION: Synthetic oligonucleotide: JE1RIP

<400> SEQUENCE: 256
tgcggcccaa gcccctcga ttttgaagat ctcccagtct attc                44

<210> SEQ ID NO 257
<211> LENGTH: 20
<212> TYPE: DNA
<213> ORGANISM: Artificial Sequence
<220> FEATURE:
<223> OTHER INFORMATION: Synthetic oligonucleotide: JE1LF

<400> SEQUENCE: 257
ctaacctcta gtccttacac                                          20

<210> SEQ ID NO 258
<211> LENGTH: 22
<212> TYPE: DNA
<213> ORGANISM: Artificial Sequence
<220> FEATURE:
<223> OTHER INFORMATION: Synthetic oligonucleotide: JE1LR

<400> SEQUENCE: 258
ctagaggtta gaggagaccc cg                                       22

<210> SEQ ID NO 259
<211> LENGTH: 22
<212> TYPE: DNA
<213> ORGANISM: Artificial Sequence
<220> FEATURE:
<223> OTHER INFORMATION: Synthetic oligonucleotide: SA1F3

<400> SEQUENCE: 259
tactgtcgtt gacaagaaac ga                                       22

<210> SEQ ID NO 260
<211> LENGTH: 22
<212> TYPE: DNA
<213> ORGANISM: Artificial Sequence
<220> FEATURE:
<223> OTHER INFORMATION: Synthetic oligonucleotide: SA1R3

<400> SEQUENCE: 260
gctctactag accacaagtg cc                                       22

<210> SEQ ID NO 261
<211> LENGTH: 44
<212> TYPE: DNA
<213> ORGANISM: Artificial Sequence
<220> FEATURE:
<223> OTHER INFORMATION: Synthetic oligonucleotide: SA1FIP

<400> SEQUENCE: 261
gacgaaacct aggtatgctg ttttactcgt ccctcttctg caga               44

<210> SEQ ID NO 262
<211> LENGTH: 44
<212> TYPE: DNA
<213> ORGANISM: Artificial Sequence
<220> FEATURE:
<223> OTHER INFORMATION: Synthetic oligonucleotide: SA1RIP
```

```
<400> SEQUENCE: 262
gatggagagc cttgttcttg ttttactagc acgtctctaa cctg            44

<210> SEQ ID NO 263
<211> LENGTH: 20
<212> TYPE: DNA
<213> ORGANISM: Artificial Sequence
<220> FEATURE:
<223> OTHER INFORMATION: Synthetic oligonucleotide: SA1LF

<400> SEQUENCE: 263
gatcgactgc aacacggacg                                        20

<210> SEQ ID NO 264
<211> LENGTH: 22
<212> TYPE: DNA
<213> ORGANISM: Artificial Sequence
<220> FEATURE:
<223> OTHER INFORMATION: Synthetic oligonucleotide: SA1LR

<400> SEQUENCE: 264
cacacgtcca actcagtttg cc                                     22

<210> SEQ ID NO 265
<211> LENGTH: 22
<212> TYPE: DNA
<213> ORGANISM: Artificial Sequence
<220> FEATURE:
<223> OTHER INFORMATION: Synthetic oligonucleotide: SA2F3

<400> SEQUENCE: 265
tgggagattc tcaaatttct ca                                     22

<210> SEQ ID NO 266
<211> LENGTH: 22
<212> TYPE: DNA
<213> ORGANISM: Artificial Sequence
<220> FEATURE:
<223> OTHER INFORMATION: Synthetic oligonucleotide: SA2R3

<400> SEQUENCE: 266
tgccttaaga ggcatgagta gt                                     22

<210> SEQ ID NO 267
<211> LENGTH: 44
<212> TYPE: DNA
<213> ORGANISM: Artificial Sequence
<220> FEATURE:
<223> OTHER INFORMATION: Synthetic oligonucleotide: SA2FIP

<400> SEQUENCE: 267
ccagcgatag tgacttgatc ttttgtcaag ggtcaaatac aggt            44

<210> SEQ ID NO 268
<211> LENGTH: 44
<212> TYPE: DNA
<213> ORGANISM: Artificial Sequence
<220> FEATURE:
<223> OTHER INFORMATION: Synthetic oligonucleotide: SA2RIP

<400> SEQUENCE: 268
tgcgatcact caacttaggt tttttgctcc ttgccacgta taca            44

<210> SEQ ID NO 269
<211> LENGTH: 21
```

-continued

```
<212> TYPE: DNA
<213> ORGANISM: Artificial Sequence
<220> FEATURE:
<223> OTHER INFORMATION: Synthetic oligonucleotide: SA2LF

<400> SEQUENCE: 269
atgcacattt cgagtgcctt g                                          21

<210> SEQ ID NO 270
<211> LENGTH: 22
<212> TYPE: DNA
<213> ORGANISM: Artificial Sequence
<220> FEATURE:
<223> OTHER INFORMATION: Synthetic oligonucleotide: SA2LR

<400> SEQUENCE: 270
gaagtcttca tcgctcaaag ca                                         22

<210> SEQ ID NO 271
<211> LENGTH: 22
<212> TYPE: DNA
<213> ORGANISM: Artificial Sequence
<220> FEATURE:
<223> OTHER INFORMATION: Synthetic oligonucleotide: SA3F3

<400> SEQUENCE: 271
cacatgatgt ttcatctgca at                                         22

<210> SEQ ID NO 272
<211> LENGTH: 22
<212> TYPE: DNA
<213> ORGANISM: Artificial Sequence
<220> FEATURE:
<223> OTHER INFORMATION: Synthetic oligonucleotide: SA3R3

<400> SEQUENCE: 272
ttgtgatagc cacattgaag cg                                         22

<210> SEQ ID NO 273
<211> LENGTH: 44
<212> TYPE: DNA
<213> ORGANISM: Artificial Sequence
<220> FEATURE:
<223> OTHER INFORMATION: Synthetic oligonucleotide: SA3FIP

<400> SEQUENCE: 273
ttctgtgaat tataaggtga ttttataggc gttgtaagag aatt                 44

<210> SEQ ID NO 274
<211> LENGTH: 44
<212> TYPE: DNA
<213> ORGANISM: Artificial Sequence
<220> FEATURE:
<223> OTHER INFORMATION: Synthetic oligonucleotide: SA3RIP

<400> SEQUENCE: 274
aatcttagga ttgcctacgc ttttgacatt acaagagtgt gctg                 44

<210> SEQ ID NO 275
<211> LENGTH: 22
<212> TYPE: DNA
<213> ORGANISM: Artificial Sequence
<220> FEATURE:
<223> OTHER INFORMATION: Synthetic oligonucleotide: SA3LF

<400> SEQUENCE: 275
```
tccaagcagg attgcgtgta ag                                              22

<210> SEQ ID NO 276
<211> LENGTH: 22
<212> TYPE: DNA
<213> ORGANISM: Artificial Sequence
<220> FEATURE:
<223> OTHER INFORMATION: Synthetic oligonucleotide: SA3LR

<400> SEQUENCE: 276
cacagggttc tgaatatgac ta                                              22

<210> SEQ ID NO 277
<211> LENGTH: 22
<212> TYPE: DNA
<213> ORGANISM: Artificial Sequence
<220> FEATURE:
<223> OTHER INFORMATION: Synthetic oligonucleotide: TCF3

<400> SEQUENCE: 277
catgccttcc ctcaactcac gg                                              22

<210> SEQ ID NO 278
<211> LENGTH: 22
<212> TYPE: DNA
<213> ORGANISM: Artificial Sequence
<220> FEATURE:
<223> OTHER INFORMATION: Synthetic oligonucleotide: TCR3

<400> SEQUENCE: 278
gtgtcatcgt ttgcagtgtg ga                                              22

<210> SEQ ID NO 279
<211> LENGTH: 44
<212> TYPE: DNA
<213> ORGANISM: Artificial Sequence
<220> FEATURE:
<223> OTHER INFORMATION: Synthetic oligonucleotide: TCFIP

<400> SEQUENCE: 279
gtgcggtcta agaatttcac ttttatccag gaatgaagga gggt                      44

<210> SEQ ID NO 280
<211> LENGTH: 44
<212> TYPE: DNA
<213> ORGANISM: Artificial Sequence
<220> FEATURE:
<223> OTHER INFORMATION: Synthetic oligonucleotide: TCRIP

<400> SEQUENCE: 280
actacagcga aggcattctt ttttatggtc tctaatcatc ttcg                      44

<210> SEQ ID NO 281
<211> LENGTH: 20
<212> TYPE: DNA
<213> ORGANISM: Artificial Sequence
<220> FEATURE:
<223> OTHER INFORMATION: Synthetic oligonucleotide: TCLF

<400> SEQUENCE: 281
gacgcaccag tacgttctcc                                                 20

<210> SEQ ID NO 282
<211> LENGTH: 22
<212> TYPE: DNA
<213> ORGANISM: Artificial Sequence

```
<220> FEATURE:
<223> OTHER INFORMATION: Synthetic oligonucleotide: TCLR

<400> SEQUENCE: 282
ctcaatcaag aaccaaagtg tg                                             22

<210> SEQ ID NO 283
<211> LENGTH: 22
<212> TYPE: DNA
<213> ORGANISM: Artificial Sequence
<220> FEATURE:
<223> OTHER INFORMATION: Synthetic oligonucleotide: TRbF3

<400> SEQUENCE: 283
agaagtcatt tcaggaatct gc                                             22

<210> SEQ ID NO 284
<211> LENGTH: 22
<212> TYPE: DNA
<213> ORGANISM: Artificial Sequence
<220> FEATURE:
<223> OTHER INFORMATION: Synthetic oligonucleotide: TRbR3

<400> SEQUENCE: 284
cctgaatgcg acgccatgcc tc                                             22

<210> SEQ ID NO 285
<211> LENGTH: 44
<212> TYPE: DNA
<213> ORGANISM: Artificial Sequence
<220> FEATURE:
<223> OTHER INFORMATION: Synthetic oligonucleotide: TRbFI

<400> SEQUENCE: 285
gcatcgtgaa ggttacgtag ttttaatcaa ggacgcgaag cgcc                     44

<210> SEQ ID NO 286
<211> LENGTH: 44
<212> TYPE: DNA
<213> ORGANISM: Artificial Sequence
<220> FEATURE:
<223> OTHER INFORMATION: Synthetic oligonucleotide: TRbRI

<400> SEQUENCE: 286
acttggagga cgccgaagcc ttttgtttgt cgaggttctc gtgg                     44

<210> SEQ ID NO 287
<211> LENGTH: 20
<212> TYPE: DNA
<213> ORGANISM: Artificial Sequence
<220> FEATURE:
<223> OTHER INFORMATION: Synthetic oligonucleotide: TRbLF

<400> SEQUENCE: 287
gtcctcgcag tgttgcttaa                                                20

<210> SEQ ID NO 288
<211> LENGTH: 20
<212> TYPE: DNA
<213> ORGANISM: Artificial Sequence
<220> FEATURE:
<223> OTHER INFORMATION: Synthetic oligonucleotide: TRbLR

<400> SEQUENCE: 288
ggttcgccac gcagaaggag                                                20
```

<210> SEQ ID NO 289
<211> LENGTH: 19
<212> TYPE: DNA
<213> ORGANISM: Artificial Sequence
<220> FEATURE:
<223> OTHER INFORMATION: Synthetic oligonucleotide: TRbrF3

<400> SEQUENCE: 289
aagtaccttg gcgctcgcg                                          19

<210> SEQ ID NO 290
<211> LENGTH: 20
<212> TYPE: DNA
<213> ORGANISM: Artificial Sequence
<220> FEATURE:
<223> OTHER INFORMATION: Synthetic oligonucleotide: TRbrR3

<400> SEQUENCE: 290
tgcgttgagt acgcatcttg                                         20

<210> SEQ ID NO 291
<211> LENGTH: 44
<212> TYPE: DNA
<213> ORGANISM: Artificial Sequence
<220> FEATURE:
<223> OTHER INFORMATION: Synthetic oligonucleotide: TRbrFI

<400> SEQUENCE: 291
tgcaaacctt cttgacgggc ttttctaaag ctgctggcag tgcc              44

<210> SEQ ID NO 292
<211> LENGTH: 44
<212> TYPE: DNA
<213> ORGANISM: Artificial Sequence
<220> FEATURE:
<223> OTHER INFORMATION: Synthetic oligonucleotide: TRbrRI

<400> SEQUENCE: 292
gcagacgtcg caggaatcgc ttttactatg tttgacgccg cggc              44

<210> SEQ ID NO 293
<211> LENGTH: 20
<212> TYPE: DNA
<213> ORGANISM: Artificial Sequence
<220> FEATURE:
<223> OTHER INFORMATION: Synthetic oligonucleotide: TRbrLF

<400> SEQUENCE: 293
cttcgtcaaa ggcggtgcca                                         20

<210> SEQ ID NO 294
<211> LENGTH: 20
<212> TYPE: DNA
<213> ORGANISM: Artificial Sequence
<220> FEATURE:
<223> OTHER INFORMATION: Synthetic oligonucleotide: TRbrLR

<400> SEQUENCE: 294
caagtatcgg cagcaaccga                                         20

<210> SEQ ID NO 295
<211> LENGTH: 20
<212> TYPE: DNA
<213> ORGANISM: Artificial Sequence
<220> FEATURE:
<223> OTHER INFORMATION: Synthetic oligonucleotide: ZK1-F3

<400> SEQUENCE: 295
ggatttggaa acgagagttt                                          20

<210> SEQ ID NO 296
<211> LENGTH: 20
<212> TYPE: DNA
<213> ORGANISM: Artificial Sequence
<220> FEATURE:
<223> OTHER INFORMATION: Synthetic oligonucleotide: ZK1-R3

<400> SEQUENCE: 296
ctattgatga gacccagtga                                          20

<210> SEQ ID NO 297
<211> LENGTH: 44
<212> TYPE: DNA
<213> ORGANISM: Artificial Sequence
<220> FEATURE:
<223> OTHER INFORMATION: Synthetic oligonucleotide: ZK1-FIP

<400> SEQUENCE: 297
gcccccaaag gggctcacac ttttggattc cggattgtca atat               44

<210> SEQ ID NO 298
<211> LENGTH: 44
<212> TYPE: DNA
<213> ORGANISM: Artificial Sequence
<220> FEATURE:
<223> OTHER INFORMATION: Synthetic oligonucleotide: ZK1-RIP

<400> SEQUENCE: 298
gaggctgcca gccggacttc ttttgcttga ttgccgtgaa tctc               44

<210> SEQ ID NO 299
<211> LENGTH: 20
<212> TYPE: DNA
<213> ORGANISM: Artificial Sequence
<220> FEATURE:
<223> OTHER INFORMATION: Synthetic oligonucleotide: ZK1-LF

<400> SEQUENCE: 299
gggctactcc gcgttttagc                                          20

<210> SEQ ID NO 300
<211> LENGTH: 20
<212> TYPE: DNA
<213> ORGANISM: Artificial Sequence
<220> FEATURE:
<223> OTHER INFORMATION: Synthetic oligonucleotide: ZK1-LR

<400> SEQUENCE: 300
gctgggtcat gggcccatca                                          20

<210> SEQ ID NO 301
<211> LENGTH: 23
<212> TYPE: DNA
<213> ORGANISM: Artificial Sequence
<220> FEATURE:
<223> OTHER INFORMATION: Synthetic oligonucleotide: ZK2-F3

<400> SEQUENCE: 301
cttgactatg aataacaagc act                                      23

<210> SEQ ID NO 302

```
<211> LENGTH: 20
<212> TYPE: DNA
<213> ORGANISM: Artificial Sequence
<220> FEATURE:
<223> OTHER INFORMATION: Synthetic oligonucleotide: ZK2-R3

<400> SEQUENCE: 302
aagtggccag aggacagcct                                          20

<210> SEQ ID NO 303
<211> LENGTH: 44
<212> TYPE: DNA
<213> ORGANISM: Artificial Sequence
<220> FEATURE:
<223> OTHER INFORMATION: Synthetic oligonucleotide: ZK2-FIP

<400> SEQUENCE: 303
tccttgaact ctaccagtgc ttttgacatt ccattacctt ggca               44

<210> SEQ ID NO 304
<211> LENGTH: 44
<212> TYPE: DNA
<213> ORGANISM: Artificial Sequence
<220> FEATURE:
<223> OTHER INFORMATION: Synthetic oligonucleotide: ZK2-RIP

<400> SEQUENCE: 304
ggcaaactgt cgtggttcta tttttcagcc tccagagctc cagc               44

<210> SEQ ID NO 305
<211> LENGTH: 20
<212> TYPE: DNA
<213> ORGANISM: Artificial Sequence
<220> FEATURE:
<223> OTHER INFORMATION: Synthetic oligonucleotide: ZK2-LF

<400> SEQUENCE: 305
gtggagttcc ggtgtctgcc                                          20

<210> SEQ ID NO 306
<211> LENGTH: 20
<212> TYPE: DNA
<213> ORGANISM: Artificial Sequence
<220> FEATURE:
<223> OTHER INFORMATION: Synthetic oligonucleotide: ZK2-LR

<400> SEQUENCE: 306
ggagcagttc acacggccct                                          20
```

METHODS FOR REAL-TIME MULTIPLEX ISOTHERMAL DETECTION AND IDENTIFICATION OF BACTERIAL, VIRAL, AND PROTOZOAN NUCLEIC ACIDS

PRIORITY CLAIM

This patent application claims priority from U.S. Provisional application Ser. No. 62/158,664 filed on May 8, 2015, the contents of which are incorporated herein by reference.

SEQUENCE LISTING

The sequence listing contained in the electronic file "2016-05-01 1464.8005_ST25.txt" created on May 2, 2016, comprising 60 KB is incorporated herein by reference".

FIELD OF THE INVENTION

This disclosure relates to rapid methods for real-time multiplex detection and identification of human immunodeficiency virus, Ebola virus, Marburg virus, Yellow fever virus, hepatitis-B virus, Lassa fever virus, Plasmodium species, hepatitis-C virus, hepatitis-E virus, dengue virus, Chikungunya virus, Japanese Encephalitis virus, Middle Eastern Respiratory Syndrome Corona virus, Mycobacterium species, West Nile virus, Cytomegalovirus, Parvovirus, Leishmania species, Trypanosoma species and Zika virus nucleic acids, utilizing real-time quantitative isothermal amplification methods.

BACKGROUND OF THE INVENTION

Over the past several decades, humankind has been confronted with a plethora of infectious pathogens that present differential diagnostic challenges due to similar on-set clinical symptoms and lead to diseases that afflict millions of people globally. Clinicians and field health care workers have long desired portable diagnostic tools that rapidly provide multiple differential diagnostic data in order to implement targeted therapeutic intervention and monitor the trend of disease transmission through epidemiological surveillance. It is apparent that a need exists for a detection assay in fulfillment of this quest. Thus, several diagnostic tests including nucleic acid-based multiplex isothermal amplification methods have been developed and used to detect various pathogens. These detection formats, including some isothermal platforms, are rigid and inflexible and do not allow for rapid simultaneous detection and identification of pathogens. Also, such platforms hardly enable simultaneous quantitation of the pathogen load in an infected person. A further shortcoming of existing methods is their intermittent open-tube characteristic of performance that renders them prone to contamination. Therefore, the objective of this method is to provide a versatile and flexible pathogen detection platform that enables shuffling of detection components and real-time isothermal multiplexing for rapid detection, identification, and quantitation of bacteria, viruses, and protozoans, among other pathogens. A further object of this invention is to provide a commercially practicable detection method that is portable, inexpensive, and field-deployable. Furthermore, it is the objective of the present invention to provide a comparably sensitive and specific multiplexing detection system that will contribute to national and global public health safety; this would contribute to ensuring early diagnosis of multiple infectious diseases and simultaneous identification of their causative agents, thereby enabling timely therapeutic intervention as well as ensuring national and global public health security.

SUMMARY OF INVENTION

The need for a portable diagnostic tool for simultaneous detection of multiple pathogens cannot be overemphasized. Hence, a real-time multiplex, rapid, sensitive, and specific assay for simultaneous detection, identification, and quantification of pathogens has been developed namely, for human immunodeficiency virus (HIV), Ebola virus species (Zaire, Sudan, Tai-Forest, Reston, Bundibugyo), Marburg virus (MBV), Yellow fever virus (YFV), hepatitis-B virus (HBV), Lassa fever virus (LFV), Plasmodium species, hepatitis-C virus (HCV), hepatitis-E virus (HEV), dengue virus (DENV), Chikungunya virus (CHIKV), Japanese Encephalitis virus (JEV), Middle Eastern Respiratory Syndrome Corona virus (MERS CoV), Mycobacterium species (MTB), Severe Acute Respiratory Syndrome Corona virus (SARS CoV), West Nile (WNV) virus, Cytomegalovirus (CMV), Parvovirus (PAB19), Plasmodium species (PLM), Leishmania species (LE), Trypanosoma species (TRY), Zika virus (ZKV) and an array of other infectious pathogens. The assay is developed for laboratory as well as point-of-care and field epidemiological application so as to enable differential pathogen diagnosis, blood donor screening, early diagnosis of infections, and monitoring of therapeutic efficacy. This method contains procedures for detecting, differentiating and quantifying HIV, EBOV, MARV, HBV, HCV, CHIKV, MERS CoV, PAB19, CMV, JEV, TB, HEV, DENV, YFV, LFV, LE, MTB TRY, ZKV, and/or PLM in a biological sample, utilizing methods that include real-time (reverse transcription) and isothermal amplification (RT-LAMP). The method of this invention further includes a versatile and flexible platform that allows shuffling and organizing of detection components as duplex, triplex, multiplex, and/or "megaplex" isothermal assays for real-time quantitative detection, quantification, and identification of nucleic acids of multiple pathogens, and groups of phylogenetically related infectious organisms.

Also embodied in this method is the capability to distinguish different species, genotypes or serotypes of a pathogen. The method has been suitably employed to distinguish the major genotypes of hepatitis C virus (HCV) infection (FIG. 3) utilizing a single primer set.

Notably, this invention advances the art of nucleic acid amplification as it embodies a real-time procedure that shuffles reactions detection components, including multiple sets of pathogen-specific or gene-specific RT-LAMP oligonucleotides and a novel designed RT-LAMP fluorooligonucleotides of various fluorogenic chemistries. These oligonucleotides and fluorooligonucleotide sets within SEQ ID No 1-306 hybridize with the target nucleic acid in a closed-tube single-reaction mixture, rapidly amplifies the nucleic acids in real-time under isothermal mechanism, and simultaneously produce real-time detectable reaction signals (such as melt, amplification and/or dissociation curves) that are indicative of detection as well as used to identify and quantitate the following pathogens (HIV, EBOV, MARV, HBV, HCV, CHIKV, MERS CoV, PAB19, CMV, JEV, MTB, HEV, DENV, YFV, LFV, LE, ZKV, TRP, and/or PLM) and their species or subtypes in biological samples.

The oligonucleotides for detection of bacterial, viral, and parasitic (protozoan) nucleic acids by real-time multiplex RT-LAMP are herein disclosed and include primers for detection of HCV (such as SEQ ID NOs: 1-68), HBV nucleic acids (such as SEQ ID NOs: 69-86), HEV (such as SEQ ID NOs: 87-100), HIV nucleic acids (such as SEQ ID NOs: 101-112), WNV (such as SEQ ID NOs: 113-118), DENV (such as SEQ ID NOs: 119-130), CHIKV nucleic acids (such as SEQ ID NOs: 131-143), CMV nucleic acids (such as SEQ ID NOs: 144-150), PLM nucleic acids (such as SEQ ID NOs: 151-156), EBOV nucleic acids (such as SEQ ID NOs: 157-169), MARV (such as SEQ ID NOs: 170-175), YFV nucleic acids (such as SEQ ID NOs: 176-181), LE nucleic acids (such as SEQ ID NOs: 182-187), LFV nucleic acids (such as SEQ ID NOs: 188-209), MTB nucleic acids (such as SEQ ID NOs: 210-221), MERS CoV nucleic acids (such as SEQ ID NOs: 222-235), PAB19 nucleic acids (such as SEQ ID NOs: 236-246), JEV nucleic acids (such as SEQ ID NOs: 247-258), SARS CoV nucleic acid (such as SEQ ID NOs: 259-276), TRY nucleic acid (such as SEQ ID NOs: 277-294), and ZKV (such as SEQ ID NOs: 295-306) are herein provided. Diagnostic kits including one, two, three, or more sets of real-time RT-LAMP primers and novel fluorooligonucleotides are also herein disclosed.

According to the method of this invention, nucleic acid extracted from biological samples are amplified in real-time under defined isothermal conditions between about 40° C. and 70° C., utilizing a novel and special lysis-amplification solution or reaction buffer (herein referred to as the Lysis Reaction Buffer—LRB) on a portable real-time multichannel fluorospectrophotometric heating system or device that produces live test results in real-time within about 10 to 40 minutes.

This disclosure also embodies methods utilizing heat-treatment and novel lysis buffer-treatment of biological samples, sets of enzymes to facilitate strand displacement of nucleic acid and for hybridization of reporters/fluorophores, and substrate materials to directly amplify nucleic acid without further extraction of the nucleic acid. Results are read in real-time on a portable device and transmitted to a smartphone or an electronic tablet through wireless electronic application. The method of this invention provides that the detection-device will provide simple on-screen quantitative amplification graphs or curves in real time in the form of dissociation, amplification and or melting curves that correspond to pathogen-assigned fluorogenic detection of specific nucleic acid as well as provide quantitative pathogen load. Also provided by this method is the instant naked-eye visualization of test results by the fluorogenic colors emitted by each pathogen-specific or pathogen-assigned fluorogenic probes.

Herewith provided from the foregoing disclosure are detailed descriptions as depicted by the following figures.

BRIEF DESCRIPTION OF THE DRAWINGS AND FIGURES

A vivid understanding of the key features of the above summarized invention may be facilitated by the following figures and drawings which demonstrate the method and system of the invention. Although these figures and drawings understandably depict preferred embodiments of the invention, they should not be construed as limiting its scope with regard to other embodiments which the invention is capable of contemplating. Herein, some of the following figures and illustrations are submitted in color.

FIG. 1 shows a flow chart demonstrating a schematic procedure for pathogen detection, identification, quantitation, and approximate duration.

Figure 2:
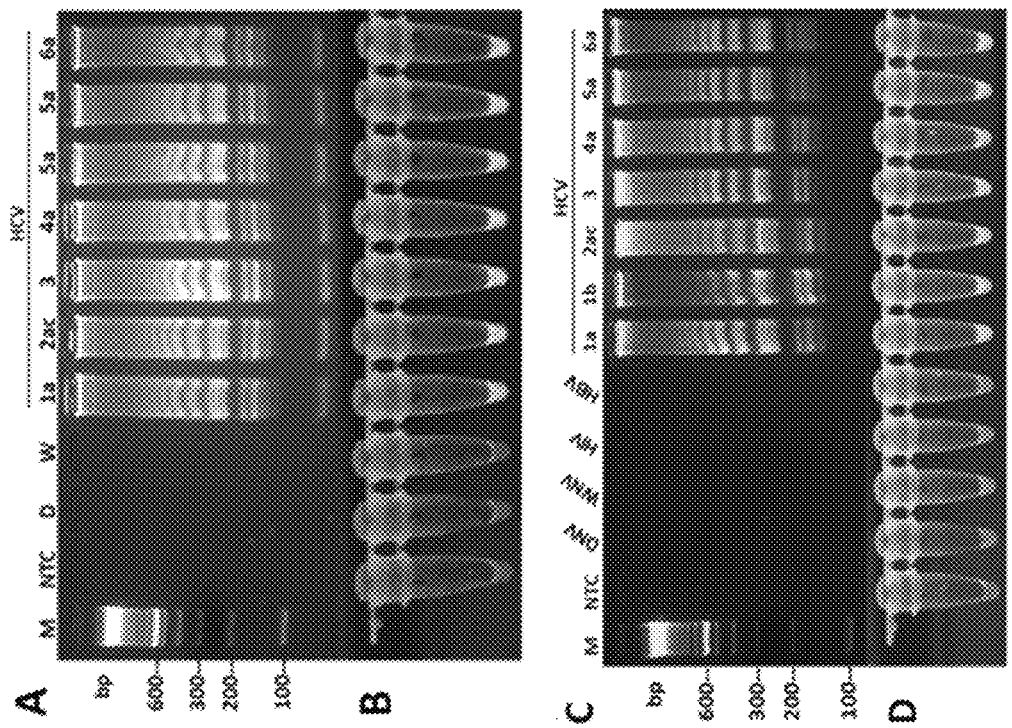

FIG. 2 is a digital image that demonstrates detection of HCV genotypes 1-6 (FIGS. 2A and 2C) detected with separate sets of universal oligonucleotides as shown by the presence of identical ladder-like banding patterns. Note the absence of ladder-like patterns in the no-template control (NTC), Dengue virus (D or DNV), West Nile virus (W or WNV), Human immunodeficiency virus (HIV), and Hepatitis B virus (HBV). M=100 bp marker. FIGS. 2B and 2D are UV-visualization of detected pathogens as demonstrated by intense fluorescence glow of DNA intercalating dye in hepatitis C virus (HCV) genotype 1-6, but not in the control samples.

Figure 3:
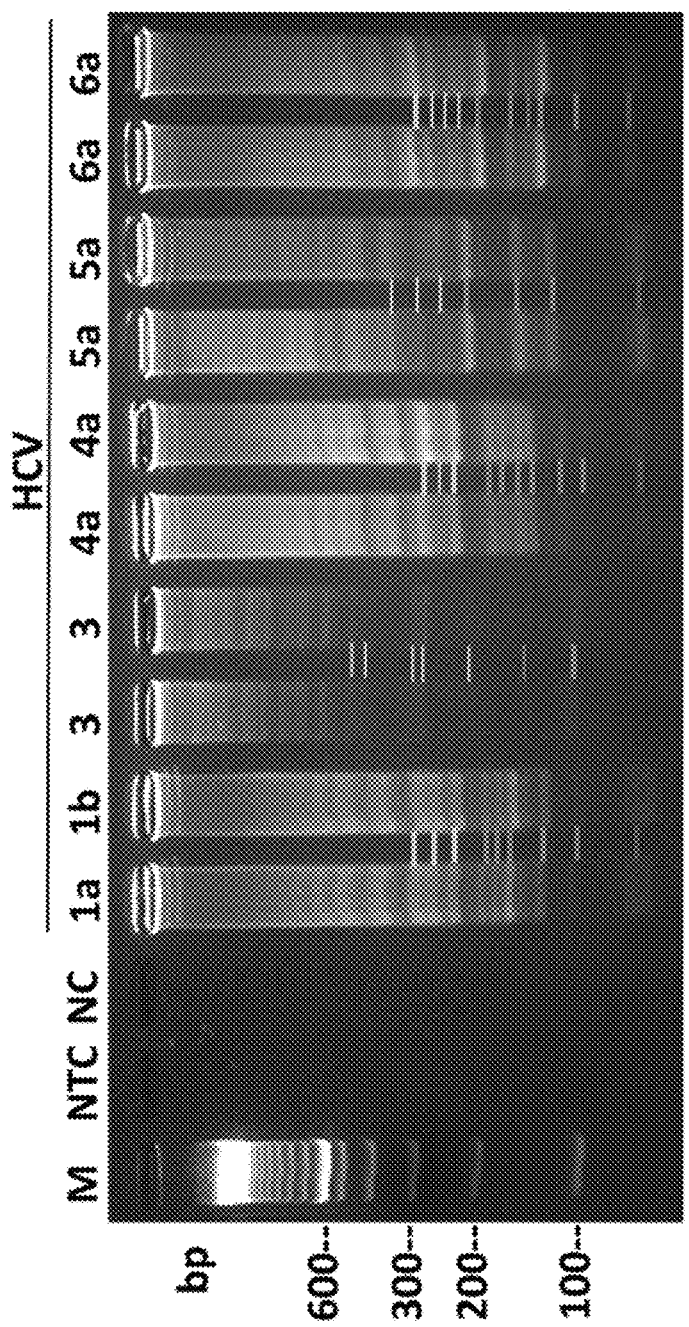

FIG. 3 is a digital image that shows detection and genotype identification of various hepatitis C virus (HCV) genotypes 1, 3, 4, 5, and 6 by a single primer-set and demonstrates distinct ladder-like banding patterns that are unique to each HCV genotype detected in duplicate and illustrated by color lines between the duplicates. Note that NTC=no-template control, NC=negative control plasma, and M=100 bp marker.

Figure 4:
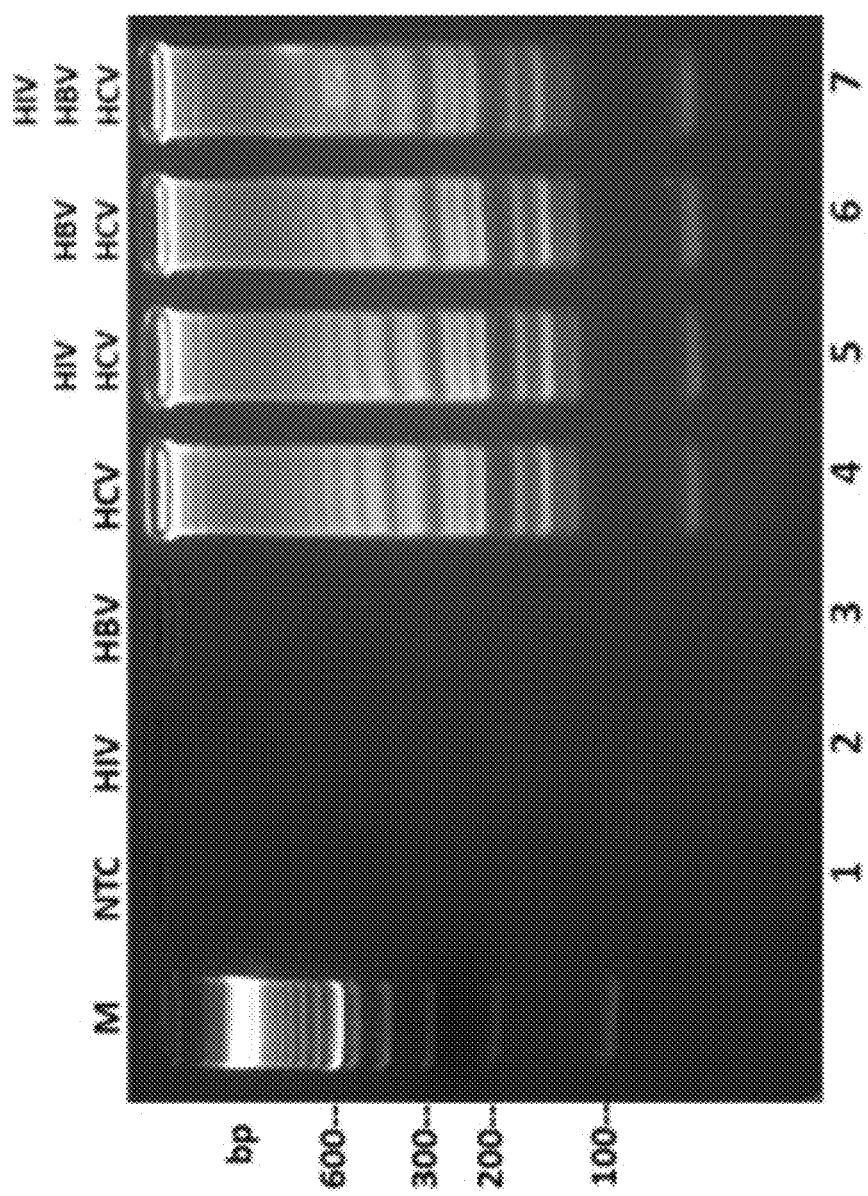

FIG. 4 is a digital image that demonstrates assay specificity of the HCV-specific primers and results of inhibition test performed. This figure shows detection of HCV-RNA in lanes 5-7 in the presence of HIV-RNA, HBV-DNA, and HIV-RNA alone or in combination; lanes 5-7 demonstrate HCV detection by the presence of ladder-like banding pattern which are similar to the HCV positive control in lane 4, and the absence of banding pattern in lanes 1-3. Note that NTC=no template control, HIV=human immunodeficiency virus ($10^6$ IU/rxn), HBV=hepatitis B virus ($10^5$ IU/rxn), HCV=hepatitis C virus ($10^3$ IU/rxn), M=100 bp marker.

Figure 5:
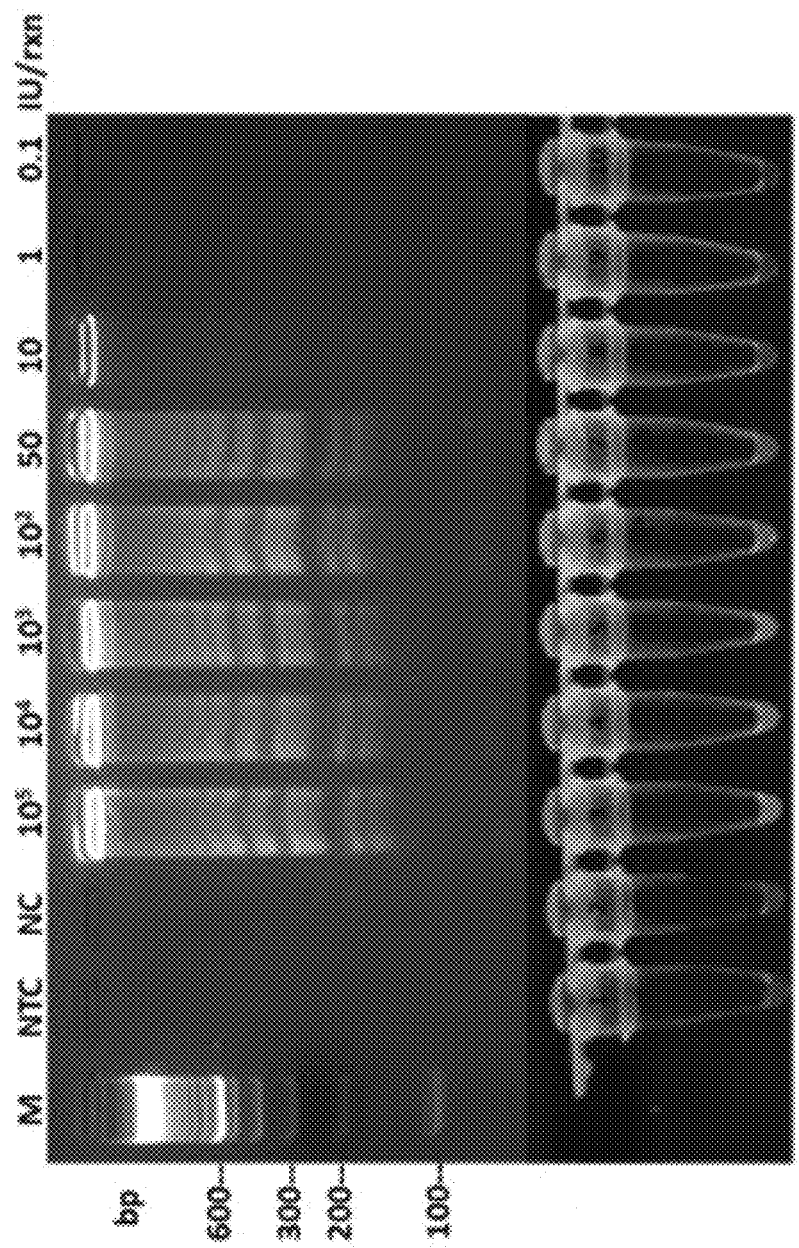

FIG. 5 is a digital image that shows detection sensitivity evaluated by serial dilution of HCV-RNA ($10^5$-0.1 IU/rxn). The assay detected down to 10 IU/rxn of RNA (lane 8) and demonstrated a fluorescence glow of DNA intercalating dye that is corresponding to the amount of nucleic acid detected (lanes 3-8). Note that NTC=no-template control, NC=negative plasma control, M=100 bp marker, and IU/rxn=International Unit per reaction.

Figure 6:
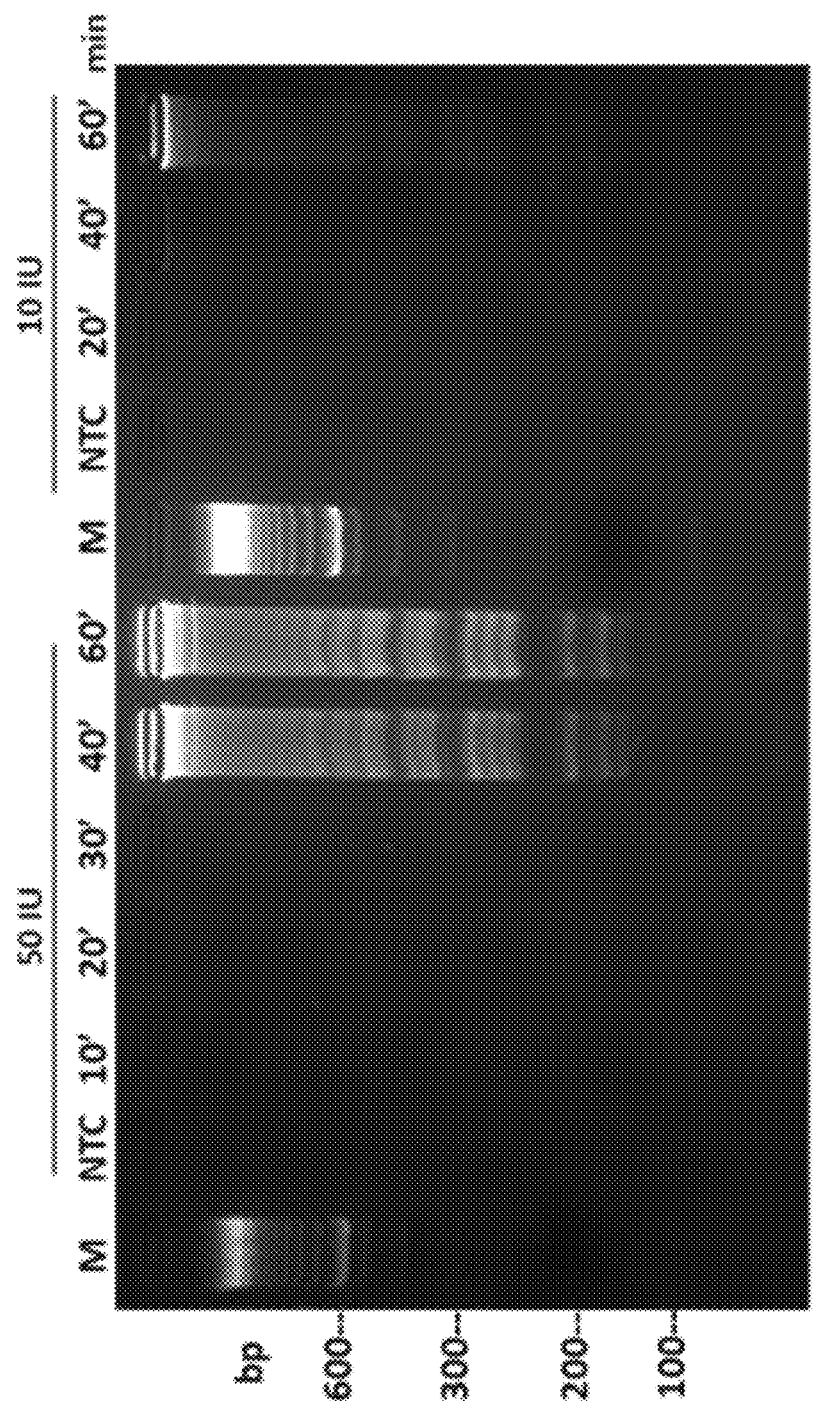

FIG. 6 is a digital image that shows time-course of detection and demonstrates the time point at which detection occurs. This was evaluated using 50 and 10 IU/rxn of HCV RNA at defined time points over a 60-minute reaction period. Electrophoretic analysis demonstrated detection of 50 IU of HCV-RNA at 40-minutes, while 10 IU/rxn of was detected at 60-minutes. Note that NTC=no-template control, M=100 bp marker, and IU/rxn=International Unit per reaction.

Figure 7:
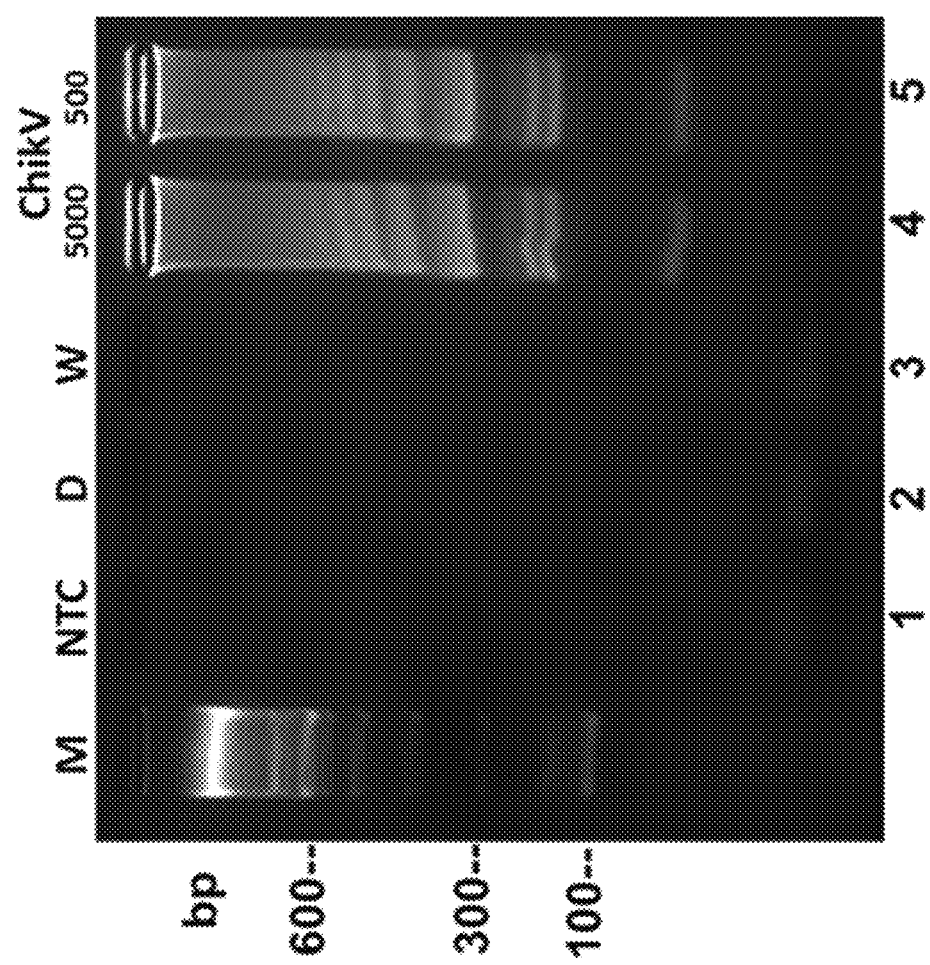

FIG. 7 demonstrates detection specificity and identification of Chikungunya virus (CHIKV) by isothermal amplification (lanes 4 and 5), using two dilutions (5000 and 500 copies per reaction); M=100 bp marker; NTC=non template control (lane 1); D=Dengue virus (lane 2); W=West Nile virus (lane 3).

Figure 8:
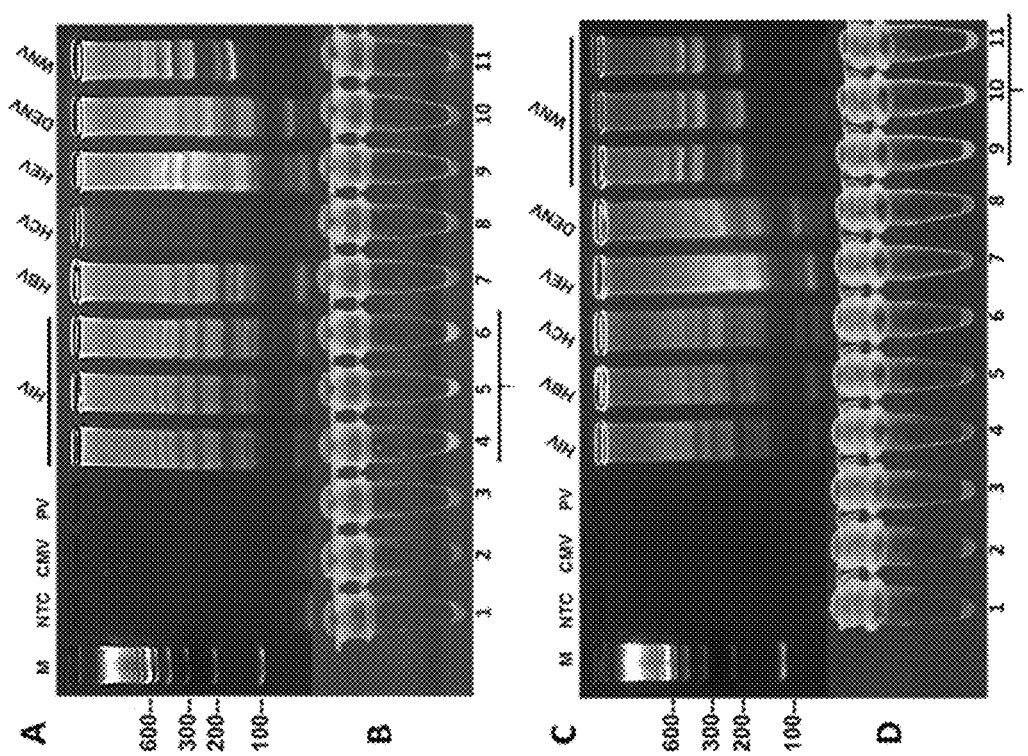

FIG. 8 are digital images that demonstrate the multiplex detection and specificity of the HIV pathogen-specific fluorogenic oligonucleotides that detect only HIV nucleic acid as seen in FIG. 8B (lanes 4 to 6 triplicate samples) with brighter fluorescence on naked-eye visualization of reaction tubes. As seen in lanes 4-11, all pathogens are detected on gel electrophoresis because of the presence of their specific primers in the multiplex reaction mixture. FIG. 8D demonstrates detection only of the triplicate West Nile virus (WNV) samples by the WNV-specific fluorooligonucleotide which is further demonstrated by a brighter fluorescence glow in the triplicate WNV samples in lanes 9, 10, and 11. Note: M=100 bp marker; NTC=non-template control; CMV=cytomegalovirus; PV=parvovirus; hepatitis-E virus (HEV); dengue virus (DENV); HCV=hepatitis C virus. The fluorooligonucleotides were labeled with 6-FAM (5') and BHQ1 (3').

Figure 9A:
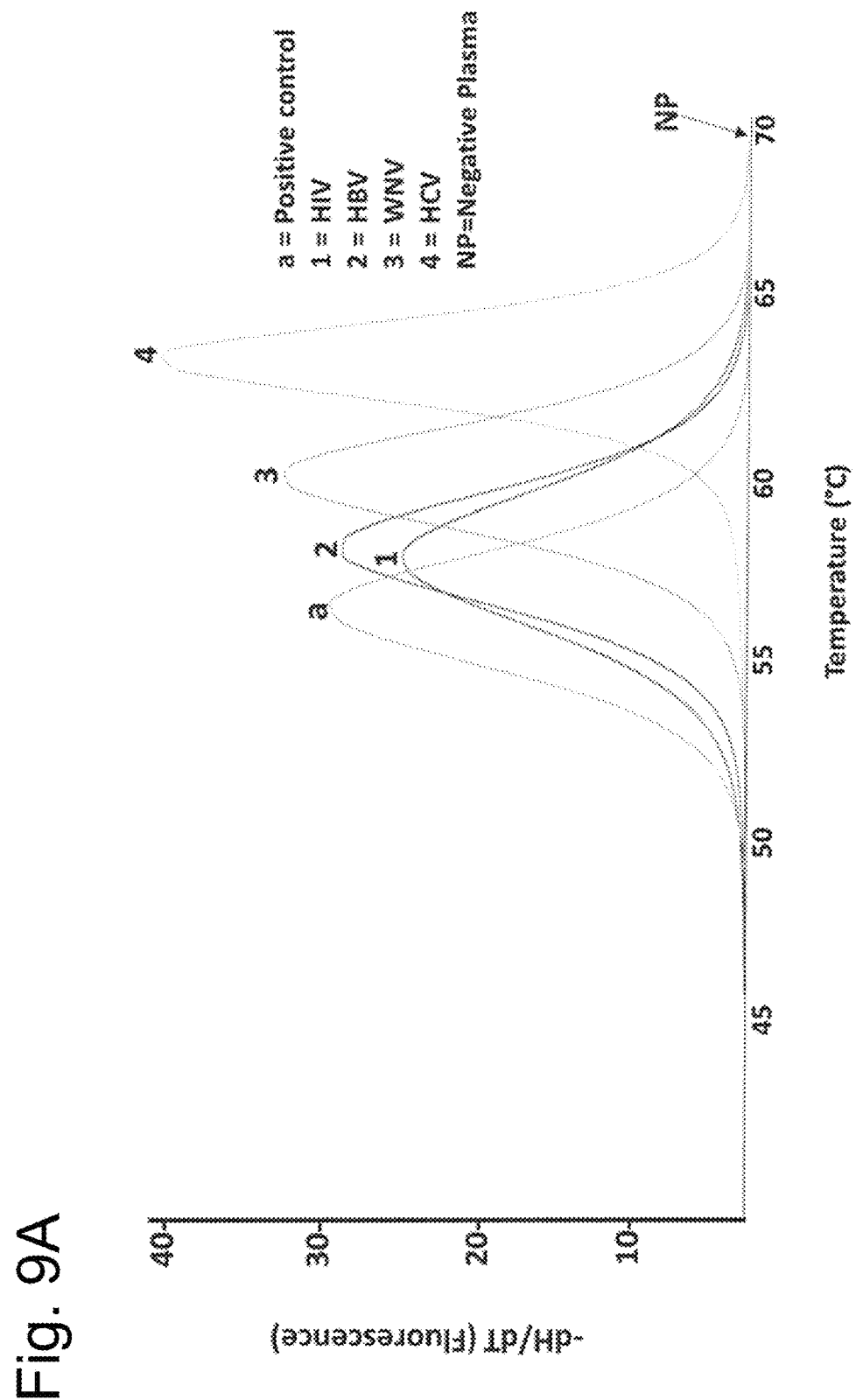
Figure 9B:
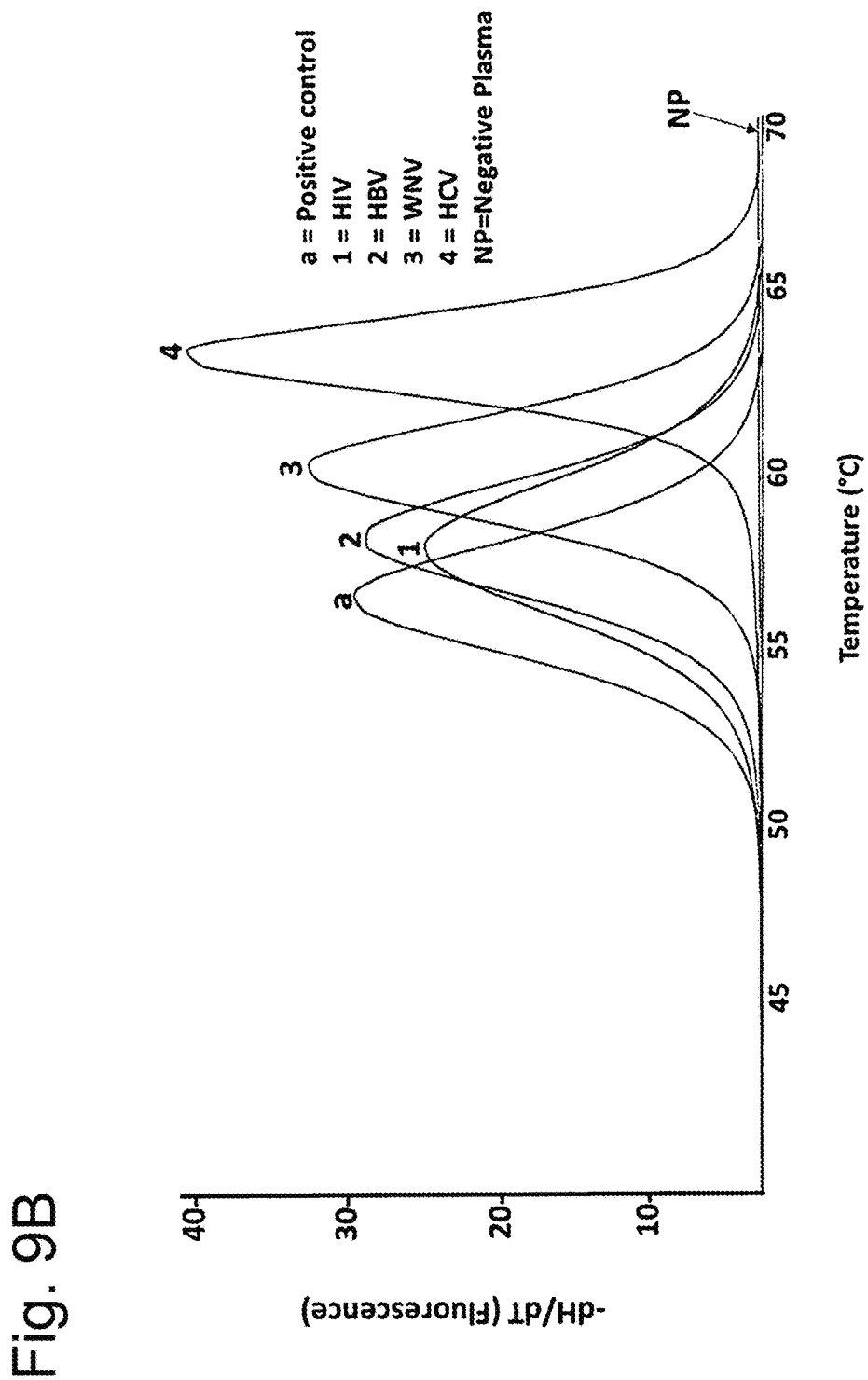
Figure 10A:
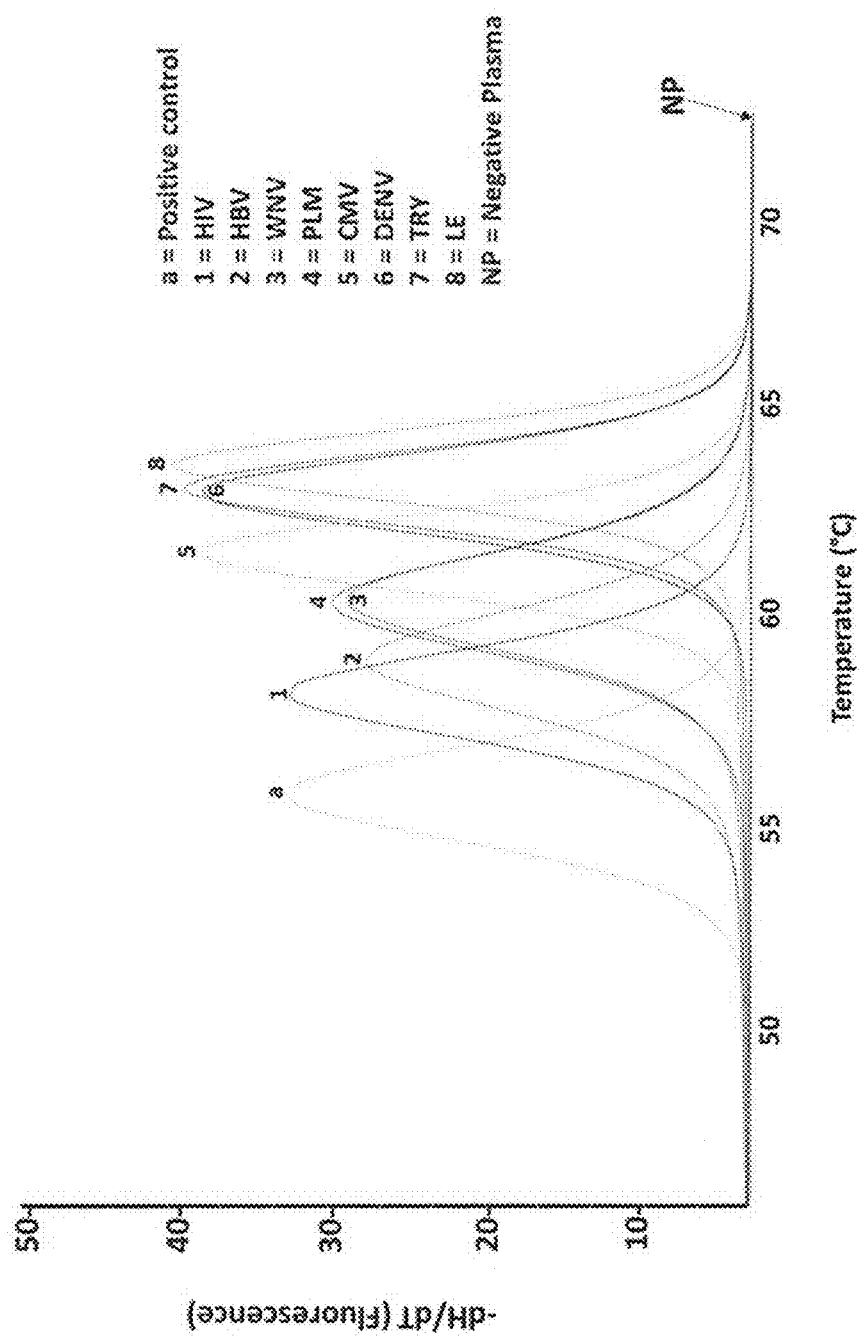
Figure 10B:
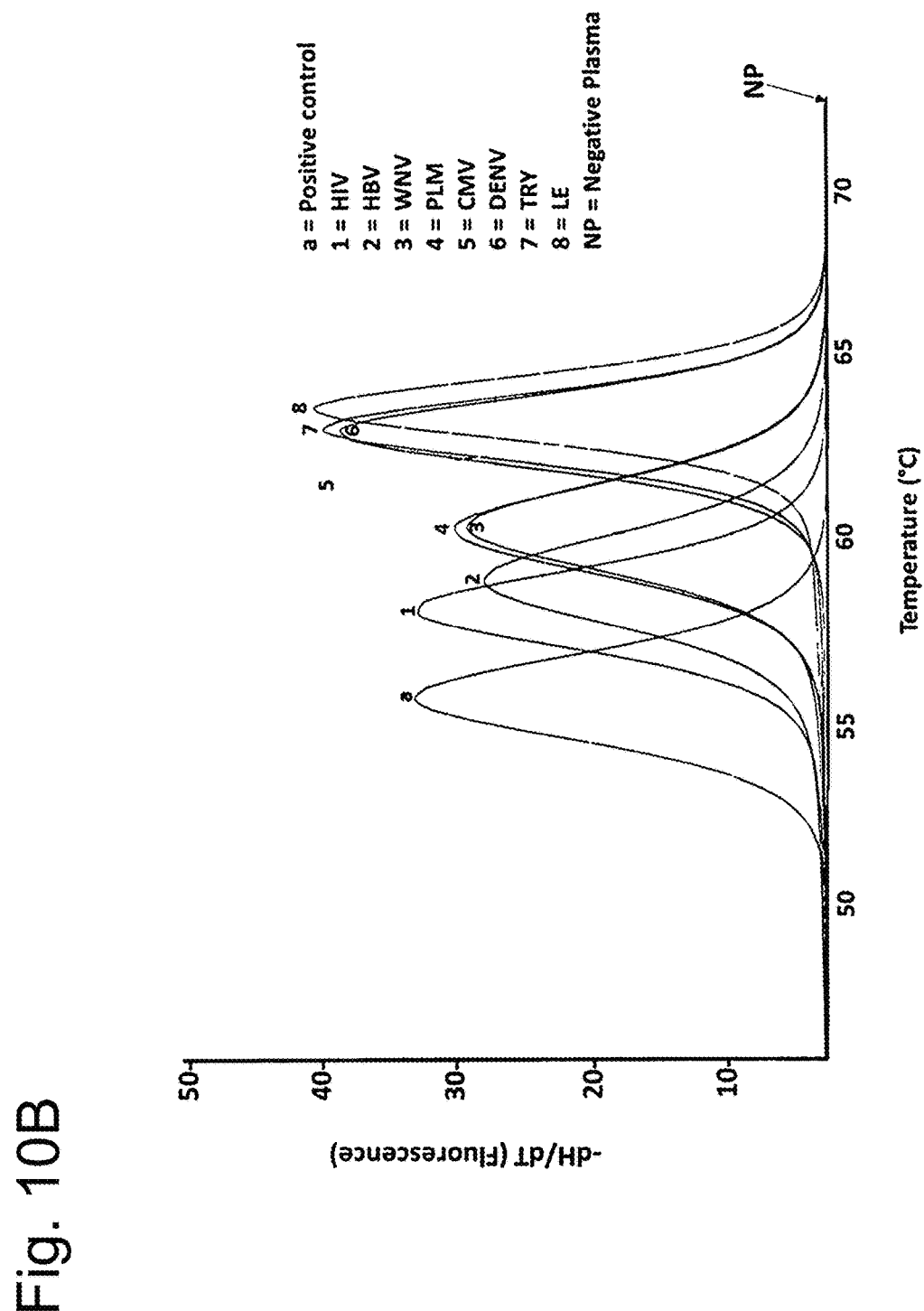
Figure 10C:
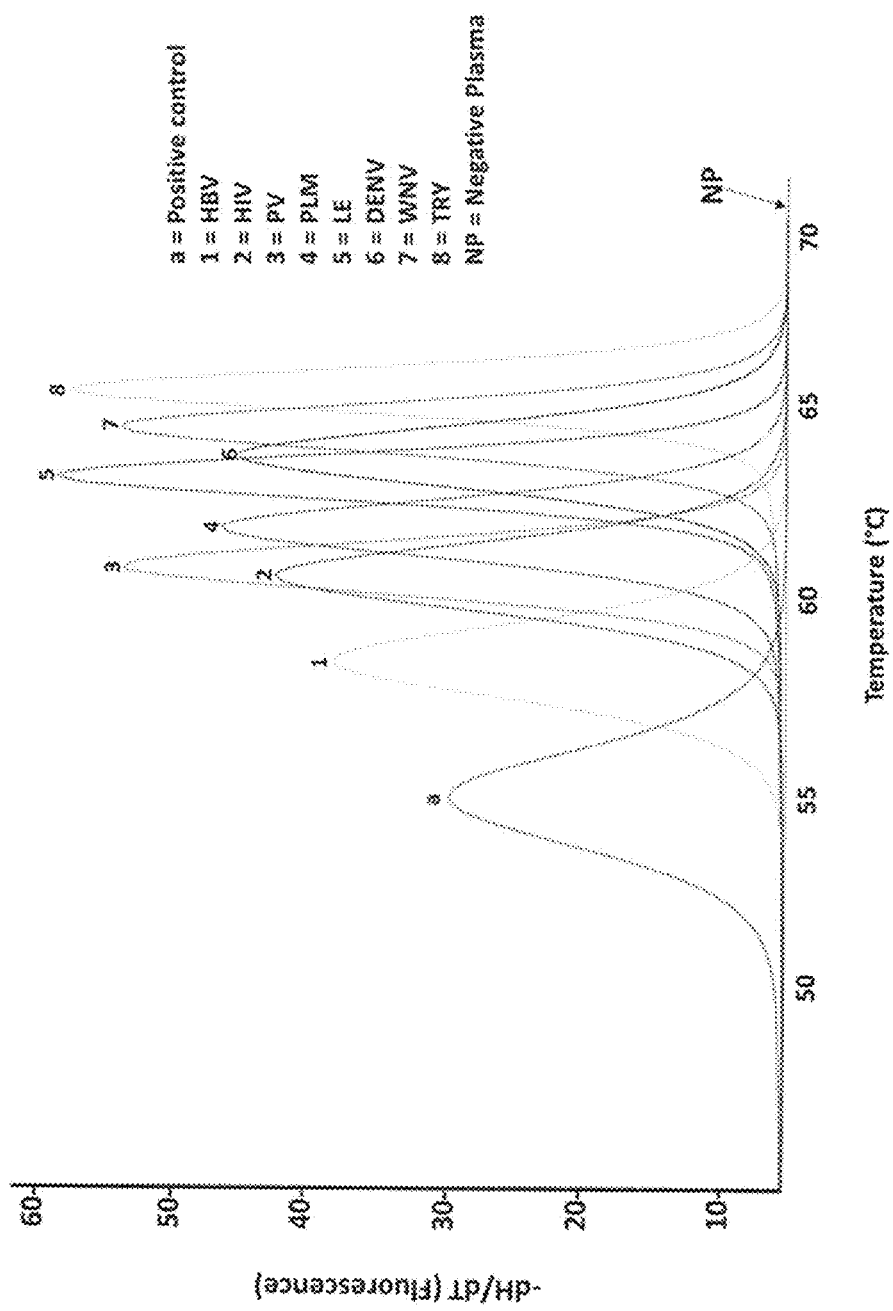
Figure 10D:
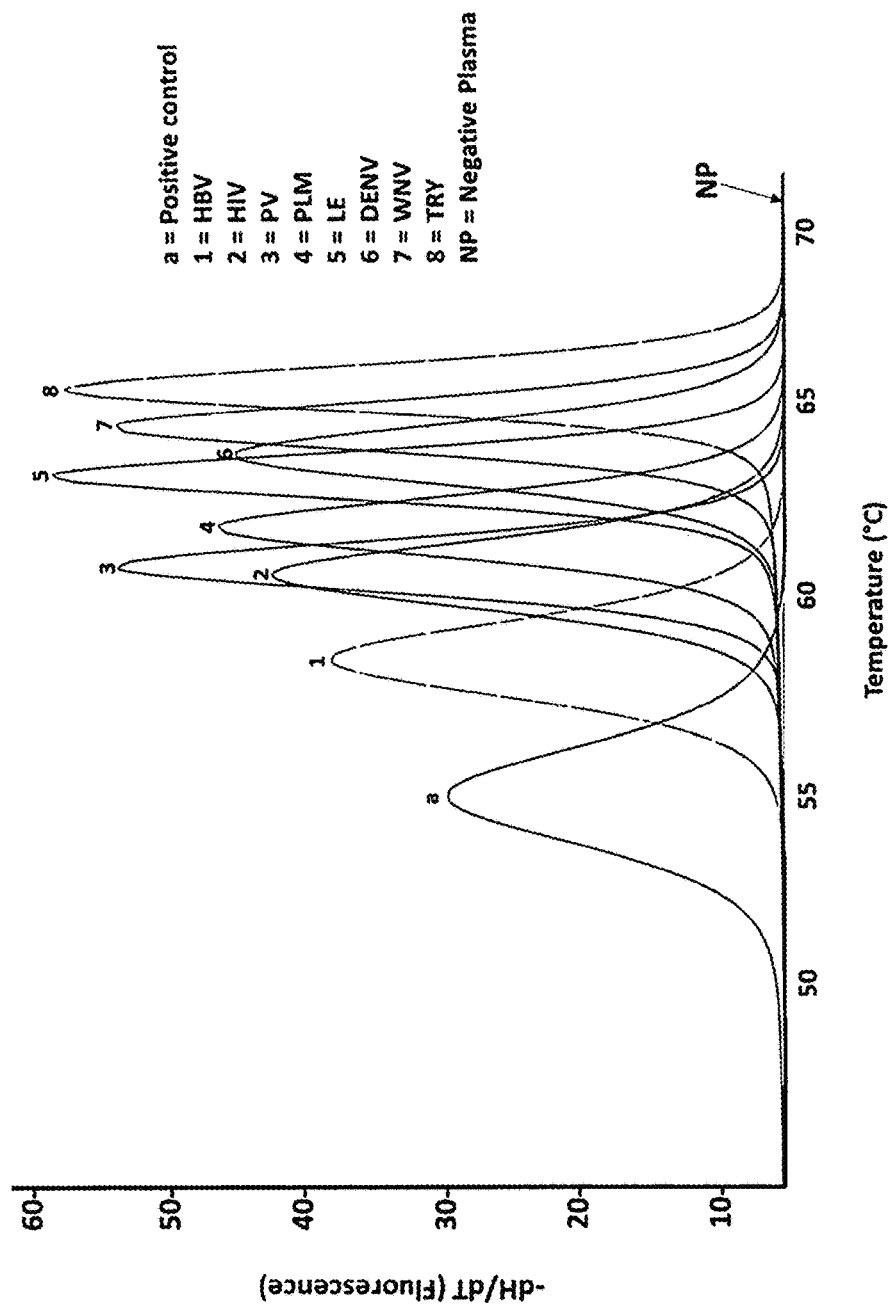

FIGS. 9A and FIG. 9B are illustrations of a real-time multiplex isothermal detection and simultaneous identification of four viral pathogens (HIV, HBV, WNV, and HCV) by their respective primers and specific fluorogenic oligonucleotides of each pathogen. This is shown by the real-time amplification dissociation curves of the respective pathogens. The amplification show the following: (a) internal positive control; (1) HIV=human Immunodeficiency virus; (2) HBV=hepatitis B virus; (3) WNV=West Nile virus; (4) HCV=hepatitis C virus; and NP=negative (healthy) human plasma).

FIGS. 10A, 10B, 10C and 10D Illustrate real-time multiplex isothermal detection and identification of pathogens (including HIV, HBV, WNV, PLM, CMV, DENV, TRY, PV, and LE) by their respective primers and specific fluorogenic oligonucleotides of each pathogen. This is shown by the real-time amplification dissociation curves of the respective pathogens. The amplification show detection of the following: (a) internal positive control; (1) HIV=human Immunodeficiency virus; (2) HBV=hepatitis B virus; (3) WNV=West Nile virus; (4) PLM=*Plasmodium* (malaria); (5) CMV=cytomegalovirus; (6) DENV=dengue virus; (7) TRY=*Trypanosoma*, (8) LE=*Leishmania*; PV=Parvovirus; and, NP=negative (healthy) human plasma.

Figure 11:
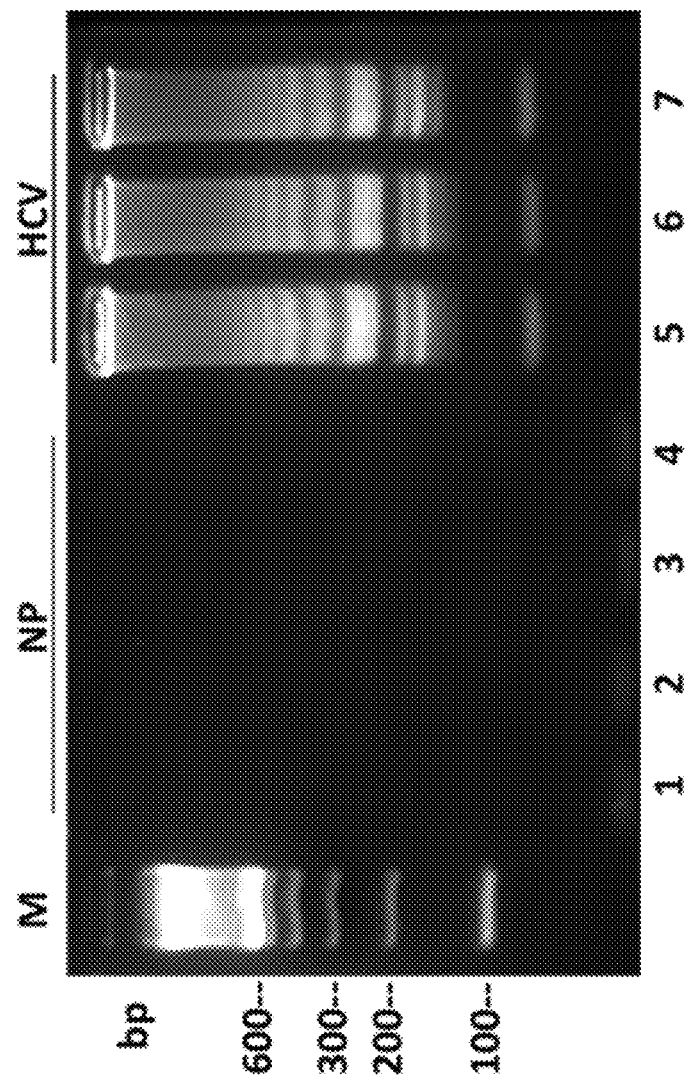

FIG. 11 Illustrates thermo-stability and amplification efficiency of the novel Lysis Reaction Buffer (LRB) after thermo-stressed stability test and used in real-time isothermal amplification after 12 months of room-temperature storage. Lanes 5-7 demonstrate amplification of HCV (hepatitis C virus); M=100 bp marker; and NP=negative (healthy human) plasma in lanes 1, 2, and 3.

Figure 12:
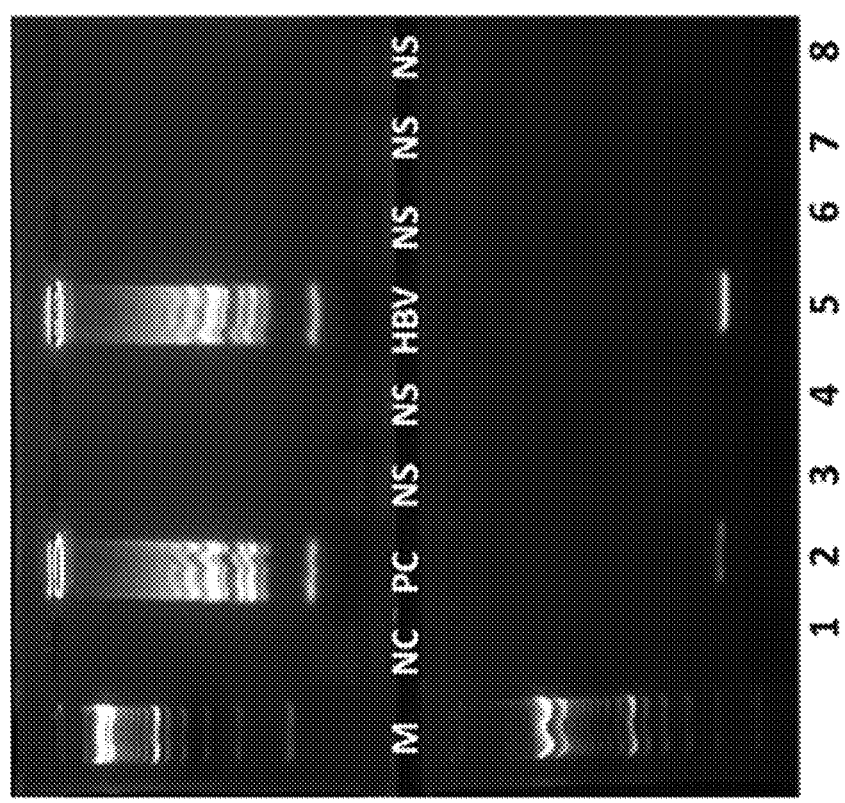

FIG. 12 is a digital image which demonstrates the multifaceted application and utility of the new Lysis Reaction Buffer (LRB) used for isothermal amplification in the top panel and for regular (RT) PCR reaction in the bottom panel to detect hepatitis B virus (HBV) in lane 5. Note that M=100 bp marker; NC=non-template control; PC=positive control HBV DNA; and, NS=negative sample.

Figure 13:
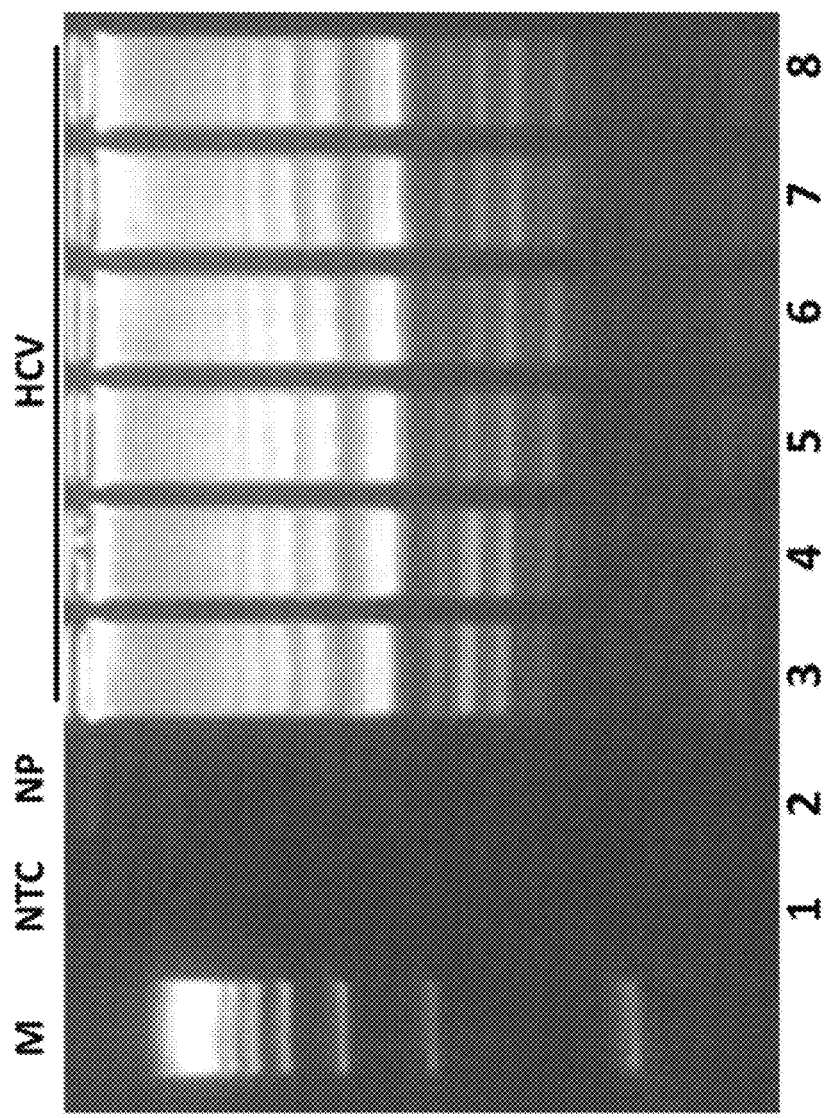

FIG. 13 is a digital image which shows efficient utility of the novel Lysis buffer. The lysis buffer was added to the HCV-infected plasma standards in a 1:3 ratio and incubated at room temperature for approximately 10 minutes. Then 10 µL of the resulting lysate was applied directly to the amplification mixture for detection of HCV RNA which is demonstrated by the presence of ladder-like banding patterns in lanes 3 to 8. Note that hepatitis C virus control (lane 3); M=100 bp marker; NTC=no-template control in lane 1; NP=negative sample (lane 2).

Figure 14:
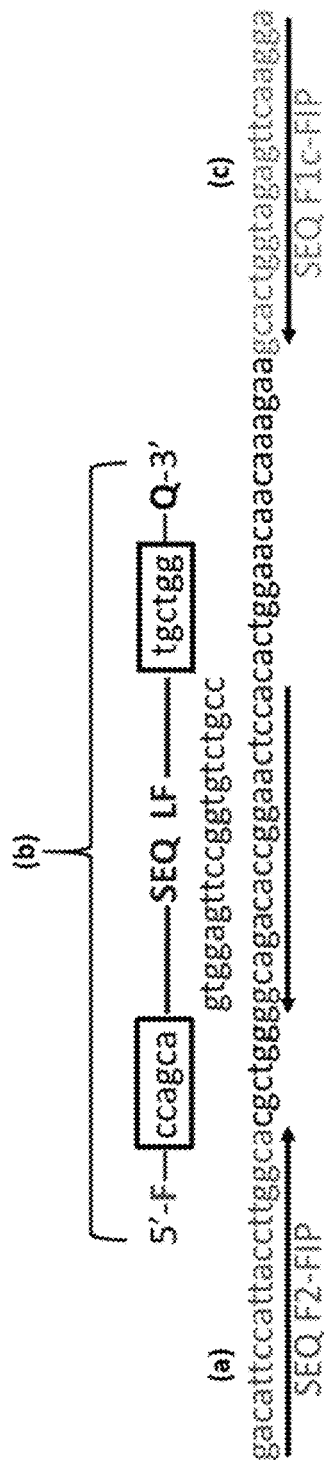

FIG. 14 illustrates the novel design of isothermal real time RT-LAMP fluorooligonucleotide of the F3, R3, LR, LF, FIP, and RIP. For example, the SEQ LF oligonucleotide is designed as bi-labeled loop-fluorescent-probe that is held in a hairpin-loop conformation by about 4-7 nucleotides long complementary stem-sequences at both 5'-3' ends (or vice versa) and tagged with desirable reporter-fluorophore or quencher. Fluorophores may including Cy5, Cy5.5, Cy3, 6-carboxyfluorescein (6-Fam), tetrachlorofluorescein (Tet), or Texas-Red or other desirable reporter dyes, while quenchers may include Tamara, DABCYL, black hole quencher-1, 2, and 3 (BHQ1, 2, and 3) or other desirable quenchers. FIG. 14 also illustrates a probe hybridized to its target nucleic acid strand, wherein florescence is emitting and utilized for detection and identification of pathogen a well as quantitation of pathogen burden. (a)=F2 position of target nucleotide on gene sequence; (b)=nucleotide sequence of fluorooligonucleotide comprising of a fluorophore (F) held by the boxed complementary stem-sequences at the 5'-terminus, while a quencher (Q) is held by another boxed complementary stem-sequence at the 3'-terminus; (c)=position of the F1c portion of the FIP primer as illustrated on the 5' non-coding region of the Zika virus (ZKV) gene.

OLIGONUCLEOTIDE SEQUENCES

Any nucleic acid and amino acid sequences herein listed are shown using standard letter abbreviations for nucleotide bases and amino acids. In some cases, only one strand of each nucleic acid sequence is shown, while the complementary strand is understood as included by any reference to the displayed strand.

SEQ ID NOs: 1-68 are nucleic acid sequences of exemplary HCV RT-LAMP primers.
SEQ ID NOs: 69-86 are nucleic acid sequences of exemplary HBV LAMP primers.
SEQ ID NOs: 87-100 are nucleic acid sequences of exemplary HEV RT-LAMP primers.
SEQ ID NOs: 101-112 are nucleic acid sequences of exemplary HIV RT-LAMP primers.
SEQ ID NOs: 113-118 are nucleic acid sequences of exemplary WNV RT-LAMP primers.
SEQ ID NOs: 119-130 are nucleic acid sequences of exemplary DENV RT-LAMP primers.
SEQ ID NOs: 131-143 are nucleic acid sequences of exemplary CHIKV RT-LAMP primers.
SEQ ID NOs: 144-150 are nucleic acid sequences of exemplary CMV LAMP primers.
SEQ ID NOs: 151-156 are nucleic acid sequences of exemplary PLM LAMP primers.
SEQ ID NOs: 157-169 are nucleic acid sequences of exemplary EBOV RT-LAMP primers.
SEQ ID NOs: 170-175 are nucleic acid sequences of exemplary MARV RT-LAMP primers.
SEQ ID NOs: 176-181 are nucleic acid sequences of exemplary YFV RT-LAMP primers.
SEQ ID NOs: 182-187 are nucleic acid sequences of exemplary LE LAMP primers.
SEQ ID NOs: 188-209 are nucleic acid sequences of exemplary LFV RT-LAMP primers.
SEQ ID NOs: 210-221 are nucleic acid sequences of exemplary MTB LAMP primers.
SEQ ID NOs: 222-235 are nucleic acid sequences of exemplary MERS CoV RT-LAMP primers.
SEQ ID NOs: 236-246 are nucleic acid sequences of exemplary PAB19 RT-LAMP primers.
SEQ ID NOs: 247-258 are nucleic acid sequences of exemplary JEV RT-LAMP primers.
SEQ ID NOs: 259-276 are nucleic acid sequences of exemplary SARS CoV RT-LAMP primers.
SEQ ID NOs: 277-294 are nucleic acid sequences of exemplary TRY RT-LAMP primers.
SEQ ID NOs: 295-306 are nucleic acid sequences of exemplary ZKV RT-LAMP primers.

DETAILED DESCRIPTION OF THE INVENTION

I. Abbreviations

CHIKV Chikunguya virus
CMV cytomegalovirus
DENV Dengue virus

HBV hepatitis B virus
HCV hepatitis C virus
HEV hepatitis E virus
HIV human immunodeficiency virus
EBOV Ebola virus
F Fluorophore
IU international units
JEV Japanese encephalitis virus
LAMP loop-mediated isothermal amplification
LFV Lassa fever virus
LE *Leishmania*
NCR non-coding region
MARV Marburg virus
MERS CoV Middle Eastern Respiratory Syndrome Corona virus
MTB *mycobacterium tuberculosis*
PAB19 Parvovirus B19
PLM *plasmodium*
Q quencher
RFU relative fluorescence units
RT reverse transcriptase
(RT)-LAMP (reverse transcription)-loop-mediated isothermal amplification
SARS CoV Severe Acute Respiratory Syndrome Coronavirus
TRY *Trypanosoma*
UV ultraviolet
WNV West Nile virus
YFV Yellow fever virus
ZKV Zika virus II. Definitions Technical terminologies used herein are conventionally employed parlance in the field of molecular biology and amplification technology. These terms and methods provide a clearer description of the present disclosure and a guidance for those of ordinary skill in the art to practice the present disclosure. Publications, patent applications, patents, and/or other references mentioned herein are incorporated by reference for all purposes. Sequences associated with GenBank Accession Nos. mentioned herein are incorporated by reference as were present on Apr. 27, 2015, to the extent permissible by applicable rules and/or law. Although methods and materials similar or equivalent to those described herein can be used to practice or test the disclosed technology, suitable methods and materials containing specifics are described below. The materials, methods, and examples are illustrative only and not intended to be limiting. In order to facilitate review of the various embodiments of this disclosure, the following explanations of specific terminologies are provided:

Amplification: Is an exponential increase in the number of copies of a nucleic acid molecule, such as a gene or fragment of a gene, for example at least a portion of an HIV, HBV, HCV, DENV, CHIKV or WNV nucleic acid molecule. The products of an amplification reaction are called amplicons or amplification products. Amplification may be represented by a graphed curved such as dissociation curves or by bands (banding-pattern) on gel electrophoresis. For gene analysis or diagnostic purposes, amplification of nucleic acids from biological samples is performed in vitro utilizing techniques such as the polymerase chain reaction (PCR), real-time PCR, quantitative real-time PCR (qPCR), reverse transcription PCR (RT-PCR), quantitative RT-PCR (qRT-PCR), and loop-mediated isothermal amplification (LAMP; see Notomi et al., *Nucl. Acids Res.* 28:e63, 2000); reverse-transcriptase LAMP (RT-LAMP); and strand displacement amplification (see U.S. Pat. No. 5,744,311), among others. Common to these techniques is a process by which a sample (containing nucleic acid) is hybridized with primers. Under defined thermocyclic or isothermal condition, amplification occurs through strand displacement of template, primers annealing, and extension, thus resulting to an exponential production of millions of copies of a piece of nucleic acid.

CHIKV: Chikungunya virus (CHIKV) was first isolated following an outbreak in Tanzania in the 1950s (Ross. *J Hyg (Loud)*, 54:177-191, 1956). CHIKV infection typically induced an acute onset of painful syndrome as characterized by polyarthralgia, fever, asthenia, headache, myalgia and skin rashes. CHIKV is an enveloped virus that possesses a single stranded, positive-sense RNA genome of 12 kilobases. CHIKV is transmitted by the *Aedes* mosquito, with *Aedes aegypti* and *Aedes albopictus* as the main vectors, while humans serve as host. Its mortality rate is rather low, but the epidemic potential of the virus is fearful due to the prolonged morbidity and the rapid spread of the virus. In 2004, the virus managed to claim global attention when it re-emerged and began spreading around the world. Exemplary CHIKV sequences include GenBank Accession Nos. FN295487, HQ846358, JF274082, and HW249780 which are incorporated by reference herein as present in GenBank on Apr. 27, 2015. Additional CHIKV species sequences can be identified by one skilled in the art.

CMV: Cytomegalovirus (CMV) is a leading cause of opportunistic infection causing substantial morbidity and mortality in transplant patients (Dummer et al., *J. Infect. Dis.* 152, 1182-1191, 1985) and HIV-infected patients who are immunocompromised (Drew, 1996). As a member of the family Herpesviridae, CMV establishes latency upon primary infection which occurs early in life in a majority of individuals (Britt and Alford, 1996). CMV can also cause asymptomatic infection. Exemplary CMV sequences include GenBank Accession Nos. BK000394, FJ527563, FJ491277, and FJ616285 which are incorporated by reference herein as present in GenBank on Apr. 27, 2015. Additional CMV species sequences can be identified by one skilled in the art.

Dengue virus (DENV): Dengue virus (DENV) is member of the family Flaviridae and is transmitted by the mosquito vector, *Aedes aegypti*. There are 4 different serotypes of the virus, namely, DENV-1, DENV-2, DENV-3, and DENV-4. It is estimated that yearly over 300 million people are infected with DENV. DENV infection causes dengue fever or dengue hemorrhagic fever (DHF) with symptoms including high fever, severe headache, severe joint, muscle, and bone pain, rash persistent vomiting, severe abdominal pain, and hemorrhagic manifestations such as ascites, pleural effusions, bleeding of internal organs or hemorrhagic shock. DENV nucleic acid and protein sequences are available in public databases, including GenBank. Examples of DENV sequences include GenBank Accession Nos. KM204119, AF180817, and KJ438296 (DEN-1); KP012546 and KC762677 (DEN-2); KJ643590, KF954949, and KF954946 (DEN-3); and KJ160504 and KJ160504 (DEN-4), all of which are incorporated by reference as included in GenBank on Apr. 27, 2015. Additional DENV species sequences can be identified by one skilled in the art.

Detectable labels: These are detectable compounds such as fluorophores, radioactive isotopes, fluorescein, etc., that are conjugated to another molecule to enable detection, identification, and quantitation of said molecules. For example, nucleic acids are labeled for various purposes and several methods are available for facilitating the labeling of nucleic acids (Marras. *Methods Mol Biol,* 335: 3-16, 2006; Sambrook and Russell, in *Molecular Cloning: A Laboratory Manual,* 3$^{rd}$ Ed., Cold Spring Harbor Laboratory Press (2001).

Ebola virus (EBOV): Ebola viruses (EBOV) causes Ebola Virus Disease (EVD), a severe haemorrhagic fever that is characterized by a high case-fatality rate around 50-90%. EBOV is an enveloped, non-segmented, RNA negative stranded virus of the family of Filoviridae. The viral genome, approximately 19 kilobases long, contains seven genes transcribed by the complex of the RNA-dependent RNA polymerase (L and VP35 proteins). Ebola virus was first discovered in 1976 in northern Zaire (now the Democratic Republic of Congo) and southern Sudan. There are 5 EBOV species known to date: (ZEBOV, emerged first in Zaire) and Sudan ebola virus (SUDV), discovered in 1976; Reston ebola virus (RESTV), discovered in 1989; Taï Forest virus (TAFV), discovered in 1994; and Bundibugyo virus (BDBV), discovered in 2007 (Feldmann and Geisbert, *The Lancet.* 377:849-862, 2011). Four Ebola virus species, ZEBOV, SUDV, TAFV, and BDBV, are known to be pathogenic in humans. The virus is zoonotic and is transmitted to humans from animals. Fruit bats are probable virus reservoir (Leroy et al., *Nature.* 438:575-576, 2005). EBOV nucleic acid and protein sequences are available in public databases, including GenBank. Exemplary EBOV sequences include GenBank Accession Nos. NC002549 and KM233049 (ZEBOV), EU338380 (SUDV), AF522874 (RESTV), NC014372 (TAFV), KC545396 (BUDBV), which are incorporated by reference herein as present in GenBank on Apr. 27, 2015. Additional EBOV species sequences can be identified by one skilled in the art.

Fluorophore: A fluorophore is a fluorescent chemical compound that can re-emit light upon light excitation of a specific wavelength. These compounds are used alone, as a tracer-molecules in fluids, as a dye for staining of certain cellular structures, as a substrate of enzymes, or as a probe or indicator for detecting nucleic acids. Employed in confocal microscopy, immunohistochemistry, and nucleic acid amplification methods, fluorophores are also part of the larger class of luminescent compounds (Liu et al., "Fluorophores and Their Applications as Molecular Probes in Living Cells", *Curr. Org. Chem.* 17: 564-579, 2013). Fluorophores can be attached to nucleic acid sequences either as "donor" or "acceptor" and may function on the biochemical mechanism of fluorescence energy transfer to emit, quench the fluorescence of other fluorescent dyes or to relay their fluorescence at much longer wavelengths. The acceptor fluorophores absorb energy from donor fluorophores within wavelength spanning between about 300 to approximately 900 nm. The following are examples of fluorophores that can be used in the probes and primers disclosed herein and are known to those skilled in the: acridine and acridine isothiocyanate, 4-amino-N-[3-vinylsulfonyl)phenyl]naphthalimide-3,5 disulfonate (Lucifer Yellow VS); Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); ethidium; -fluorescein and derivatives such as 5-carboxyfluorescein (FAM), 2'7'-dimethoxy-4'5'-dichloro-6-carboxyfluorescein (JOE), fluorescein, 6-carboxy-fluorescein (HEX), and TET (tetramethyl fluorescein); Phenol Red; rhodamine and derivatives such as 6-carboxy-X-rhodamine (ROX), rhodamine (Rhod), rhodamine B, rhodamine 123, rhodamine X isothiocyanate, N,N,N',N'-tetramethyl-6-carboxyrhodamine (TAMRA); sulforhodamine B; sulforhodamine 101 and sulfonyl chloride derivative of sulforhodamine 101 (Texas Red); LightCycler Red 640; Cy5.5; and Cy56-carboxyfluorescein; other fluorophores include Cy3; Cy5, VIC (from Applied Biosystems); LC Red 640; LC Red 705; and Quasar® 570, Quasar® 670, CalRed 590, CalRed 610, CalRed 615, CalRed 635, CalGreen 520, CalGold 540, and CalOrange 560 (from Biosearch Technologies, Novato, Calif.). One skilled in the art can select additional fluorophores from commercial vendors such as Integrated DNA Technologies (Coralville, Iowa) and Molecular Probes or Life Technologies (Carlsbad, Calif.). In a particular example, the following acceptor fluorophores can be attached to nucleic to quench or diminish the emission of a reporter fluorophore: Dabcyl, QSY7, and QSY33 (from Molecular Probes), Black Hole Quenchers™ such as BHQ1, BHQ2, and BHQ3, Eclipse™ Dark Quencher (from Epoch Biosciences), or Iowa Black™ (Integrated DNA Technologies Hepatitis B virus (HBV): HBV is a DNA virus with a circular genome of partially double-stranded DNA that is a member of the family Hepadnaviridae. HBV causes acute disease, characterized by liver inflammation, vomiting, and jaundice, as well as chronic infection which may lead to cirrhosis or hepatocellular carcinoma. There are eight genotypes of HBV (A-H). HBV-A is most commonly found in the Americas, Africa, India, and Western Europe, HBV-B and HBV-C are most commonly found in Asia and the United States and HBV-D most commonly found in Southern Europe, India, and the United States. The HBV genotypes differ by at least 8% of their sequence across the genome (Okamoto et al., *J. Gen. Virol.* 69:2575-2583, 1988). HBV nucleic acid and protein sequences are available in public databases, including GenBank. Exemplary HBV sequences include GenBank Accession No. AB116094 (HBV-A), AF121247 (HBV-B), AB670304 (HBV-C), AB090269 (HBV-D), HM363603 (HBV-E), AB036912 (HBV-F), JX849644 (HBV-G), and AP007261 (HBV-H), all of which are incorporated by reference herein as present in GenBank on Apr. 27, 2015. Additional HBV species sequences can be identified by one skilled in the art.

Hepatitis C virus (HCV): Hepatitis C virus (HCV) is a single-stranded RNA virus of the Flaviviradae family and there are 7 major genotypes with 67 subtypes found in different regions of the world (Smith et al., *Hepatology.* 59: 318-327, 2014; Moratorio et al., *Virol J.* 4: 79, 2007). Transmitted through modes such as injection drug use (IDU), unsafe injections, needle-stick, and mother-to-fetal, infection with HCV may be asymptomatic for several years and lead to chronic-active hepatitis and hepatocellular carcinoma (Ghany et al., *Hepatology.* 4: 1335-1374, 2009). Approximately 170 million people globally are infected with HCV. According to the US Centers for Disease Control and Prevention (CDC), about 3.2 million people are infected with HCV in the United States, wherein HCV genotypes 1 and 2 account for majority of infections. Progression of HCV-induced liver damage and response to antiviral therapy is genotype dependent as HCV genotypes 1b is associated with severe liver disease than other genotype. HCV nucleic acid and protein sequences are available in public databases, including GenBank. Exemplary HCV sequences include GenBank Accession Nos. AF009606 and AF333324 (HCV-1), D00944 (HCV-2), and HQ228207 (HCV-3), JX227959 (HCV-4), Y13184 (HCV-5), DQ480524 (HCV-6) all of which are incorporated by reference herein as present in GenBank on Apr. 27, 2015. Additional HCV species sequences can be identified by one skilled in the art.

Hepatitis E virus (HEV): HEV is a small, single-stranded, non-enveloped RNA hepatotropic virus currently classified in the genus Hepevirus (Purcell et al., *J Hepatol.* 48:494-503, 2008). HEV is transmitted via the faecal-oral route and may be blood-borne. At higher risk of infection with HEV are immunocompromised individuals and organ transplant recipients. HEV causes outbreaks that have been linked to waterborne sources in developing countries in the Northern and Central regions of Africa, South and Central America and Southeast Asia. HEV infection which was thought to be imported in the developed countries is otherwise demonstrated to be prevalent in the United States, Europe and Japan (Dong et al., *J Clin Microbiol.* 49:4164-4172, 2011). There are four genotypes of HEV (genotypes 1-4), some of which infect only humans, animals, or both. Genotypes 1 and 2 infect humans, but genotypes 3 and 4 infect humans and animals, predominantly pigs, thereby demonstrating zoonotic and cross-species transmission (Mushahwar et al., *J. Med Virol,* 2008). HEV nucleic acid and protein sequences are available in public databases, including GenBank. Exemplary HEV sequences include GenBank Accession No. AF010126 (HEV-1), M74506 (HEV-2), AF060668 and HQ389543 (HEV-3), and GU206557 (HEV-4) and are incorporated by reference herein as present in GenBank on Apr. 27, 2015. Additional HEV species sequences can be identified by one skilled in the art.

Human immunodeficiency virus (HIV): The human immunodeficiency virus (HIV) is a lentivirus, a subgroup of retrovirus that causes the acquired immunodeficiency syndrome (AIDS). HIV is composed of two copies of positive single-stranded RNA that codes for genes enclosed by a conical capsid (Weiss. *Science,* 260: 1273-1279, 1993). The virus has two types, namely HIV-1 and HIV-2. HIV is transmitted through transfusion of blood, semen, vaginal fluid, pre-ejaculate, or breast milk of an infected person. The virus primarily infects and depletes the CD4+ T-cells and other cells of the immune system (Sigal et al., *Nature* 477: 95-98, 2011). HIV/AIDS engenders a condition in humans that is characterized by the progressive failure of the immune system and allows life-threatening opportunistic infections (the AIDS related complexes—ARC) and some forms of cancers (e.g. Kaposi sarcoma, non-Hodgkin lymphoma, and cervical cancer) (Fischl et al., *N Engl J Med.* 317:185-191, 1987; Friedman-Kien. *J. Am. Acad. Dermatol.* 5: 468-471, 1981). HIV infection is diagnosed by means of serological methods such as Western blot which detects antibody to the viral proteins and nucleic acid test such as RT-PCR which detects viral RNA in blood (Chou et al., *Annals of Internal Medicine* 143: 55-73, 2005). To date, about 31 antiretroviral drugs (ARVs) are approved by the US Food and Drug Administration to treat HIV infection. While there is no cure for HIV/AIDS infection, the antiviral treatments suppress the virus, even to undetectable levels, thus enabling infected persons to lead healthier and longer lives. Nucleic acid and protein sequences of HIV are available in public GenBank and the HIV Database at the Los Alamos National Laboratory (www.hiv.lanl.gov/). Exemplary sequences in GenBank include the following: KF735874, EU541617, and JN248357 (HIV-1); X05291, AF208027, M30502, and DQ307022 (HIV-2). Additional HIV species sequences can be identified by one skilled in the art.

Hybridize: Hybridization is a phenomenon in molecular biology, in which single-stranded deoxyribonucleic acid (DNA) or ribonucleic acid (RNA) molecules anneal to complementary DNA or RNA under controlled temperature conditions. These strands are complementary to each other as in the case of nucleic acid amplification reaction in which primers and probes are utilized.

Isolate: A biochemical process by which nucleic acid (e.g. genomic DNA, total RNA or micro-RNA) are separated and purified from biological samples such as blood components. An "isolated" biological component (such as a nucleic acid) has been substantially separated or purified away from other biological components in which the component naturally occurs, such as other chromosomal and extrachromosomal DNA, RNA, and proteins. Utilizing various methods of purification (silica-based columns, or phenol-chloroform) methods, isolated nucleic acids may be up to 99.9% pure.

Japanese encephalitis virus (JEV): JEV is a mosquito-borne flavivirus known to be endemic in Asia, extending to India and Pakistan in the west, where it is a leading cause of non-bacterial encephalitis. JEVcauses an estimated annual number of 30,000-50,000 cases worldwide (Mackenzie et al. *Nat Med.* 10:S98-109, 2004). The majority of the infections are subclinical, but up to 30% of symptomatic patients die, and 30% of the survivors have persistent neurological sequelae. The life cycle of JEV includes *Culex* mosquitoes and water birds or pigs, but JEV also infects a wide range of other vertebrates. In addition to humans, horses may develop encephalitis and are considered dead-end hosts for JEV transmission. JEV sequences include GenBank Accession Nos.: JF706284, JN711459, JF706285, and AF080251, all of which are incorporated by reference as included in GenBank on Apr. 27, 2015. Additional JEV species sequences can be identified by one skilled in the art.

*Leishmania* (LE): Leishmaniasis is a parasitic disease affecting millions of people mainly on the Indian Subcontinent It is the main cause of cutaneous Leishmaniasis (CL) and visceral leishmaniasis (VL) in the Old World. Parasites are transmitted by Phlebotominae sandflies after blood-feeding on infected mammalian hosts. CL is widely spread in the developing world, affecting people in 88 countries with 1.5 million new cases reported each year (Alvar et al., *PLoS One.* 7:e35671, 2012; Desjeux. *Comp Immunol Microbiol Infect Dis.* 27: 305-318, 2004). CL usually produces ulcers on the exposed parts of the body that often leave disfiguring scars, which in turn, can cause serious social prejudice. Visceral leishmaniasis (VL) is considered as one of the most neglected tropical diseases. On the Indian sub-continent, VL is mainly caused by the intracellular protozoan parasite *Leishmania donovani* and transmitted exclusively by the bite of the sandfly, *Phlebotomous argentipes*. The annual incidence worldwide is approximately 0.2 to 0.4 million cases with over 60% of the world's VL cases occurring in India, Bangladesh and Nepal (*WHO: Regional Technical Advisory Group on Kala-azar Elimination. Report of the first meeting*, Manesar, Haryana, 20-23 Dec. 2004. New Delhi: WHO Regional Office for South-East Asia; 2005). LE sequences include GenBank Accession Nos.: GQ332356, AF308685, KJ417491, and AB678350, all of which are incorporated by reference as included in GenBank on Apr. 12, 2015. Additional LE species sequences can be identified by one skilled in the art.

Lassa fever virus (LFV): Lassa fever, a viral hemorrhagic fever, is caused by the Lassa virus. The disease is endemic to a large region of West Africa, where 100,000-300,000 cases have been estimated to occur yearly (McCormick et al., *J Infect Dis.* 155:445-455, 1987). More than 20 cases have been imported to the United States, Canada, United Kingdom and Japan since 1969, when the disease was first recognized (Macher and Wolfe. *Emerg Infect Dis,* 12:835-837, 2006). The viral hemorrhagic fever reportedly has a 69% case fatality rate in hospitalized patients. LAV sequences include GenBank Accession Nos.:KM821843, HQ688672, and GU481073, all of which are incorporated by reference as included in GenBank on Apr. 12, 2015. Additional LAV species sequences can be identified by one skilled in the art.

Loop-mediated isothermal amplification (LAMP): A one temperature DNA amplification method that utilizes two or three pairs of primers, DNA strand displacement enzymes to catalyze the reaction. The method is a single-step amplification reaction utilizing a DNA polymerase with strand displacement activity (e.g., Notomi et al., *Nucl. Acids. Res.* 28:E63, 2000; Nagamine et al., *Mol. Cell. Probes* 16:223-229, 2002; Mori et al., *J Biochem. Biophys. Methods* 59:145-157, 2004). The amplification reaction produces a stem-loop DNA with multiple inverted repeats of the target nucleic acid sequence. Reverse transcriptase can be added to the reaction for amplification of RNA target sequences, a process referred to as RT-LAMP.

Marburg virus (MARV): Marburg fever is a viral hemorrhagic illness caused by the Marburg virus. The virus was first isolated in Marburg, Germany in 1967 after which several outbreaks have been reported in the Democratic Republic of the Congo and Angola (Slenczka and Klenk, *Journ of Infect Dis.* 196:S131-135, 2007; Towner et al., *J Virol.* 80:6497-6516, 2006) with case fatality rates approaching 90%. Travelers visiting Uganda have also imported the virus into the Netherlands and the United States (Timen. *Emerg Infect Dis.* 15:1171-1175, 2009; Fujita et al., *MMWR Morb Mortal Wkly Rep,* 58:1377-1381, 2009). MARV sequences include GenBank Accession Nos.: KP117261, KC545388, JX458851, FJ750959, and DQ447658, all of which are incorporated by reference as included in GenBank on Apr. 27, 2015. Additional MARV species sequences can be identified by one skilled in the art.

Middle East respiratory syndrome coronavirus (MERS CoV): Middle East respiratory syndrome coronavirus (MERS-CoV) is a viral infection characterized by history of fever, cough, expectoration, and shortness of breath. It is a Coronavirus that was initially identified from a 60-year-old Saudi man who was admitted to a private hospital in Jeddah on Jun. 13, 2012 (Zaki et al., *N Engl J Med.* 367:1814-1820, 2012). Since the initial description, a total of 834 laboratory-confirmed cases of infection with MERS-CoV including 288 (34.5%) deaths were reported to the World Health Organization (WHO). MERS-CoV sequences include GenBank Accession Nos.: KF600647 and KF917527, both of which are incorporated by reference as included in GenBank on Apr. 12, 2015. Additional MERS-CoV species sequences can be identified by one skilled in the art.

Parvovirus B19 (PAB19): Parvovirus B19 (B19V), is the causative agent of erythema infectiosum, otherwise known as the "fifth disease". It may be present in blood and in plasma products, infect blood recipients, and cause severe disease (Dodd. *Transfusion.* 51:1878-1879, 2011). B19V is a small non-enveloped single-stranded-DNA genome (length 5-6 kb) of the Parvoviridae family. Based on isolates having nucleotide divergence greater than about 10%, three B19V genotypes have been identified. Genotype 1 is the most prevalent type and circulates worldwide and is the B19V prototype. Genotype 2 viruses are found in plasma donations from Europe and North America. Genotype 3 has been found predominantly in West Africa (Ghana), but has also been found in samples from Europe, Asia, and South America, mainly Brazil (Candotti et al. *J Virol.* November; 78:12169-12178, 2004). PAVB19 sequences include GenBank Accession Nos.: AB126271, DQ234779, and AY582125 which are incorporated by reference as included in GenBank on Apr. 12, 2015. Additional PABV19 species sequences can be identified by one skilled in the art.

*Plasmodium* (PLM): *Plasmodium* is a parasitic protozoan that causes malaria infection. Several *Plasmodium* species (*malariae, vivax, ovale*, and *falciparum*) infect humans and other animals, and are transmitted by mosquitoes of the *Anopheles* genus. Malaria infection occurs around the world especially in Africa, Asia, and South America (Alexandre et al., *Emerg Infect Dis.* 16:1611-1614, 2010; Camara et al., *Malar J.* 14:60, 015; Upadhyayula, et al., *PLoS One.* 10: e0119514, 2015). PLM sequences include GenBank Accession Nos.: HQ283210, HQ283218, KF696372, and KJ170107 which are incorporated by reference as included in GenBank on Apr. 27, 2015. Additional PLM species sequences can be identified by one skilled in the art.

Primer: A primer is a strand of short nucleic acid sequences (generally about 10, 20, 40 or more base pairs) that serves as a starting point for DNA synthesis or cDNA synthesis from RNA. This biochemical process occurs during amplification or replication.

Probe: A probe is a complementary nucleic sequences of about 10 or more nucleotides long and to which fluorophores or other detectable molecules are attached.

SARS CoV: Severe acute respiratory syndrome Coronavirus (SARS CoV) is an emerging infectious disease that has affected many countries since it was first discovered in Asia in 2003 (WHO. *Wkly Epidemiol Rec;* 78:73-74, 2003). SARS CoV, which is transmitted through coughing out of respiratory droplets, is genetically related to the coronaviruses that are characterized by the presence of a single-stranded positive-sense RNA genome of about 30 kb in length (Marra et al., *Science.* 300:1399-1404, 2003; Drosten et al., *N Engl J Med.* 348:1967-1976, 2003). During the 2003 outbreak, SARS spread across five continents and had a cumulative total of 8464 cases and 799 deaths by May that year. SARS CoV sequences include GenBank Accession Nos.: FJ950407, AY545919, JX163925, and DQ497008 which are incorporated by reference as included in GenBank on Apr. 27, 2015. Additional SARS CoV species sequences can be identified by one skilled in the art.

Sample: A biological specimen that contains nucleic acids such as genomic DNA, complementary DNA), messenger RNA total RNA, small inhibitory RNA, etc. Samples could be specimens such as blood components, sputum, urine, vomitus, tissues, organs, and cells among others.

"Shufflex": A term describing a procedure whereby assay reagents such as (fluoro)-oligonucleotides and reaction components are flexibly arrange, rearranged, or shuffled around, and formulated to detect, identify, and quantitate a group of pathogens that are either phylogenically related or present similar clinical symptoms.

Subject: Any multi-cellular vertebrate organism, such as human and non-human mammals (including non-human primates). In one example, a subject is known to be or is suspected of being infected with one or more viruses, bacteria, and/or parasites.

*Trypanosoma* (TRY): *Trypanosoma* is the etiological agent of American and African trypanosomiasis. There are several known species among which *Trypanasoma cruzi* (*T. cruzi*), *Trypanosoma bruecei* (*T. burcei*), *Trypanosoma gambiense* (*T. gambiense*), and *Trypanosoma rhodesiense* (*T. rhodesiense*) are the most common. For example, *T. cruzi*, found in the Americas, is the cause of Chagas' disease, which affects approximately 16 to 18 million people in 21 countries in Central and South America. As a result of human migration from Latin America, the disease has spread to the United States and Canada, and as far as Europe and Australia in recent years. (Schmunis. *Mem Inst Oswaldo Cruz.* 102 Suppl 1:75-85, 2007). *Trypanosoma* is transmitted through insect bites to humans and other animals, with *T. burcei, T. gambiense,* and *T. rhodesiense* causing sleeping sickness Africa.

*Mycobacterium Tuberculosis* (MTB): Tuberculosis (TB), caused by *Mycobacterium* species is one of the leading causes of death worldwide. According to the World Health Organization (WHO), approximately 9 million people developed TB in 2013 and about 1.5 million died from the disease (WHO. *Global tuberculosis report* 2014, 2014). TB is transmitted by human-to-human or animal (*Mycobacterium bovis* which infects animals) contact through inhalation of contaminated droplets released from the lungs of an infected person. The WHO estimated that 3.5% of new and 20.5% of previously treated cases were multidrug-resistant strains of *Mycobacterium tuberculosis* (MDR-TB). Hence, irrespective of evidence that TB is slowly declining, the emergence and spread of multidrug-resistant strains of *Mycobacterium tuberculosis* represents a major public health challenge to the global control of the disease. MTB sequences include GenBank Accession Nos.: AL123456, AP010918, CP010873, and BX248333 which are incorporated by reference as included in GenBank on Apr. 27, 2015. Additional MTB species sequences can be identified by one skilled in the art.

West Nile virus (WNV): WNV is an RNA virus of the Flaviviridae family and is related to other important human pathogens, including dengue viruses, yellow fever viruses, and Japanese encephalitis viruses. WNV is an enveloped single-stranded, positive sense virus of an approximately 11-kb RNA genome. This flavivirus has emerged as a significant cause of viral encephalitis globally. WNV is transmitted by mosquitoes and infects humans and causes diseases in other animals including horses (Hayes et al., *Emerg Infect Dis* 0.11:1167-1173, 2005). Infection of humans is associated with a febrile illness that can progress to a lethal encephalitis (Sejvar et al., *JAMA.* 290:511-530, 2003). Epidemiological documentations show that outbreaks of WNV fever and encephalitis have occurred in regions throughout the world in the Middle East, Europe, and Africa, the United States, Mexico, South America, and the Caribbean (Dauphin et al., *Comp Immunol Microbiol Infect Dis.* 27:343-355, 2004; Komar and Clark. *Rev. Panam. Salud Publica.* 19:112-117, 2006; Lanciotti et al., *Science* 286:2333-2337, 1999). Although vaccines are available for animal use, no vaccines or specific therapies for WNV are currently approved for humans. Nucleic acid and protein sequences of are available in public databases, including GenBank Accession Nos.: AY646354, JN183893, AF202541, KF234080, JF95718, and JQ928174, all of which are incorporated by reference as included in GenBank on Apr. 27, 2015. One of skill in the art can identify additional WNV sequences.

Yellow Fever Virus (YFV): Yellow fever is a vector-borne disease affecting humans and non-human primates in tropical areas of Africa and South America and is caused by the yellow fever virus (YFV) (Monath. *Lancet Infect Dis* 0.1: 11-20, 2001). YFV which belongs to the family Flaviviridae. Infection with YFV is characterized by symptoms ranging from mild to hemorrhagic syndrome that can potentially lead to organ failure and fatal outcome. YFV sequences include GenBank Accession Nos.: AY640589, AY603338, and AY572535 which are incorporated by reference as included in GenBank on Apr. 27, 2015. Additional YFV species sequences can be identified by one skilled in the art.

Zika virus (ZKV): Zika virus disease (Zika) is a disease caused by the Zika virus, which is transmitted primarily through the bite of an infected *Aedes* species mosquito. The most common symptoms of ZKV are fever, rash, joint pain, and conjunctivitis (red/pink eyes) (Faye et al., *PLoS Negl Trop Dis* 8(1): e2636, 2014, doi:10.1371/journal.pntd.0002636). The illness is usually mild with symptoms lasting for several days to a week after being bitten by an infected mosquito. ZKV infection during pregnancy can cause a serious birth defect called microcephaly. Zika virus belongs to the family Flaviviridae (Lanciotti et al., *Yap State, Micronesia,* 2007). It was first discovered in 1947 and named after the Zika Forest in Uganda. In 1952, the first human cases of Zika were detected and since then, outbreaks of Zika have been reported in tropical Africa, Southeast Asia, and the Pacific Islands. ZKV sequences include GenBank Accession Nos.: EU545988, KJ776791, and AY632535 which are incorporated by reference as included in GenBank on Apr. 27, 2016. Additional ZKV species sequences can be identified by one skilled in the art.

III. Methods of Detecting Bacterial, Viral, and Protozoan Nucleic Acids

Herein disclosed are methods for detecting bacterial, viral, and protozoan nucleic acids in a biological sample such as those from individuals clinically suspected of being infected with said pathogens. The disclosed methods include real-time, quantitative (RT)-LAMP assays in which amplification reaction-components are shuffled and multiplexed for detection and identification of nucleic acids of pathogens (and their genotypes, subtypes or serotypes) including HIV, EBOV, MARV, HBV, HCV, CHIKV, MERS CoV, PAB19, CMV, JEV, MTB, HEV, DENV, SARS CoV, YFV, LFV, LE, TRY, ZKV and/or PLM. In some examples, the methods include real-time multiplex detection, quantitation, and differentiation of the genotypes of HCV in a sample and/or discriminating HCV-1 subtypes (such as HCV-1a, 1b, or 1c), HCV2 or HCV2 subtypes (such as HCV-2a, 2b, 2a/c, or 2c), HCV3 or HCV 3 subtypes (such as HCV-3a or 3b), HCV4 or HCV4 subtypes (such as HCV-4a, 4b, 4c, or 4d), HCV5 or HCV5 subtypes (such as HCV-5a), HCV-6 or HCV6 subtypes (such as HCV-6a or 6b) and HCV7. In other example, the method includes real-time multiplex isothermal detection, differentiation, and quantitation of HBV genotypes (for example detecting and/or discriminating HBV-A, HBV-B, HBV-C, HBV-D, HBV-E, or HBV-F). In other examples, the methods include real-time isothermal multiplex detection, differentiation, and quantitation of EBOV in a sample and/or discriminating EBOV genotypes, (such as ZEBOV, SUDV, RESTV, TAFV, and BDBV). In further examples, the methods include real-time isothermal multiplex detection, differentiation, and quantitation of HEV (such as HEV-1, 2, 3, and 4) in a sample. In other examples, the methods include real-time isothermal multiplex detection, differentiation, and quantitation of HIV in a sample (such as HIV-1 and HIV-2). In another example, the methods include real-time isothermal multiplex detection, differentiation, and quantitation of *Plasmodium* species (such as *Plasmodium falciparum, ovale, vivax,* and *malariae*). In further examples, the methods include real-time isothermal multiplex detection, differentiation, and quantitation of *Leishmania* species (e.g. such as *Leishmania donovani, braziliensis, tropica,* major, and *infantum*). In further examples, the methods include real-time isothermal multiplex detection, differentiation, and quantitation of *Trypanosoma* species (e.g. such as *cruzi,* gambiense, and *brucei* rhodesiense). In another example, the methods include real-time isothermal multiplex detection, differentiation, and quantitation of *Mycobacterium* species (such as *M. tuberculosis, M. avium, M. bovis*, and *M. lepra*). In further examples, the methods real time isothermal detection, quantitation, and identification include detecting CHIKV, MERS CoV, SARS CoV, PAB19, CMV, JEV, WNV, YFV, LFV, ZKV and MARV in a sample or detecting DENV in a sample (for example detecting and/or discriminating DEN-1, 2, 3, or 4). Primers and probes for use in the disclosed methods are provided herein.

The methods herein described may be used for any purpose for which real-time isothermal multiplex detection, differentiation, and quantitation of bacterial, viral, and protozoan nucleic acids of HIV, EBOV, MARV, HBV, HCV, CHIKV, MERS CoV, SARS CoV, PAB19, CMV, JEV, TB, HEV, DENV, YFV, LFV, LE, TRY, ZKV and/or PLM is needed in a field, laboratory, or clinical setting for diagnostic and prognostic applications. The nucleic acids are isolated from appropriate clinical biological samples including, but not limited to, cells, tissues, blood, serum, plasma, urine, cerebrospinal fluid, nasopharyngeal aspirates, middle ear fluids, bronchoalveolar lavage, tracheal aspirates, sputum, vomitus, buccal swabs, vaginal swabs, stool, and rectal swabs. The samples can be directly used in amplification reaction. In further example, the samples are first treated with lysis buffer or heat-treated before application in reaction medium. In some examples, nucleic acids are isolated or extracted from the samples with various nucleic acid extraction methods known to one of skill in the art.

The disclosed methods are highly sensitive and specific for real-time isothermal multiplex detection, differentiation, and quantitation of nucleic acids of HIV, EBOV, MARV, HBV, HCV, CHIKV, MERS CoV, SARS CoV, PAB19, CMV, JEV, MTB, HEV, DENV, YFV, LFV, LE, TRY, ZKV, and/or PLM nucleic acids. In some examples, the disclosed methods can detect presence of at least about 1 International Unit (IU equivalent to about 5 copies) of HBV, HIV, or HCV nucleic acids (e.g. at least about 10 to $10^5$ or more IU of HBV, CHIKV, or HCV nucleic acids) in a sample or reaction volume. In other examples, the disclosed methods can detect presence of at least about 1 copy of HBV, HCV, HIV, WNV, EBOV, MARV, HBV, CHIKV, MERS CoV, SARS CoV, PAB19, CMV, JEV, TB, HEV, DENV, YFV, LFV, LE, TRY, ZKV and/or PLM nucleic acids (e.g. at least about 10 to $10^6$ or more copies) in a sample or reaction volume. In some examples, the disclosed methods can predict with a sensitivity of at least 80% and a specificity of at least 80% for presence of one or more of HBV, HCV, HIV, WNV, EBOV, MARV, HBV, CHIKV, MERS CoV, SARS CoV, PAB19, CMV, JEV, MTB, HEV, DENV, YFV, LFV, LE, TRY, ZKV and/or PLM nucleic acids in a sample, such as a sensitivity of at least 85%, 90%, 95%, or even 100% and a specificity of at least of at least 85%, 90%, 95%, or even 100%.

In some embodiments, the methods for detecting parasitic, viral and/or bacterial nucleic acids in a sample utilizing LAMP or RT-LAMP methods of amplification and detection. LAMP is a rapid, specific, and sensitive one-step isothermal amplification method that can produce amplified nucleic acids in a short period of time using a DNA polymerase with strand displacement activity (see e.g., Notomi et al., *Nucl. Acids Res.* 28:e63, 2000). LAMP can also be used for amplification of RNA targets by addition of reverse transcriptase (RT) in a one-step reaction utilizing one temperature, hence referred to as RT-LAMP. (RT)-LAMP can also be multiplexed and performed in real-time by the addition of multiple pathogen-specific or species-specific LAMP primer sets, and pathogen-specific or species-specific fluorooligonucleotides in a single reaction medium. This capability is advantageous, for example, because it allows for incorporation of internal control(s), amplification of six or more regions within the same target, or simultaneous detection of about two, three or more targets or pathogens in a single reaction. In some examples, the disclosed methods include a real-time quantitative, multiplex (RT)-LAMP assay for detection, quantitation, and/or discrimination for example of two or more of HIV, HBV, WNV, PLM, CMV, DENV, TRY, and LE in a single reaction and provision of pathogen load.

In some examples multiple pathogen-specific and/or gene-specific oligonucleotides and novel fluorooligonucleotides sets of (RT)-LAMP primers are mixed at concentrations ranging from 0.1-1.5 µM and added to a reaction master-mix containing 2.5-10 µL of the "Lysis Reaction Buffer" (LRB) Buffer. Thermostable enzymes [about 100 to 120 Units of Maloney Murine Leukemia Virus (MMLV), about 4 to 6 Units of Avian Myeloblastisis Virus (AMV) or other reverse-transcriptase] and about 6 to 12 Units of Bst DNA polymerase or other strand-displacement enzymes (e.g. such as Bst 2.0 DNA polymerase, Bst 2.0 WarmStart™ DNA polymerase (New England Biolabs, Ipswich, Mass.), Taq DNA polymerase, VentR® and Deep VentR® DNA polymerases (New England Biolabs), Klenow fragment of DNA polymerase I), and 2 to 6 Units of RNAse Inhibitor) are also added. The template (extracted nucleic acid, lysis buffer treated and/or heat-treated specimen) is added to 10-25 µL the total reaction volume. The appropriate internal, negative, and positive controls are also included. The tubes containing the mixtures are then subjected to a one-step, closed-tube amplification procedure, using a single incubation temperature between 40 to 75° C. for about 10 to 40 minutes, on a real-time portable multichannel heat device. In other examples (such as for RNA targets of HIV, HCV, EBOV, or SARS CoV), the reaction is conducted as a one-step, close-tube procedure without an extra complementary DNA synthesis step.

In some embodiments, the target nucleic acid is DNA (such as an HBV, CMV, *Plasmodium* or *Mycobacterium* nucleic acid). In some examples the amplification process is monitored live, observed, and acquired in real-time from/by a real-time multichannel fluorospectrometric detector in the closed-tube, one-step, and one-temperature procedure. The results are acquired in real-time by monitoring or reading the different amplification curves, dissociation or melt curves (as illustrated below in FIGS. 9 and 10), which emerge from different emission wavelengths (λ 300-800) at defined temperatures, thereby indicating detection and simultaneous diagnostic differentiation. In further examples, utilizing special electronic applications, the detection, identification, and quantitative pathogen load or gene expression information is transmitted in real-time via blue-tooth, WiFi, or other wireless electronic means to the cloud, a smart phone or tablet and simultaneously monitored in real-time by a doctor, field investigator, or lab technician irrespective of location. Agarose gel (at about 2-3%) electrophoresis is not required, but optional. Reaction tubes can also be visualized with the naked-eye to view fluorescence glow of amplified nucleic acid which is also not required, but optional.

In some examples, the isothermal reaction is conducted using a mixture including a suitable buffer (e.g. a phosphate or Tris buffer). The buffer may also include additional components, such as NaCl, KCl, $MgCl_2$, $(NH_4)_2SO_4$, $MgSO_4$, and/or Triton-X100 or Tween-20. The buffer may also include other additives such as 1-proline, betaine or dimethylsulfoxide. The mixture may also contain nucleotides or nucleotide analogs such dATP, dCTP, dGTP, and dTTP. In one example, the buffer is Lysis Reaction Buffer (LRB), described in Section V may be used. In other examples, the buffer is Loopamp reaction mix (Eiken Chemical Co., Ltd., Tochigi, Japan) or another commercially available polymerase or RT reaction buffer. One of skill in the art can select an appropriate buffer and any additives using routine methods.

Reading of Results

In some examples, the disclosed methods include detecting fluorescence from a detectable label or probe incorporated in one or more (RT)-LAMP primers (such as LF, LR, F3, and R3, FIP, and RIP) as described in FIG. 14. In some examples, the sample is identified as containing a bacterial, viral, or parasite nucleic acid (for example is "positive" for the virus) if an increase in fluorescence is detected compared to a control (such as a no-template control sample or a known negative sample). In other examples, the amount of viral nucleic acid in a sample is determined quantitatively with a real-time multichannel fluorospectrophotometeric heating system, whereby the amount of viral nucleic acid in a test sample can be determined and calculated in real time by comparing to the amount of fluorescence obtained in pre-quantitated standard samples or amounts of nucleic acid of interest.

Primers

In particular embodiment, the hybridization chemistry and amplification mechanism of the detection assay of this invention utilize (RT)-LAMP primers or oligonucleotides (Loop Forward—LF, Loop Reverse—LR, Forward Outer—F3, Forward Inner Primer—FIP, Reverse Outer—R3 or Reverse Inner Primer—RIP) of any of the SEQ ID Nos 1-306 designed as single-stranded bi-labeled fluorescent probes that are held in a hairpin-loop conformation by complementary stem sequences of about 4-7 nucleotides at both ends of the probes. The 3'-end of the designated oligonucleotide is tagged with any reporter (e.g. FAM, TET, Texas-Red, etc.), while the 5'-end contains a quencher molecule (e.g. BHQ1, BHQ2, BHQ3, DABCYL, etc.) or vice versa; the main loop is a single-stranded DNA sequence of about 15-44 nucleotides that is either complementary or reverse complementary to the target gene sequence of the pathogens (FIG. 14). These probes are more stable, more specific and sensitive and are well preserved during the course of the reaction.

A. Real Time Multiplex Assays

In a particular example, a real-time quantitative multiplex (RT)-LAMP reaction comprises contacting a sample with two or more primers and probes, wherein a set of HCV (RT)-LAMP primers/probes (such as selected from SEQ ID NOs: 1-68), a set of HBV LAMP primers/probes (such as selected from SEQ ID NOs: 69-86), a set of HEV LAMP primers/probes (such as primers/probes selected from SEQ ID NOs: 87-100), a set of HIV (RT)-LAMP primers/probes (such as selected from SEQ ID NOs: 101-112), a set of WNV (RT)-LAMP primers/probes (such as a set of LAMP primers/probes selected from SEQ ID NOs: 113-118), a set of DENV (RT)-LAMP primers/probes (such as selected from SEQ ID NOs: 119-130), a set of CHIKV LAMP primers/probes (such as primers/probes selected from SEQ ID NOs: 131-143), a set of CMV LAMP primers/probes (such as selected from SEQ ID NOs: 144-150), a set of PLM LAMP primers/probes (such as SEQ ID NOs: 151-156), a set of EBOV (RT)-LAMP primers/probes (such as selected from SEQ ID NOs: 157-169), a set of MARV (RT)-LAMP primers/probes (such as SEQ ID NOs: 170-175), a set of YFV (RT)-LAMP primers/probes (such as primers/probes selected from SEQ ID NOs: 176-181), a set of LE LAMP primers/probes (such as SEQ ID NOs: 182-187), a set of LFV LAMP primers/probes (such as SEQ ID NOs: 188-209), a set of MTB LAMP primers/probes (such as selected SEQ ID NOs: 210-221), a set of MERS CoV (RT)-LAMP primers/probes (such as selected from SEQ ID NOs: 222-234), a set of PAB19 LAMP primers/probes (such as a set of LAMP primers/probes selected from SEQ ID NOs: 235-246), a set of JEV (RT)-LAMP primers/probes (such as primers/probes selected from SEQ ID NOs: 247-258), a set of SARS CoV (RT)-LAMP primers/probes (such as a set of LAMP primers/probes selected from SEQ ID NOs: 259-276), a set of TRY LAMP primers/probes (such as SEQ ID NOs: 277-294), and a set of ZKV (RT)-LAMP primers/probes (such as primers/probes selected from SEQ ID NOs: 295-306), under conditions optimal for simultaneous amplification of two or more HBV, HCV, HIV, WNV, EBOV, MARV, HBV, CHIKV, MERS CoV, SARS CoV, PAB19, CMV, JEV, MTB, HEV, DENV, YFV, LFV, LE, TRY, ZKV and/or PLM nucleic acid.

In another embodiment, the real-time quantitative isothermal multiplex methods comprises contacting the sample with at least one FIP, RIP, F3, R3, LR or LF primer that includes a fluorophore and a quencher (herein referred to in some examples as a "fluorooligonucleotide or fluoro-oligo"). In some examples, the multiplex set of primers include two, three or more pathogen or species-specific fluorooligonucleotides tagged with different fluorophores and quenchers each for one or more of the bacterial, viral, or protozoan nucleic acids that can be detected by the assay. This enables closed-tube, one-tube simultaneous detection and identification of multiple bacterial, viral, and protozoan nucleic acids present in the sample by fluorescence emission from each pathogen-specific fluoro-oligo. Relative to an internal quantitated assay positive control, an increase in fluorescence over background, no-template control, and/or a known negative control sample reaction would indicate the presence of the nucleic acid of particular pathogen(s) in the sample. In further example, the real-time quantitative multiplex set of primers which include one or more pathogen-specific or species-specific fluorooligonucleotide tagged with different fluorophores and quenchers can be shuffled and rearranged to target an intended group of pathogens (e.g. EBOV, PLM, and YFV or DENV, JEV, WNV, and LFV, among others).

IV. Lysis Buffer

Disclosed herein is a novel lysis buffer formulation that can be used for lysis of pathogen contained in blood product (e.g. plasma and serum). In some embodiment, the buffer is approximately of pH 7.8 and contains the following ingredients: about 5-20 mM Tris-HCl, 1-5 mM EDTA, 5-20% Sucrose, 0.1-0.4% Triton X-100, and 0.01-0.05% Tween-20 (see FIG. 13).

V. Assay Lysis-Reaction Buffer

Disclosed herein is a novel assay lysis-reaction buffer that can be used for nucleic acid detection. This novel buffer/solution was formulated to simultaneously perform lysis and amplification (the Lysis-Reaction Buffer—LRB is about pH 7.6 to 8.0 and of various stock concentrations). The buffer can be stored at room temperature, with no refrigeration required. The LRB comprises: 0.1-0.4% Triton-X 100; 10-20% Sucrose; 0.1-1M Trehalose; 5-40 mM Tris-HCl; 5-20 mM KCl; 5-20 mM $(NH_4)_2SO_4$; 5-12 mM $MgSO_4$;

1-3.0 mM each dNTPs; 1-5 mM Tris-Acetate; and 5-12 mM Potassium-Acetate. The LRB can be used to perform isothermal amplification, regular PCR or qRT-PCR, and complementary DNA synthesis. In some examples the buffer performs lysis of viral cells (from blood, plasma, and serum sample that are added to the reaction) and simultaneously amplified the released DNA or RNA, less nucleic acid extraction (see FIGS. 11 and 12). The LRB contains a combination of sucrose and trehalose which is a non-reducing disaccharide that confers stability as well as tolerance to heat and oxidation, increases enzymatic activities, and enhances priming specificity in differential real-time multiplex isothermal amplification reaction (see FIGS. 9 and 10). The LRB is highly stable at varying temperatures ranging from about 25° C. to 65° C. or higher and is stable for protracted periods of at least 12 months or more at room temperature. In a particular example, the LRB (containing at least about 12 Units of Bst DNA polymerase, ~6 Units of cloned AMV reverse-transcriptase, and about 4 Units of an RNase inhibitor) was heat-stressed at temperatures up to about 65° C. over a 5 to 7-day period, lyophilized and stored at room temperature for up to about 12 months or more. In other example, the lyophilized LRB (including enzymes) maintained an extreme stability, re-constituted/re-suspended with appropriate solutions (e.g. nuclease-free $H_2O$) and successfully utilized in (RT)-LAMP, PCR, and RT-PCR for synthesis and amplification of nucleic acid, hence demonstrating advantages over conventional or commercially available reaction buffers.

V. Primers, Probes, and Kits

Disclosed herein are primers and probes suitable for real-time quantitative isothermal multiplex detection, quantitation, and identification of bacterial, viral, and parasitic nucleic acids (such as HBV, HCV, HIV, WNV, EBOV, MARV, HBV, CHIKV, MERS CoV, SARS CoV, PAB19, CMV, JEV, MTB, HEV, DENV, YFV, LFV, LE, TRY, ZKV and/or PLM nucleic acids using real-time quantitative multiplex (RT)-LAMP.

In some embodiments, the disclosed primers and/or probes are about 10 to 60 nucleotides in length and are capable of hybridizing to, and in some examples, amplifying the disclosed nucleic acid molecules.

In other embodiments, the primers herein disclosed include (RT)-LAMP primers for real-time isothermal amplification of HCV nucleic acids, including primers with at least 90% sequence identity to any one of SEQ ID NOs 1-68 (which for example includes HCV universal primers). In further examples, the primers include (RT)-LAMP primers for real-time quantitative isothermal amplification of specific HCV genotypes and subtypes, such as primers with at least 90 to 99% sequence identity to SEQ ID NOs 1-68 (HCV-1, HCV-2, HCV-3, HCV-4, HCV-5, and/or HCV-6).

In another embodiments, the primers herein disclosed include (RT)-LAMP primers for real-time isothermal amplification of HBV nucleic acids, including primers with at least 90% sequence identity to any one of SEQ ID NOs 69-86 (which for example, includes HBV universal primers). In some examples, the primers include (RT)-LAMP primers for real-time quantitative amplification of nucleic acids of HBV genotypes, such as primers that consists of or having least 90 to 99% sequence identity to SEQ ID NOs 69-86 for real-time quantitative amplification of HBV nucleic acids (for example HBV-A, HBV-B, HBV-C, HBV-D, HBV-E, and/or HBV-F).

In further embodiments, the disclosed primers include (RT)-LAMP primers for real-time quantitative isothermal amplification of HEV nucleic acids, including primers with at least 90% sequence identity to any one of SEQ ID NOs 87-100. In some examples, the primers have at least 95 to 99% sequence identity to any one of SEQ ID NOs 87-100, comprise the sequence of any one of SEQ ID NOs 87-100, or consist of the sequence of any one of SEQ ID NOs 87-100 for amplification of HEV genotypes.

In additional embodiments, the primers herein disclosed include (RT)-LAMP primers for real-time isothermal quantitative amplification of HIV nucleic acids, including primers with at least 90% sequence identity to any one of SEQ ID NOs 101-112. In some examples, the disclosed HIV primers are capable of amplifying nucleic acids from HIV-1 and HIV-2. In some examples, the primers have at least 95 to 99% sequence identity to any one of SEQ ID NOs 101-112, comprise the sequence of any one of SEQ ID NOs 101-112, or consist of the sequence of any one of SEQ ID NOs 101-112.

In further embodiments, this disclosure include (RT)-LAMP primers for real-time quantitative isothermal amplification of WNV nucleic acids, including primers with at least 90% sequence identity to any one of SEQ ID NOs 113-118. In some examples, the primers have at least 95-99% sequence identity to any one of SEQ ID NOs 113-118, comprise the sequence of any one of SEQ ID NOs 113-118, or consist of the sequence of any one of SEQ ID NOs 113-118.

In still further embodiments, the disclosed primers include (RT)-LAMP primers for real-time quantitative isothermal amplification of DENV nucleic acids, including primers with at least 90% sequence identity to any one of SEQ ID NOs 119-130. In some examples, the primers are capable of amplifying nucleic acids from one or more DENV serotypes (for example, one or more of DENV-1, DENV-2, DENV-3, and/or DENV-4), such as SEQ ID NOs 119-130. In some examples, the primers have at least 95-99% sequence identity to any one of SEQ ID NOs: 62-75, comprise the sequence of any one of SEQ ID NOs 119-130, or consist of the sequence of any one of SEQ ID NOs 119-130. In particular examples, the primers amplify a DENV-1, DENV-2 DENV-3, and/or DENV-4 nucleic acid in real-time.

In further embodiments, this disclosure includes (RT)-LAMP primers for real-time quantitative isothermal amplification of CHIKV nucleic acids, including primers with at least 90% sequence identity to any one of SEQ ID NOs 131-143. In some examples, the primers have at least 95-99% sequence identity to any one of SEQ ID NOs 131-143, comprise the sequence of any one of SEQ ID NOs 131-143, or consist of the sequence of any one of SEQ ID NOs 131-143.

In another embodiments, this disclosure includes LAMP primers for real-time quantitative isothermal amplification of CMV nucleic acids, including primers with at least 90% sequence identity to any one of SEQ ID NOs 144-150. In some examples, the primers have at least 95-99% sequence identity to any one of SEQ ID NOs 144-150, comprise the sequence of any one of SEQ ID NOs 144-150, or consist of the sequence of any one of SEQ ID NOs 144-150.

In still further embodiments, the disclosed primers include (RT)-LAMP primers for real-time quantitative isothermal amplification of PLM nucleic acids, including primers with at least 90% sequence identity to any one of SEQ ID NOs 151-156. In some examples, the primers are capable of amplifying nucleic acids from one or more PLM species (for example, one or more of PLM-*falciparum*, PLM-*ovale*, PLM-*vivax*, and/or PLM-*malariae*), such as SEQ ID NOs 151-156. In some examples, the primers have at least 95-99% sequence identity to any one of SEQ ID NOs 62-75, comprise the sequence of any one of SEQ ID NOs 151-156, or consist of the sequence of any one of SEQ ID NOs 151-156. In particular examples, the primers can amplify a PLM-*falciparum*, PLM-*ovale*, PLM-*vivax*, and/or PLM-*malariae* nucleic acid in real-time.

In further embodiments, the disclosed primers include (RT)-LAMP primers for real-time quantitative isothermal amplification of EBOV nucleic acids, including primers with at least 90% sequence identity to any one of SEQ ID NOs 157-169. In some examples, the primers are capable of amplifying nucleic acids from one or more EBOV species (for example, one or more of ZEBOV, SUDV, TAFV, RESTV, and BDBV), such as SEQ ID NOs 157-169. In some examples, the primers have at least 95-99% sequence identity to any one of SEQ ID NOs 62-75, comprise the sequence of any one of SEQ ID NOs 157-169, or consist of the sequence of any one of SEQ ID NOs 157-169. In particular examples, the primers can amplify a ZEBOV, SUDV, TAFV, RESTV, and BDBV nucleic acid in real-time.

In additional embodiments, this disclosure includes (RT)-LAMP primers for real-time quantitative isothermal amplification of MARV nucleic acids, including primers with at least 90% sequence identity to any one of SEQ ID NOs 170-175. In some examples, the primers have at least 95-99% sequence identity to any one of SEQ ID NOs 170-175, comprise the sequence of any one of SEQ ID NOs 170-175, or consist of the sequence of any one of SEQ ID NOs 170-175.

In further embodiments, this disclosure includes (RT)-LAMP primers for real-time quantitative amplification of YFV nucleic acids, including primers with at least 90% sequence identity to any one of SEQ ID NOs 176-181. In some examples, the primers have at least 95-99% sequence identity to any one of SEQ ID NOs 176-181, comprise the sequence of any one of SEQ ID NOs 176-181, or consist of the sequence of any one of SEQ ID NOs 176-181.

In yet further embodiments, this disclosure includes (RT)-LAMP primers for real-time quantitative isothermal amplification of LE nucleic acids, including primers with at least 90% sequence identity to any one of SEQ ID NOs 182-187. In some examples, the primers have at least 95-99% sequence identity to any one of SEQ ID NOs 182-187, comprise the sequence of any one of SEQ ID NOs 182-187, or consist of the sequence of any one of SEQ ID NOs 182-187.

In still further embodiments, this disclosure includes (RT)-LAMP primers for real-time quantitative isothermal amplification of LFV nucleic acids, including primers with at least 90% sequence identity to any one of SEQ ID NOs 188-209. In some examples, the primers have at least 95-99% sequence identity to any one of SEQ ID NOs: 188-209, comprise the sequence of any one of SEQ ID NOs 188-209, or consist of the sequence of any one of SEQ ID NOs 188-209.

In additional embodiments, this disclosure includes (RT)-LAMP primers for real-time quantitative isothermal amplification of MTB nucleic acids, including primers with at least 90% sequence identity to any one of SEQ ID NOs 210-221. In some examples, the primers have at least 95-99% sequence identity to any one of SEQ ID NOs 210-221, comprise the sequence of any one of SEQ ID NOs 210-221, or consist of the sequence of any one of SEQ ID NOs 210-221.

In another embodiments, this disclosure includes (RT)-LAMP primers for real-time quantitative isothermal amplification of MERS CoV nucleic acids, including primers with at least 90% sequence identity to any one of SEQ ID NOs 222-235. In some examples, the primers have at least 95-99% sequence identity to any one of SEQ ID NOs 222-235, comprise the sequence of any one of SEQ ID NOs 222-235, or consist of the sequence of any one of SEQ ID NOs 222-235.

In further embodiments, this disclosure includes (RT)-LAMP primers for real-time quantitative isothermal amplification of PAB19 nucleic acids, including primers with at least 90% sequence identity to any one of SEQ ID NOs 236-246. In some examples, the primers have at least 95-99% sequence identity to any one of SEQ ID NOs 236-246, comprise the sequence of any one of SEQ ID NOs 236-246, or consist of the sequence of any one of SEQ ID NOs 236-246.

In still further embodiments, this disclosure includes (RT)-LAMP primers for real-time quantitative isothermal amplification of JEV nucleic acids, including primers with at least 90% sequence identity to any one of SEQ ID NOs 247-258. In some examples, the primers have at least 95-99% sequence identity to any one of SEQ ID NOs 247-258, comprise the sequence of any one of SEQ ID NOs 247-258, or consist of the sequence of any one of SEQ ID NOs 247-258.

In further embodiments, this disclosure includes (RT)-LAMP primers for real-time quantitative isothermal amplification of SARS CoV nucleic acids, including primers with at least 90% sequence identity to any one of SEQ ID NOs 259-276. In some examples, the primers have at least 95-99% sequence identity to any one of SEQ ID NOs 259-276, comprise the sequence of any one of SEQ ID NOs 259-276, or consist of the sequence of any one of SEQ ID NOs 259-276.

In further embodiments, this disclosure includes (RT)-LAMP primers for real-time quantitative isothermal amplification of TRY nucleic acids, including primers with at least 90% sequence identity to any one of SEQ ID NOs 277-294. In some examples, the primers have at least 95-99% sequence identity to any one of SEQ ID NOs 277-294, comprise the sequence of any one of SEQ ID NOs 247-258, or consist of the sequence of any one of SEQ ID NOs 277-294.

In still further embodiments, this disclosure includes (RT)-LAMP primers for real-time quantitative isothermal amplification of ZKV nucleic acids, including primers with at least 90% sequence identity to any one of SEQ ID NOs 295-306. In some examples, the primers have at least 95-99% sequence identity to any one of SEQ ID NOs 295-306, comprise the sequence of any one of SEQ ID NOs 295-306, or consist of the sequence of any one of SEQ ID NOs 295-306.

In some examples, at least one of the disclosed primers includes a detectable label, such as a fluorophore. In another examples, the F3, R3, FIP, RIP, LF, or LR primer (e.g., any one of SEQ ID NOs 1 to 306, specifically illustrated with SEQ NOs 1, 2, 5, and 6) includes a fluorophore at the 3' end and a quencher at the 5'end or vice versa at the 5' end and 3' end. In further examples, the F3, R3, FIP, RIP, LF, and LR primer (e.g., any one of SEQ ID NOs: 1 to 306) includes fluorophores such as FAM, TET, Cy3, Cy5, Texas-Red-615 or other fluorophore deemed suitable. In still further examples, the F3, R3, FIP, RIP, LF, and LR primer (e.g., any one of SEQ ID NOs: 1 to 306) includes a quenchers such as DABCYL or a dark quencher, which is a Black Hole Quencher (such as BHQ1, BHQ2, BHQ3) or other available quenchers deemed suitable.

The present disclosure provides a novel (RT)-LAMP "Shufflex" probes designed of the F3, R3, FIP, RIP, LF, or LR of any of the SEQ ID Nos 1-306 as single-stranded bi-labeled loop fluorescent probes that are held in a hairpin-loop conformation by complementary stem-sequences at both 5' and 3' ends or 3' and 5' ends, wherein the complementary stem sequences of the probes is about 4 to 7 nucleotides to which a desirable fluorophore, reporter or quencher is conjugated. In further example, the hairpin-loop of the probe is a single-stranded DNA sequence of about 15 to 44 nucleotides that is complementary and/or reversely complementary to the target gene sequence of the target pathogens. In still further example, Shufflex (RT)-LAMP probes can have 90 to 99% identity to a nucleic acid including those sequences shown in SEQ ID Nos 1-306, are more specific, highly sensitive, and well preserved over the time course of the real-time multiplex amplification reaction.

The nucleic acid primers and probes herein disclosed can be supplied in the form of a kit for use in the real-time quantitative, multiplex isothermal amplification of two or more bacterial, viral, and parasite nucleic acids (such as two or more of HBV, HCV, HIV, WNV, EBOV, MARV, HBV, CHIKV, MERS CoV, SARS CoV, PAB19, CMV, JEV, MTB, HEV, DENV, YFV, LFV, LE, TRY, ZKV and/or PLM). In such a kit, an appropriate amount of two or more of the nucleic acid probes and/or primers (such as two or more F3, R3, FIP, RIP, LF, LR primers or Shufflex probes of SEQ ID NOs 1-306) is provided in one or more containers or in one or more individual wells such as a multi-well nano-micro-fluidic plate for real-time quantitative multiplex isothermal amplification, detection and identification of bacterial, viral, and parasitic nucleic acid as well as quantitation of the pathogen load. The nucleic acid probe and/or primer may be provided in the form of an aqueous solution or may be provided in a freeze-dried or lyophilized form contained in bottles, microfuge tubes or in a multi-well plate. In some examples, the kit will provide some amount of LRB, DNA polymerase, reverse-transcriptase, nuclease-free water and other reagents needed for additional use as may be suggested by an enclosed protocol manual or needed by individual end-user. In such a kit is provided three or more assay positive and negative controls bacterial, viral, or parasitic nucleic acid as plasmids or transcripts. However, one of skill in the art can select other suitable controls.

The present disclosure is illustrated by the following non-limiting Examples.

Example 1

Assay Reagents

Sets of primers were designed for real-time multiplex (RT)-LAMP assays for HBV, HCV, HIV, WNV, EBOV, MARV, HBV, CHIKV, MERS CoV, SARS CoV, PAB19, CMV, JEV, MTB, HEV, DENV, YFV, LFV, LE, ZKV, TRY, and/or PLM (see Table 1). Any of the F3, R3, FIP, RIP, LF, LR primer for each set may include a complementary stem-attached fluorophore and quencher at the 5' and 3' ends or at the 3' and 5' ends, respectively; wherein "F"=fluorophore, "Q"=quencher, and stem of complementary nucleotides (see FIG. 14).

TABLE 1

| (RT)-LAMP nucleotide primer sequences | | | |
|---|---|---|---|
| Pathogen | Oligo Name | Oligonucleotide Sequence (5'-3') | SEQ ID NO. |
| HCV | N5F3 | CATAGTGGTCTGCGGAACC | 1 |
|  | N5R3 | CACGGTCTACGAGACCTCC | 2 |
|  | N5FIP | CGGGCATTGAGCGGGTTTATCCTTTTGGTGAGTACACCGGAATTGC | 3 |
|  | N5RIP | CGCGAGACTGCTAGCCGAGTTTTTAGCACCCTATCAGGCAGTAC | 4 |
|  | N5LF | AAAGGACCCGGTCATCCC | 5 |
|  | N5LR | GTCGCGAAAGGCCTTGTG | 6 |
|  | N6F3a | TAGTGGTCTGCGGAACCG | 7 |
|  | N6R3a | CACCGTCTACGAGACCTCC | 8 |
|  | N6FIPa | GGCATTGAGCGGGTTTGATCCATTTTGAGTACACCGGAATTGCCA | 9 |
|  | N6RIPa | GCAAGACTGCTAGCCGAGTAGCTTTTCACTCGCAAGCACCGTAT | 10 |
|  | N6LFa | AAAGGACCCGGTCGTCC | 11 |
|  | N6LRa | GTTGGGTTGCGAAAGGCC | 12 |
|  | N6F3b | CGGGAGAGCCATAGTGGT | 13 |
|  | N6R3b | CACCGTCTACGAGACCTCC | 14 |
|  | N6FIPb | TGAGCGGGTTTGATCCAATGGATTTTTGCGGAACCGGTGAGTAC | 15 |
|  | N6RIPb | CCGCAAGACTGCTAGCCGAGTTTTACCGTATCAGGCAGTACCAC | 16 |
|  | N6LFb | TCGTCCTGGCAATTCCGG | 17 |
|  | N6LRb: | TAGCGTTGGGTTGCGAAAG | 18 |
|  | N4F3b | ACCGGGTCCTTTCTTGGATT | 19 |
|  | N4R3b: | CGGTTGGTGTTACGTTTGGT | 20 |
|  | N4FIPb | GACCCAACACTACTCGGCTAGCTTTTCGCTCAATGCCCGGAAAT | 21 |
|  | N4RIPb | GCCTTGCGGTACTGCCTGATTTTTGATTCGTGCTCATGGTGCA | 22 |
|  | TF3 | CGGGAGAGCCATAGTGGT | 23 |
|  | TR3 | CACGGTCTACGAGACCTCC | 24 |

TABLE 1-continued (RT)-LAMP nucleotide primer sequences

| Pathogen | Oligo Name | Oligonucleotide Sequence (5'-3') | SEQ ID NO. |
|---|---|---|---|
| | TFIP | AGGCATTGAGCGGGTTTATCCATTTTTGCGGAACCGGTGAGTAC | 25 |
| | TRIP | CCGCAAGACTGCTAGCCGAGTTTTACCCTATCAGGCAGTACCAC | 26 |
| | TLF | AAAGGACCCGGTCGTCC | 27 |
| | TLR | GTTGGGTCGCGAAAGGC | 28 |
| | | | 29 |
| | | | 30 |
| | | | 31 |
| HCV | 2F3 | AATAGGGGCGACACTCCG | 32 |
| | 2R3 | GTCTTCCCGGCAATTCCG | 33 |
| | 2FIP | ACGCCATGGCTAGACGCTTTTTTTATGAACCACTCCCCTGTGA | 34 |
| | 2RIP | TGAGTGTCGTACAGCCTCCAGGTTTTCGGTTCCGCAGACCACTA | 35 |
| | 2LF | GTACTCACCGGTTCCGCA | 36 |
| | 2LR | CCCCCGCAAGACTGCTA | 37 |
| | SF3 | CCCCTGTGAGGAACTACTGT | 38 |
| | SFIP | ACTATGGCTCTCCCGGGAGGTTTTCGTCTAGCCATGGCGTTAG | 39 |
| | SRIP | GGAACCGGTGAGTACACCGGTTTTCCCAAATCTCCAGGCATTGA | 40 |
| | SLF | AGGCTGCACGACACTCATA | 41 |
| | SLR | GACCGGGTCCTTTCTTGGA | 42 |
| | 2-F3-1 | AGTGTCGTACAGCCTCCAG | 43 |
| | 2-R3-1 | ACCCTATCAGGCAGTACCAC | 44 |
| | 2-FIP-1 | ACCCAGTCTTCCCGGCAATTCTTTTCGGGAGAGCCATAGTGGT | 45 |
| | 2-BIP-1 | CCACTCTATGCCCGGCCATTTTTTCAACCCAACGCTACTCGG | 46 |
| | 2-LF-1 | TGTACTCACCGGTTCCGCA | 47 |
| | 2-LR-1 | TGCCCCCGCAAGACTGCTA | 48 |
| | 2-F3-2 | CGGGAGAGCCATAGTGGT | 49 |
| | 2-R3-2 | CACGGTCTACGAGACCTCC | 50 |
| | 2-FIP-2 | AATGGCCGGGCATAGAGTGGTTTTGCGGAACCGGTGAGTACA | 51 |
| | 2-RIP-2 | CCGCAAGACTGCTAGCCGAGTTTTCACCCTATCAGGCAGTACCA | 52 |
| | 2-LF-2 | CCAGTCTTCCCGGCAATTCCG | 53 |
| | 2-LR-2 | TAGCGTTGGGTTGCGAAAGGC | 54 |
| | HCaF3 | CCCCTGTGAGGAACTACTGT | 55 |
| | HCaR3 | CTCGGCTAGCAGTCTTGC | 56 |
| | HCaFIP | ACTATGGCTCTCCCGGGAGGTTTTCGTCTAGCCATGGCGTTAG | 57 |
| | HCaRIP | GGTCTGCGGAACCGGTGAGTATTTTGACCGGACATAGAGTGGGT | 58 |
| | HCaLF | GGAGGCTGTACGACACTCATA | 59 |
| | HCaLR | GGAATTCCCGGAAAGACTGGG | 60 |
| | HCa2R3 | CGT ACT CGC AAG CAC CCT ATC | 61 |
| | | | 62 |
| HVC | DF3-2n | GCCATAGTGGTCTGCGGAA | 63 |
| | DR3-2n | AAGCACCCTATCAGGCAG | 64 |
| | DFIP-2n | TATTGAGCGGGTTGCTCCAAGTTTTCCGTGAGTACACCGGAATC | 65 |
| | DRIP-2n | CCAGAATTTGGGCGTGCCCTTTTACCACAAGGCCTTTCGCGA | 66 |
| | DLF-2n | AGGACCCGGTCACCCCAGC | 67 |
| | DLR-2n | CGCGAGATCACTAGCCGAGTAGTG | 68 |
| HBV | HBF3 | GAA CAT GGA GAA CAT CAC ATC A | 69 |
| | HBR3 | GAT AAA ACG CCG CAG ACA CAT C | 70 |
| | HBFIP | GGG TGA TCC CCC TAG AAA ATT G-TTTT-GAA TCC TCA CAA TAC CGC AGA G | 71 |
| | HBRIP | GTG TGT CTT GGC CAA AAT TCG C-TTTT-CAG CGA TAA CCA GGA CAA ATT G | 72 |
| | HBLF | AGA AGT CCA CCA CGA GTC TAG | 73 |
| | HBLR | TCA CTC ACC AAC CTC CTG TCC T | 74 |
| | HBF3c | AACATCACTACCAGCACGG | 75 |
| | HBR3c | ACCACTGAACAAATGGCACT | 76 |
| | HBFIP3c | TGCAGTTTCCGTCCGAAGGTTTTTTTGCAAGACCTGCACGATTC | 77 |
| | HBRIP3c | CCATCCCATCATCCTGGGCTTTTTTAGGAGAAACGGACTGAGGC | 78 |

TABLE 1-continued (RT)-LAMP nucleotide primer sequences

| Pathogen | Oligo Name | Oligonucleotide Sequence (5'-3') | SEQ ID NO. |
|---|---|---|---|
| | HBLF3c | AAACATAGAGGTTCCTTGAGCAG | 79 |
| | HBLR3c | TCGCAAGATTCCTATGGGAGT | 80 |
| | HBF3n | CATCACTACCAGCACGGGAC | 81 |
| | HBR3n | CCACTGAACAAATGGCACTAGT | 82 |
| | HBFIP3n | TGCAGTTTCCGTCCGAAGGTTTTTTTGCAAGACCTGCACGATTC | 83 |
| | HBRIP3n | CCATCCCATCATCCTGGGCTTTTTTCAGGAGAAACGGACTGAGGC | 84 |
| | HBLF3n | GAAACATAGAGGTTCCTTGAGCAG | 85 |
| | HBLR3n | TCGCAAGATTCCTATGGGAGT | 86 |
| HEV | HE1F3 | GTTGCTGCTCCTCATGTTTTTGC | 87 |
| | HE1R3 | TGGCGAACACGAGGTCCAGC | 88 |
| | HE1FIP | ACCGCCGCTGCGCCGCCCAC-TTTT-ATGCTGCCCGCGCCACCGCC | 89 |
| | HE1RIP | GGCGGTGGTTTCTGGGGTGA-TTTT-CGGCCGCAGCGGTGACATCG | 90 |
| | HE1LF | CGGCGGCCAGACGGCTGAC | 91 |
| | HE1LR | GGTTGATTCTCAGCCCTTCG | 92 |
| HEV | HE3-F3 | GCCCTTCGCCCTCCCCTATATT | 93 |
| | HE3-R3a | AGGTACAGGGGCTGTGTCAG | 94 |
| | HE3-R3b | CAACATCAGGTACAGGGGCTG | 95 |
| | HE3-R3b | CAACATCAGGTACAGGGGCTG | 96 |
| | HE3-FTP | CGGCTGCCGAGGGCGAGTTCCA-TTTT-GATTCTCAGCCCTTCGCCCTCC | 97 |
| | HE3-RIP | GTGACCAGTCCCAGCGCCCCTC-TTTT-GAGATAGCAGTCAACGGCGC | 98 |
| | HE3-LFc | GAT TGT GAA ACG ACA TCG GC | 99 |
| | HE3-LRc | CTGCCCCAGCTGGGGCTGCGCC | 100 |
| HIV | HI1F3 | CAC CAT GCT AAA CAC AGT GG | 101 |
| | HI1R3 | TCC TGA AGG GTA CTA GTA GT | 102 |
| | HI1FIP | TCT GCA GCT TCC TCA TTG ATG G-TTTT-CACAGTGG GGGGACATCA AGCA | 103 |
| | HI1RIP | ATG GGA TAG ATT GCA TCC AGT G-TTTT-CTT CCC CTT GGT TCTCTCATC T | 104 |
| | HI1LF | TCT TTT AAC ATT TGC ATG GC | 105 |
| | HI1LR | CAT GCA GGG CCT ATT GCA CCA G | 106 |
| | HI2F3 | CAG GGA CTT TCC AGA AGG GGC | 107 |
| | HI2R3 | AGG TCT TTA AGC AAG CAA GCG | 108 |
| | HI2FIP | AAGCGGGTACATTTATACAG-TTTT-CCAAGGGAGGGACATGGGAG | 109 |
| | HI2RIP | TGCATTGTATTCAGTCGCT-TTTT-GCT CTA CCT GCT AGT GCT | 110 |
| | HI2LF | GGC GTT CCC CAC CAG CTC | 111 |
| | HI2LR | GCG GAG AGG CTG GCA GAT | 112 |
| WNV | WNF3 | GTT GGC TCT CTT GGC GTT CTT C | 113 |
| | WNR3 | TCA TAA GTG ATA GTA TCA TCG C | 114 |
| | WNFIP | AGC ACT GGT CAA GGT CCC TAG T-TTTT-AGG TTC ACA GCA ATT GCT CC | 115 |
| | WNRIP | CAGTCATG ATTGGCCTGA TCGC-TTTT-CAT CAC CTT CCC TTG GAA GTT A | 116 |
| | WNLF | CCT TCT TAA AAC TCA GAA GGT G | 117 |
| | WNLR | GCGT AGGAGCAGTT ACCCTCT | 118 |
| DENV | D1F3 | GCC ACG GTT TGA GCA AAC CGT G | 119 |
| | D1R3 | TTA TTG TTA TGC CGG GGG TCT C | 120 |
| | D1FIP | GCTACCCCATGCGTACAGCTTC-TTTT-GCCTGTAGCTTCATCGTGGGGA | 121 |
| | D1RIP | AGACTAGTGGTTAGAGGAGACC-TTTT-CAGGATACAGCTTCCCCTGGTG | 122 |
| | D1LF | CAT GGG TTG CAG CCT CCC AGG | 123 |
| | D1LR | AACATAACGCAGCAGCGGGG CC | 124 |
| DENV | D2-F3 | CAGGAGGAAGCTGGGTTGAC | 125 |
| | D2-R3 | ACCATGGAGTGTTTGCAGA | 126 |
| | D2-FIP | CTTCCATGTTCCAAGACTA-TTTT-CTGGGTTGACATAGTCTTG | 127 |
| | D2-RIPa | CTGTGTGACGACGATGGCG-TTTT-GGCTTCTGTTTTTATCAG | 128 |
| | D2-RIPb | CTGTGTGACGACGATGGCG-TTTT-GTCAGCTTTGCCTCTATACA | 129 |
| | D2-LF | CAGTTCAAAATCCAATGTTGG | 130 |

TABLE 1-continued (RT)-LAMP nucleotide primer sequences

| Pathogen | Oligo Name | Oligonucleotide Sequence (5'-3') | SEQ ID NO. |
|---|---|---|---|
| CHIKV | CKF3 | GAC TCA ACC ATC CTG GAT ATC G | 131 |
| | CKR3 | GCG TCT CCG TGT CTG GCA CGG CC | 132 |
| | CKR3a | CTG TCT ACA TGA GAC GTC TGT G | 133 |
| | CKFIP | CTC TCG GGA TCT TCC GCA CTG C -TTTT- CAGCAAGGAGGATGATGTCGGA | 134 |
| | CKRIP | CTCGCCAATTATGCGAGAAAGC -TTTT-TAC TGC TTG TAA GTC CCC GAT C | 135 |
| | CKLF | GCAGACGCAGTGGTACTTCCTG | 136 |
| | CKLR | GCATCTGCCGCAGGAAAAGTCC | 137 |
| | CV-F3 | CCT GGA TAT CGG CAG TGC GC | 138 |
| | CV-R3 | GGC ACG GCC ATT ACT GCT TG | 139 |
| | CV-FIP | GGG ATC TTC CGC ACT GCG CA-TTTT-AGG AGG ATG ATG TCG ACA G | 140 |
| | CV-RIP | TAT GCG AGA AAG CTA GCA TC-TTTT-CTT TCC AGA GAT GTT TCT GT | 141 |
| | CV-LF | GGG CAG ACG CAG TGG TAC TT | 142 |
| | CV-LR | TGC CGC AGG AAA AGT CCT GG | 143 |
| CMV | CMF3 | CCG ACA AGA AGA GGC CGG CG | 144 |
| | CMR3 | CGA TCT GTC GTA GTG CCC ACT G | 145 |
| | CMFIP | GGT GTT TGT GAG AGG CAG GTG A -TTTT-GCC CTA GAC CGC CAG GCC GCA C | 146 |
| | CMRIP | CGT GGA CCT GGC CAA ACG AGC CC-TTTT- ATG TAG ACC AGG CGT ACG AGG C | 147 |
| | CMRIPa | CGT GGA CCT GGC CAA ACG AGC CC -TTTTT- AGA TGT TGC TGA TTC TGT TTA G | 148 |
| | CMLF | CAT AAA TTC TTG TAT TTG TAA G | 149 |
| | CMLR | TCA CCG ACA TCA CCA GCC TCG T | 150 |
| PLM | PFF3 | GCT TCC TTC AGT ACC TTA TG | 151 |
| | PFR3 | GCA TCA CCA TCC AAG AAA TC | 152 |
| | PFFIP | TTC CGT CAA TTC TTT TAA CT-TTTT-ATC AAA GTC TTT GGG TTC TG | 153 |
| | PFRIP | GGG CAC CAC CAG GCG TGG AG-TTTT-TCT TGT CTT AAA CTA GTG AG | 154 |
| | PFLF | TCG CTT GCG CGA ATA CTC | 155 |
| | PFLR | GCG GCT AAA TTT GAC TCA AC | 156 |
| EBOV | EZgF3 | CCA CAA GAT CTT GAC AGC AG | 157 |
| | EZgR3 | CCG CAC TCT CTT GAA AAT CAA C | 158 |
| | EZgR | GCA TGA AAG GAA ACT GTT CCG C | 159 |
| | EZgFIP | ACT TGA TAC ACT GGG ATG A-TTTT-GTC TGT CCG TTC AAC AGG | 160 |
| | EZgRIP | ACA ATC TTG AGG AAA TTT GC-TTTT-ACT CTC TTG AAA ATC AAC AC | 161 |
| | EZgLF | CTC TTT GCC GAA CAA TCC | 162 |
| | EZgLR | CAA CTT ATC ATA CAG GCC TTT G | 163 |
| | EBZ-F3 | GCATCAAGCATCATGGCACC | 164 |
| | EBZ-R3 | CTG ACA TGC ATA TAA CAC TGT G | 165 |
| | EBZ-FIP | TAC CTA AAT GCA AGA TTG TA-TTTT-CAT GCC ACA GTT AGA GGG AG | 166 |
| | EBZ-RIP | GAGTTTACAGCACCTTTTAT-TTTT-TTA AAA ACA TTC TTA ACA CC | 167 |
| | EBZ-LF | TCT CTA AAT CAG TTA CAA AGC | 168 |
| | EBZ-LR | GAA TAT TGC AAC CGT TGC TA | 169 |
| MARV | MBVF3 | GAC ACA CAA AAA CAA GAG ATG | 170 |
| | MBVR3 | TCC CTG AGT TTA TTG CAT CTA T | 171 |
| | MBVFIP | GGG GCT GTG GGT TTT GTA CC-TTTT-ATG ATT TTG TGT ATC ATA TAA A | 172 |
| | MBVRIP | CAT GTT CGT AAT AAG AAG GTG AT-TTTT- TTA CAG ATA CTA ACC TGA TG | 173 |
| | MVBLF | AAT GTC AAT GTT AAT ATT CTT C | 174 |
| | MBVLR | GCC CCT CAT GTT CGT AAT AAG A | 175 |
| YFV | YF2F3 | CAG AGA TGG AGA CTC ATA CTA C | 176 |
| | YF2R3 | ACA ATT CCT CAC TAG TTC TCT G | 177 |
| | YF2FIP | CAC CTC CAT GTT GTC CAA GAG C-TTTT- CAAgtGAAGATAATGCCCACCA | 178 |
| | YF2RIP | GCC CCA CTC TAT GGC GTT GAA G -TTTT-TCC TCT GGT CAT CCC TCA GTC T | 179 |
| | YF2LF | GAG GCC TCC AAC CAG CAG AC | 180 |
| | YF2LR | CAC CAG TTT CCC CTG GTG AAA T | 181 |

TABLE 1-continued (RT)-LAMP nucleotide primer sequences

| Pathogen | Oligo Name | Oligonucleotide Sequence (5'-3') | SEQ ID NO. |
|---|---|---|---|
| LE | LEF3 | CAC GCG AAA GCT TTG AGG TTA CA | 182 |
|  | LER3 | GCT TGG ATC TCG TCC GTT GAC GG | 183 |
|  | LEFIP | ATT AAA CCG CAC GCT CCA CGT C-TTTT-GTC TCA GGG GGG AGT ACG TTC G | 184 |
|  | LERIP | GTA AAG TTC CCC GTG TTG AGT C-TTTT-TGC ACC ACC ATT CAG GGA ATC G | 185 |
|  | LELF | GTG GTG CCA TTC CGT CAA TTT C | 186 |
|  | LELR | ATC CTC ATC CTG TCC GGA TCT G | 187 |
| LFV | LA1F3 | GAG GCT GAA CTA AAA TGC TTC | 188 |
|  | LA1R3 | AAT GCT CAT TTG TGC TTC AGC T | 189 |
|  | LA1FIP | TTG AAG TCA AAC AGC CTC AGC A -TTTT-GAACACAGCTGTGGCAAAATGT | 200 |
|  | LA1RIP | AAC AAG CCA TTC AAA GGC TGA A-TTTT-AAT GCT CAT TTG TGC TTC AGC T | 201 |
|  | LA1LF | TGT CAC AAA ATT CCT CAT CAT G | 202 |
|  | LA1LR | AGCTGAAGCACAAATGAGCATT | 203 |
|  | LA2F3 | TTC CGG GGG AGT GCA TCA AT | 204 |
|  | LA2R3 | GCA ACT TGA CCC AAA TGC TAA G | 205 |
|  | LA2FIP | AAG CAG GAT GCT AAG TAC TCA C -TTTT-CAG CAC TGG TCA AGC CCG GTT G | 206 |
|  | LA2RIP | AAT CAG TAG GTT CAC GGA AGA A -TTTT-TGA AGG AAG ACC TGA AGA TC | 207 |
|  | LA2LF | TTG ATG TCA CAG ACC TCT TCG C | 208 |
|  | LA2LR | AAG TTC AGG CTG CTA CAT ACA C | 209 |
| MTB | TB1F3 | CGGTTCAGGCTTCACCACAGTG | 210 |
|  | TB1R3 | GAGTTGGATCTGATGTCCGAGT | 211 |
|  | TB1FIP | ATTGAGCCAAGCCCTTTGCTGA-TTTT-CGGCGACCCTAAGGTTGACGAC | 212 |
|  | TB1RIP | CGTCCAGCCATTGACCATCGTC-TTTT-GCGCTCGATTTCGTTTTGGACA | 213 |
|  | TB1LF | CGCTGAGATTAGCATCACTGCT | 214 |
|  | TB1LR | GCTCTGTTATCCGTGCCGAGCA | 215 |
|  | TB2F3 | TCACGACAGATTGCGATGTACC | 216 |
|  | TB2R3 | AGAACGTTGTCGGAAGAACACGC | 217 |
|  | TB2FIP | ATCTTGCGTTGGGCGTACATGA-TTTT-CGTGAGCTCACCGATCTTTCGT | 218 |
|  | TB2RIP | CTGTCCGAGATGGCCGAGCGCC-TTTT-AGCGCTTGGAGCGCTGACGGAT | 219 |
|  | TB2LF | GGTTGTGTGATCACGGCCGAAC | 220 |
|  | TB2LR | GTGAGGTCTTTGATCACGTCAA | 221 |
| MERS CoV | ME1F3 | CAAGGTGCGCGCGGTACGTA | 222 |
|  | ME1R3 | GCAATGAGCCTCTCAACCAG | 223 |
|  | ME1FIP | TTCCTGAACCACAGAGTGGC-TTTT-GAGCAGCGCTCAACTCTGAA | 224 |
|  | ME1RIP | GCCTATGAAGTGGTGAAGGC-TTTT-GGAGGTGTCTAGTGTGTCCA | 225 |
|  | ME1LF | GTTAGAGACACATGGTCTTG | 226 |
|  | ME1LR | CTATGTGCCCATCCGGCTGG | 227 |
| MERS CoV | ME2F3 | CGTTGTCAACGATGTTGTCCT | 228 |
|  | ME2R3 | CACCTAAGCCAGTGAGAACTAC | 229 |
|  | ME2R3a | ACAGAGTTGCAAACCTTGTACG | 230 |
|  | ME2FIP | CACGCAACTTGTCAAGGGTG-TTTT-CGCAATTCTCTCTGGAACCA | 231 |
|  | ME2RIP | CGTAGCAGTCACTGCCGGCC-TTTT-TAATGGCGGCATACTGTAATC | 232 |
|  | ME2LF | CACCTTTGAGAAGCTGGCGTA | 233 |
|  | ME2LR | GCTATTAATGTTGGTGGTACAG | 234 |
| PAB19 | PV1F3 | AGTTATCTGACCACCCCCATGCC | 235 |
|  | PV1R3 | GGATTTATTCCCAACTTAGCCA | 236 |
|  | PV1FIP | CCCAACATAGTTAGTACCGGGT-TTTT-TGCAGTATTATCTAGTGAAGAC | 237 |
|  | PV1RIP | ACCCGGTACTAACTATGTTGGG-TTTT-CATGAATCCTTGCAGCACTGTC | 238 |
|  | PV1LF | CTTGCCCAGGCTTGTGTAA | 239 |
|  | PV1LR | CCTGGCAATGAGCTACAAGC | 240 |
|  | PV2F3 | AGTTATCTGACCACCCCCATGCC | 241 |
|  | PV2R3 | CCAACTTAGCCAGTTGGCTATA | 242 |
|  | PV2FIP | CCCAACATAGTTAGTACCGGGT -TTTT-CATCCAGTAGCAGTCATGCAGA | 243 |

TABLE 1-continued (RT)-LAMP nucleotide primer sequences

| Pathogen | Oligo Name | Oligonucleotide Sequence (5'-3') | SEQ ID NO. |
|---|---|---|---|
| | PV2RIP | CCTGGCAATGAGCTACAAGCTG-TTTT-AACTTAGCCAGTTGGCTATACC | 244 |
| | PV2LF | CCAGGCTTGTGTAAGTCTTCAC | 245 |
| | PV2LR | CAGTGCTGCAAGGATTCATGACT | 246 |
| JEV | JEF3 | CACGGCCCAAGCCTCGTCTA | 247 |
| | JER3 | CGGCGCTCTGTGCCTAGTAGCTG | 248 |
| | JEFIP | TCGAGGGGGCTTGGGCCGCA-TTTT-GTGTAAGGACTAGAGGTTAG | 249 |
| | JERIP | GAGGAGGTGGAAGGACTAGA-TTTT-GTTGAGATAGAGCAGAAGAT | 250 |
| | JELF | TGTTGTTTCCACGGGGTCTCCT | 251 |
| | JELR | TTGACACCTGGGAATAGACTGG | 252 |
| | JE1F3 | CCAGGAGGACTGGGTTAACA | 253 |
| | JE1R3 | AGTAGCTGATGTTGAGATAG | 254 |
| | JE1FIP | TTGTTTCCACGGGGTCTCCT-TTTT-CACGGCCCAAGCCTCGTCTA | 255 |
| | JE1RIP | TGCGGCCCAAGCCCCCTCGA-TTTT-GAAGATCTCCCAGTCTATTC | 256 |
| | JE1LF | CTAACCTCTAGTCCTTACAC | 257 |
| | JE1LR | CTAGAGGTTAGAGGAGACCCCG | 258 |
| SARS CoV | SA1F3 | TAC TGT CGT TGA CAA GAA ACG A | 259 |
| | SA1R3 | GCT CTA CTA GAC CAC AAG TGC C | 260 |
| | SA1FIP | GAC GAA ACC TAG GTA TGC TG-TTTT-ACT CGT CCC TCT TCT GCA GA | 261 |
| | SA1RIP | GAT GGA GAG CCT TGT TCT TG-TTTT-ACT AGC ACG TCT CTA ACC TG | 262 |
| | SA1LF | GAT CGA CTG CAA CAC GGA CG | 263 |
| | SA1LR | CAC ACG TCC AAC TCA GTT TGC C | 264 |
| | SA2F3 | TGG GAG ATT CTC AAA TTT CTC A | 265 |
| | SA2R3 | TGC CTT AAG AGG CAT GAG TAG T | 266 |
| | SA2FIP | CCA GCG ATA GTG ACT TGA TC-TTTT-GTC AAG GGT CAA ATA CAG GT | 267 |
| | SA2RIP | TGC GAT CAC TCA ACT TAG GT -TTTT-TGC TCC TTG CCA CGT ATA CA | 268 |
| | SA2LF | ATG CAC ATT TCG AGT GCC TTG | 269 |
| | SA2LR | GAA GTC TTC ATC GCT CAA AGC A | 270 |
| | SA3F3 | CAC ATG ATG TTT CAT CTG CAA T | 271 |
| | SA3R3 | TTG TGA TAG CCA CAT TGA AGC G | 272 |
| | SA3FIP | TTC TGT GAA TTA TAA GGT GA-TTTT-ATA GGC GTT GTA AGA GAA TT | 273 |
| | SA3RIP | AAT CTT AGG ATT GCC TAC GC -TTTT-GAC ATT ACA AGA GTG TGC TG | 274 |
| | SA3LF | TCC AAG CAG GAT TGC GTG TAA G | 275 |
| | SA3LR | CAC AGG GTT CTG AAT ATG ACT A | 276 |
| TRY | TCF3 | CAT GCC TTC CCT CAA CTC ACG G | 277 |
| | TCR3 | GTG TCA TCG TTT GCA GTG TGG A | 278 |
| | TCFIP | GTG CGG TCT AAG AAT TTC AC-TTTT-ATC CAG GAA TGA AGG AGG GT | 279 |
| | TCRIP | ACT ACA GCG AAG GCA TTC TT-TTTT-ATG GTC TCT AAT CAT CTT CG | 280 |
| | TCLF | GAC GCA CCA GTA CGT TCT CC | 281 |
| | TCLR | CTC AAT CAA GAA CCA AAG TGT G | 282 |
| | TRbF3 | AGA AGT CAT TCA GGA ATC TG C | 283 |
| | TRbR3 | CCT GAA TGC GAC GCC ATG CCT C | 284 |
| | TRbFI | GCA TCG TGA AGG TTA CGT AG-TTTT-AAT CAA GGA CGC GAA GCG CC | 285 |
| | TRbRI | ACT TGG AGG ACG CCG AAG CC-TTTT-GTT TGT CGA GGT TCT CGT GG | 286 |
| | TRbLF | GTC CTC GCA GTG TTG CTT AA | 287 |
| | TRbLR | GGT TCG CCA CGC AGA AGG AG | 288 |
| | TRbrF3 | AAG TAC CTT GGC GCT CGC G | 289 |
| | TRbrR3 | TGC GTT GAG TAC GCA TCT TG | 290 |
| | TRbrFI | TGC AAA CCT TCT TGA CGG GC-TTTT-CTA AAG CTG CTG GCA GTG CC | 291 |
| | TRbrRI | GCA GAC GTC GCA GGA ATC GC-TTTT-ACT ATG TTT GAC GCC GCG GC | 292 |
| | TRbrLF | CTT CGT CAA AGG CGG TGC CA | 293 |
| | TRbrLR | CAA GTA TCG GCA GCA ACC GA | 294 |
| ZKV | ZK1-F3 | GGA TTT GGA AAC GAG AGT TT | 295 |
| | ZK1-R3 | CTA TTG ATG AGA CCC AGT GA | 296 |

TABLE 1-continued (RT)-LAMP nucleotide primer sequences

| Pathogen | Oligo Name | Oligonucleotide Sequence (5'-3') | SEQ ID NO. |
|---|---|---|---|
| | ZK1-FIP | GCC CCC AAA GGG GCT CAC AC-TTTT-GGA TTC CGG ATT GTC AAT AT | 297 |
| | ZK1-RIP | GAG GCT GCC AGC CGG ACT TC-TTTT-GCT TGA TTG CCG TGA ATC TC | 298 |
| | ZK1-LF | GGG CTA CTC CGC GTT TTA GC | 299 |
| | ZK1-LR | GCT GGG TCA TGG GCC CAT CA | 300 |
| | ZK2-F3 | CTT GAC TAT GAA TAA CAA GCA CT | 301 |
| | ZK2-R3 | AAG TGG CCA GAG GAC AGC CT | 302 |
| | ZK2-FIP | TCC TTG AAC TCT ACC AGT GC-TTTT-GAC ATT CCA TTA CCT TGG CA | 303 |
| | ZK2-RIP | GGC AAA CTG TCG TGG TTC TA-TTTT-TCA GCC TCC AGA GCT CCA GC | 304 |
| | ZK2-LF | GTG GAG TTC CGG TGT CTG CC | 305 |
| | ZK2-LR | GGA GCA GTT CAC ACG GCC CT | 306 |

This novel Lysis-Reaction Buffer—LRB; ~7.8-pH 8.0) is sensitive, robust and thermostable and formulated to simultaneously perform lysis and real-time amplification of nucleic acids. The buffer can be stored at room temperature. The LRB contains about 0.1-0.4% Triton-X 100; 10-20% Sucrose; 0.1-1M Trehalose; 5-40 mM Tris-HCl; 5-20 mM KCl; 5-20 mM (NH4)2SO4; 5-12 mM MgSO4; 1-3.0 mM each dNTPs; 1-5 mM Tris-Acetate; and 5-12 mM Potassium-Acetate.

Example 2

RT-LAMP Assay for Rapid Detection and Genotype-Identification of Hepatitis C Virus 1-6.

The subject matter of this example is included in Nyan and Swinson (International Journal of Infectious Diseases; DOI: http://dx.doi.org/10.1016/j.ijid.2015.12.002) that is referenced in part.

Introduction

Hepatitis C virus (HCV) is a single-stranded RNA virus of the Flaviviradae family (Moratorio et al., Virol J. 4: 79, 2007). Transmitted through modes including injection drug use (IDU), contaminated needle-stick injuries, and unsafe blood transfusion, infection with HCV may lead to chronic-active hepatitis and hepatocellular carcinoma (Ghany et al., Hepatology 4:1335-1374, 2009; Liang et al., Ann. Int. Med. 132:296-305, 2000; NIH Consensus Statement on Management of Hepatitis C; NIH Consens. Sci. Statements 19:1-46, 2002) Approximately 185 million people are infected with HCV worldwide, with developing countries of Sub-Saharan Africa, Asia, North and South America, and the Middle East mostly affected (Messina et al., Hepatology 61:77-87, 2015; Gower et al., J Hepatol 61: S45-57, 2014; Zein et al., Clin Microbiol Review 13: 223-35, 2000). There are 7 major genotypes of HCV with 67 subtypes found in different regions of the world (Smith et al., Hepatology 59: 318-27, 2014; Lamballerie et al., J Gen Virol 78: 45-51, 1997; Simmonds et al., Hepatology 19: 1321-24, 1994). Globally, HCV genotype 1 is the most common, accounting for about 46% of all infections. This is followed by genotype 3 (22%) and genotypes 2 and 4, each accounting for 13% of global HCV burden (Messina et al., Hepatology 61:77-87, 2015; Gower et al., J Hepatol 61: S45-57, 2014; Zein et al., Clin Microbiol Review 13: 223-35, 2000). Detection of HCV infection in blood-derivatives and identification of the genotypes are therefore important in clinical diagnostics and antiviral treatment, ensuring blood safety, and providing epidemiological information about HCV prevalence (Infectious Diseases Society of America—IDSA. www.hcvguidelines.org 1-100, 2014; De Leuw et al., Liv. Intl. 31: Suppl. 1: 3-12; Etoh et al., BMC Res Notes 24: 316, 2011).

A plethora of molecular diagnostic methods have been designed and used for detection and genotyping of HCV infection. While these test are highly sensitive, they remain expensive, laborious, and require well-trained personnel as well as sophisticated laboratory facilities. (Rho et al., Journal of Microbiol 46: 81-87, 2008; Nolte et al., J Clin Microbiol. 33: 1775-78, 1995; Sábato et al., J Clin Microbiol 45: 2529-36, 2007; Duarte et al., PloS One 5: pii, e12822, 2010). Further, application of these tests may be limited in their ability to detect and simultaneously identify the specific HCV genotypes (De Keukeleire et al., Int J Infect Dis 15: pii: S1201-9712, 2015). Besides, several (reverse transcription) loop mediated isothermal amplification (RT)-LAMP assays have been designed for detection of various pathogens including HCV, but they detect a limited amount of genotypes and rarely demonstrate genotype identification of the pathogens targeted for detection (Notomi et. al., Nucleic Acids Res 28: E63, 2000; Nagamine K, Hasse T, Notomi, T. 2002. Accelerated reaction by loop-mediated isothermal amplification using loop primers. Mol Cell Probes. 16: 223-29; Blomström et al., J Virol Methods 147: 188-93, 2008; Kargar et al., Indian J Virol 23: 18-23, 2012; Yang J, et al., Arch Virol 156: 1387-96, 2011; Wang et al., FEMS Immunol Med Microbiol 8: 144-47, 2011; Sun et al., B Angew Chem Int Ed Engl 53: 8088-92, 2014).

Several reports have been published regarding RT-LAMP assays that utilized the HCV 5' non-coding region (5'-NCR) for primer design and detection of HCV-RNA (Kargar et al., Indian J Virol 23: 18-23, 2012; Yang J, et al., Arch Virol 156: 1387-96, 2011; Wang et al., FEMS Immunol Med Microbiol 8: 144-47, 2011; Sun et al., B Angew Chem Int Ed Engl 53: 8088-92, 2014). Unfortunately, these works are limited to detection only and demonstrate no pattern formation of the bands, thereby hindering clear determination of true positive detection, contamination, or cross-reactivity. Also, RT-LAMP assays traditionally rely on electrophoretic gel end-point analysis of banding-pattern to determine positive amplification. Therefore, it is important that laddering of RT-LAMP amplicons are arranged in clear and distinct patterns to enable easy analysis and interpretation of amplification results.

This study reports the development of the first RT-LAMP method for detection and simultaneous genotype-identification of HCV genotypes 1-6. The assay is simple, sensitive, and performed on the molecular basis of auto cycling strand-displacement DNA synthesis which produces long stem-loop products of multiple inverted repeats under isothermal amplification (Notomi et. al., *Nucleic Acids Res* 28: E63, 2000; Nagamine K, Hasse T, Notomi, T. 2002. Accelerated reaction by loop-mediated isothermal amplification using loop primers. Mol Cell Probes. 16: 223-29; Blomström et al., *J Virol Methods* 147: 188-93, 2008; Kargar et al., *Indian J Virol* 23: 18-23, 2012). The amplification process is rapid and accomplished in less than 60 minutes, utilizing two thermostable enzymes and 2-3 sets of oligonucleotides. The oligonucleotides target conserved as well as sparsely polymorphic sequences in the 5'-NCR of the HCV genome (Bukh et al., *Proc. Natl. Acad. Sci. USA* 89: 4942-46, 1992) (Table 1), producing distinctly clear banding-pattern that indicate positive detection for possible target identification. In this study, a new approach to HCV detection and genotype-identification is introduced and discussed.

Materials and Methods

Nucleic Acid Standards and Plasma Panels

Quantified Armored RNA standards of HCV 1a, HCV 1b, and HCV2ac, human immunodeficiency virus (HIV) 1B, dengue virus (DENV) 1, and West Nile virus (WNV) were purchased from Asuragen (Austin, Tex., USA). HCV genotyping plasma panels of WHO International Standard were used in the assay development. The panels included HCV Worldwide AccuSet Performance Panel 0810-0173 (SeraCare, Milford, Mass., USA), the Worldwide HCV Performance Panel WWHV303 (SeraCare, USA), and the AcroMetrix HCV Genotyping Panel (Applied Biosystems/Life Technologies, Grand Island, N.Y., USA). Also, Hepatitis B virus (HBV) plasma panel of WHO International Standard (Applied Biosystems/Life Technologies, USA) was used as control in the assay development.

Diagnostic Genotyping Assay

Detection and identification of HCV was performed by loop-mediated reverse-transcription isothermal amplification in a 25 μL total reaction mixture. The mixture comprised of 12.5 μL of 2× Mannitol-Acetate-Buffer (MAB) (Nyan et al., *Clin Infect Dis* 59: 16-23, 2014) 1 μM each of primers FIP and RIP, 0.6 μM each of primers LF and LR, 0.5 μM each of primers F3 and R3, 8 Units of Bst DNA polymerase (New England Biolabs, MA, USA), 5 U of cloned-AMV reverse-transcriptase and 10 U of RNaseOut (Invitrogen, Md., USA). RNA template volume of 5 μL was applied to the reaction. A no-template (water) control was included in all experiments. Positive controls included known genotypes of HCV-RNA standards. HIV, DENV, WNV, hepatitis B virus (HBV) DNA (OptiQuant-AcroMetrix/Life Technologies, Benicia, Calif., USA), and normal human plasma were used as assay negative controls. Reactions were performed at 63.5° C. for 30-60 minutes on a portable digital heat-block, the MyBlock Mini Dry Bath (Benchmark Scientific, Edison, N.J., USA) and terminated by placing reaction tubes on ice.

Results

Detection and Analysis of Products

Total RNA extracts of HCV genotypes 1-6 were subjected to isothermal amplification. Electrophoretic analysis of reaction products demonstrated positive amplification of HCV RNA by primer sets DN1 and DN2. The oligonucleotides produced a ladder-like banding pattern common to HCV genotypes 1-6, while the assay reaction was negative to DENV, WNV, HIV, and HBV as confirmed by the absence of banding pattern (FIG. 1A and Supplementary Figure S1A). For rapid naked-eye visualization of results, GelGreen DNA intercalating dye was added to the reaction tubes which revealed an intense fluorescence glow in tubes with amplified RNA as compared with the no-template control (NTC), DENV, WNV, HIV, and HBV (FIG. 1B and Supplementary Figure S1B).

Specificity and Genotype Identification

The assay specificity and cross-reactivity of the primers were evaluated by amplification and gel electrophoretic analysis. As observed on the gels, the primers detected only HCV RNAs, but reacted negative to nucleic acids of DENV (or D), WNV (or W), HIV, and HBV (FIG. 1A and Supplementary Figure S1). Interestingly, primer set DN3 reacted positive to HCV genotypes 1, 3, 4, 5, and 6, producing banding-pattern of amplicons that were unique to each genotype detected, although weakly positive for HCV-3 (FIG. 1C). Differences in banding-patterns were identified by keen observation of the pattern locations relative to the molecular marker, size of the bands within the patterns, spacing of each group of patterns, and the laddering-shift of the patterns as illustrated by the color lines between the duplicate samples (FIG. 1C). When clinical donor specimens were tested using primer set DN3, the results revealed detection of HCV-1 and HCV-6 (FIG. 2, Supplementary Figure S2, and Supplementary Table S1).

Assay Sensitivity

The assay's sensitivity and LOD were determined by testing serial dilutions of HCV-RNA ($10^5$-0.1 IU/rxn). Results of electrophoretic analysis demonstrated detection of 10 IU/rxn of HCV-RNA (FIG. 3A). Addition of GelGreen fluorescent dye to the reaction-tubes revealed fluorescent glow with decreasing intensity that corresponded to the level of HCV-RNA amplified (FIG. 3B). Probit test of HCV-RNA replicates demonstrated a 100% detection rate for $10^5$, $10^4$, $10^3$, and $10^2$ IU; 80% detection rate for 50 IU; and, 40% detection rate for 10 IU. One (1 IU) and 0.1 IU of HCV-RNA were not detected (Table 2A).

TABLE 2

Probit data: Test of replicates of HCV RNA serial dilutions

| HCV RNA Dilutions (IU) | Number of Replicates Tested | Number of Positive Reactions | Percent Positive (%) |
|---|---|---|---|
| $10^5$ | 6 | 6 | 100 |
| $10^4$ | 5 | 5 | 100 |
| $10^3$ | 5 | 5 | 100 |
| $10^2$ | 5 | 5 | 100 |
| 50 | 5 | 4 | 80 |
| 10 | 5 | 2 | 40 |
| 1.0 | 5 | 0 | 0 |
| 0.1 | 5 | 0 | 0 |

Time-Course of Detection

In order to determine the time point at which amplification of HCV-RNA occurred, 10 and 50 IU of RNA were tested in the isothermal amplification reaction at designated time-points. Results of electrophoretic analysis of reaction products revealed amplification of 10 IU/rxn of RNA at 60 minutes, while amplification of 50 IU/rxn was observed at 40 minutes (FIG. 5).

Detection and Identification of HCV in Clinical Specimens

In order to determine the clinical applicability of the RT-LAMP-genotyping assay, total RNA was extracted from 171 clinical donor specimens and tested using primer set DN3. Of the 71 HCV-positive clinical donor specimens tested, the assay detected a total of 65 HCV-infected specimens. That is, 58 plasma specimens reaction was positive for HCV-1; two plasma specimens tested positive for HCV-6; two of the known HCV-3 serum specimens tested positive; the 3 known HCV-4 plasma specimens also tested positive, while a total of 6 HCV-infected specimens reacted negative. All healthy human plasma specimens (n=100) tested negative (FIG. 2 and Supplementary Figure S2; Table 2B; Supplementary Table S1). As presented in Table 2C, the assay demonstrated a diagnostic sensitivity of 91.5% with a confidence interval (CI) of 82.5% to 96.8%, while the specificity was 100% with a CI of 96.3% to 100%.

TABLE 3

Evaluation of HCV RT-LAMP genotyping assay with donor plasma and serum specimens

| Sample ID | Specimen Type | RT-LAMP- Results | HCV Genotype Identified |
|---|---|---|---|
| 1 | Plasma | Positive | 1 |
| 2 | Plasma | Positive | 1 |
| 3 | Plasma | Positive | 1 |
| 4 | Plasma | Positive | 1 |
| 5 | Plasma | Positive | 1 |
| 6 | Plasma | Positive | 1 |
| 7 | Plasma | Positive | 1 |
| 8 | Plasma | Positive | 1 |
| 9 | Plasma | Positive | 1 |
| 10 | Plasma | Positive | 1 |
| 11 | Plasma | Positive | 1 |
| 12 | Plasma | Positive | 1 |
| 13 | Plasma | Positive | 1 |
| 14 | Plasma | Positive | 1 |
| 15 | Plasma | Positive | 1 |
| 16 | Plasma | Positive | 1 |
| 17 | Plasma | Negative | NA |
| 18 | Plasma | Positive | 1 |
| 19 | Plasma | Positive | 1 |
| 20 | Plasma | Positive | 1 |
| 21 | Plasma | Positive | 1 |
| 22 | Plasma | Positive | 1 |
| 23 | ƒSerum | Positive | 4 |
| 24 | ƒSerum | Positive | 4 |
| 25 | *Plasma | Positive | 3 |
| 26 | *Plasma | Positive | 3 |
| 27 | *Plasma | Negative | NA |
| 28 | ƒSerum | Positive | 4 |
| 29 | Plasma | Positive | 1 |
| 30 | Plasma | Negative | NA |
| 31 | Plasma | Negative | NA |
| 32 | Plasma | Positive | 1 |
| 33 | Plasma | Positive | 1 |
| 34 | Plasma | Positive | 1 |
| 35 | Plasma | Negative | NA |
| 36 | Plasma | Positive | 6 |
| 37 | Plasma | Positive | 1 |
| 38 | Plasma | Positive | 1 |
| 39 | Plasma | Positive | 1 |
| 40 | Plasma | Positive | 1 |
| 41 | Plasma | Positive | 1 |
| 42 | Plasma | Positive | 1 |
| 43 | Plasma | Positive | 1 |
| 44 | Plasma | Positive | 1 |
| 45 | Plasma | Positive | 1 |
| 46 | Plasma | Positive | 1 |
| 47 | Plasma | Positive | 1 |
| 48 | Plasma | Positive | 1 |
| 49 | Plasma | Positive | 1 |
| 50 | Plasma | Positive | 1 |
| 51 | Plasma | Positive | 6 |
| 52 | Plasma | Positive | 1 |
| 53 | Plasma | Positive | 1 |
| 54 | Plasma | Positive | 1 |
| 55 | Plasma | Positive | 1 |
| 56 | Plasma | Positive | 1 |
| 57 | Plasma | Positive | 1 |
| 58 | Plasma | Positive | 1 |
| 59 | Plasma | Positive | 1 |
| 60 | Plasma | Positive | 1 |
| 61 | Plasma | Positive | 1 |
| 62 | Plasma | Positive | 1 |
| 63 | Plasma | Negative | NA |
| 64 | Plasma | Positive | 1 |
| 65 | Plasma | Positive | 1 |
| 66 | Plasma | Positive | 1 |
| 67 | Plasma | Positive | 1 |
| 68 | Plasma | Positive | 1 |
| 69 | Plasma | Positive | 1 |
| 70 | Plasma | Positive | 1 |
| 71 | Plasma | Positive | 1 |
| Total infected specimens tested (n = 71) | Infected specimens detected negative (n = 6) | Infected specimens detected positive (n = 65) | Percent of infected specimens detected (91%) |
| Healthy plasma specimens (n = 100) | Healthy specimens detected negative (n = 100) | Healthy specimens detected positive (n = 0) | Percent of healthy specimens detected negative (100%) |
| Total clinical specimens tested (n = 171) | | | |

Positive detection (+);
*Plasma specimens previously identified to be HCV3-positive;
ƒSerum specimens previously identified to be HCV4-positive;

Detection of HCV RNA with Heat-Treated Plasma Specimens

The assay was also investigated for its ability to amplify viral nucleic acid from heat-treated specimens without RNA extraction. When serial dilutions of heated plasma specimens were tested in the amplification reactions, electrophoretic results demonstrated detection of HCV RNA ($10^6$-$10^4$ IU/rxn) as confirmed by the presence of banding-patterns (Supplementary Figure S3).

Discussion

Hepatitis C virus (HCV) is a major health care problem worldwide. HCV detection and genotypes identification provide an important insight into the clinical progression of liver disease, response to antiviral therapies, and the dynamics of HCV global epidemiological profile. This study has demonstrated the performance of a specific and simple isothermal amplification assay for rapid detection and genotype-identification of HCV infection in plasma and serum. This work describes the first RT-LAMP assay that detects 6 HCV using single primer sets such as DN1 and DN2. This assay demonstrates advantages over labor-intensive methods that require heavy equipment and multiple diagnostic steps for HCV detection and genotype identification (Albertoni et al., *Braz J Infect Dis* 14: 147-52, 2010; Detmer et al., *J. Clin Microbiol* 34: 901-907, 1996; Kotwal et al., *Proc Natl Acad Sci.* 89: 4486-89, USA 1992; Hara et al., *J Clin Microbiol* 51: 1485-89, 2013; Shemis et al., *Hepat Mon* 12: 265-70, 2012) Conducted as a one-step-procedure, this assay also obviates the need for extra cDNA-synthesis and restriction-digest steps for genotype identification. In this assay, both synthesis and amplification of the HCV-RNA were performed in a single reaction-tube, using a single temperature. Additionally, the assay detected and distinguished the HCV-genotypes without requiring post-amplification genotyping procedures such as restriction enzyme analysis, reverse hybridization, or nested RT-PCR (Sun et al., B *Angew Chem Int Ed Engl* 53: 8088-92, 2014; Albertoni et al., *Braz J Infect Dis* 14: 147-52, 2010; Detmer et al., *J Clin Microbiol* 34: 901-907, 1996; Kotwal et al., *Proc Natl Acad Sci.* 89: 4486-89, USA 1992; Hara et al., *J Clin Microbiol* 51: 1485-89, 2013; Shemis et al., *Hepat Mon* 12: 265-70, 2012). Moreover, this assay successfully amplified HCV-RNA utilizing heated specimens without conventional RNA extraction (Supplementary Figure S3). This method of substrate preparation enhances the rapidity of detection and may provide a cost-saving approach for laboratories in resource-limited settings. Notwithstanding its time-saving nature and cost-effectiveness, further improvements in this method of template preparation is required.

The data presented in this study have demonstrated a reverse transcription isothermal amplification assay with the capability to detect HCV infections at the genotypic level. Due to its sensitivity, specificity, and lack of requirements for expensive equipment, this assay is potentially suitable for field and point-of-care use in resource-limited settings and HCV-endemic regions of the world.

Example 3

Real-Time Quantitative Isothermal Multiplex Assay for Pathogen Detection

The subject matter of this example is included in Nyan and Swinson (Nature Scientific Reports; doi:10.1038/srep17925) that is referenced in part.

Introduction

The global emergence or re-emergence of a plethora of bacterial, viral, and parasitic pathogens with outbreaks of virulent infections have challenged the diagnostic capabilities of health care systems globally, mainly in resource-limited environments (Baize et al., *N Engl J Med.* 371: 1418-1425, 2014; Duda et al., *J Int AIDS Soc* 0.17:19045, 2014). This have since underscored the need for simple, but efficient diagnostic tools that would enable rapid detection, quantitation, and simultaneous identification of pathogens, particularly those presenting similar on-set clinical symptoms. Such differential diagnostic tools would enable health care workers to institute the requisite measures including isolation and timely therapeutic interventions. Hepatitis B virus (HBV), Hepatitis C virus (HCV), and the emerging Hepatitis E virus (HEV) together infect over 400 million people globally and may lead to chronic active hepatitis and hepatocellular carcinoma (CDC. *MMWR.* 58 (No. SS-3), 2009; Huy and Vernavong. *AIDS Res Treat.* 2014:581021. doi: 10.1155/2014/581021). Infection with the human immunodeficiency virus (HIV) compromises the immune system, while Dengue virus (DENV), West Nile Virus (WNV), and Chikungunya virus (CHIKV) infections may lead to hemorrhagic fever, neuroinflammatory, and arthritic conditions in infected patients, respectively (Naze. et al. *J Virol Methods.* 162:1-7, 2009; Omarjee. et al. *Euro Surveill.* 19. pii: 20753, 2014). The world has recently witnessed the ravaging effect of the Ebola virus disease outbreak in West Africa. Other pathogens such as Marburg virus (MBV), Yellow fever virus (YFV), Lassa fever virus (LFV), *Plasmodium* species, Chikungunya virus (CHIKV), Japanese Encephalitis virus (JEV), Middle Eastern Respiratory Syndrome Corona virus (MERS CoV), *Mycobacterium* species (MTB), Severe Acute Respiratory Syndrome Corona virus (SARS CoV), Cytomegalovirus (CMV), Parvovirus (PAB19), *Plasmodium* species (PLM), *Leishmania* species (LE), and *Trypanosoma* (TRY) have also caused diseases of untold human sufferings (Feldmann and Geisbert, *The Lancet.* 377:849-862, 2011; Dummer et al., *J. Infect. Dis.* 152, 1182-1191, 1985; Alvar et al., *PLoS One.* 7:e35671, 2012; Zaki et al., *N Engl J Med.* 367:1814-1820, 2012; WHO. Global tuberculosis report 2014, 2014). Hence, the need for a simple and cost-effective assay capable of simultaneously detecting and identifying the presence of multiple bacterial, viral and parasitic pathogens in patients or those circulating in particular endemic regions cannot be overemphasized.

Several amplification-based multiplex test-methods including quantitative reverse-transcription polymerase chain reaction (qRT-PCR) have been developed and used to detect and quantitate pathogen load (Chao et al., *J Clin Microbiol.* 45, 584-589, 2007; Hennechart-Collette et al., *J Appl Microbiol.* 116, 179-190, 2014). However, these methods exhibit drawbacks as they are time-consuming, expensive, and require the use of heavy equipment and highly trained personnel to perform. Despite their outstanding performance, these characteristics present limitations in their point-of-care use in field and resource-limited environments. Besides, many (reverse transcription) loop-mediated isothermal amplification assays (RT)-LAMP have been designed, but have hardly demonstrated multiplexing capability to simultaneously detect different types of viruses (Notomi et al. *Nucleic Acids Res.* 28: e63, 2000; Blomström et al. *J Virol Methods.* 147: 188-193, 2008; Zhang et al. *J Clin Microbiol.* 48: 2116-2121, 2010; Pan et al. *BMC Infect Dis.* DOI: 10.1186/1471-2334-12-254, 2012). Those (RT)-LAMP methods that claim multiplexing capability are restricted to detecting only one type of pathogen (e.g. viruses—Influenza A), rely on an opened-tube analysis of amplification products for detection and quantitation, and utilize on gel-end point analysis for distinction of viruses, and based on non-specific fluorescene chemistries such as SYBR Green, GelGreen, calcein or hydroxy naphthol blue that are target-independent (Jung et al., *Analytica Chimica Acta.* 853, 541-547, 2015; Tomita et al., *Nat. Prot.* 3, 877-882, 2008; Beauchamp et al., *Anal. Methods.* 4, 4187-4192, 2012; Wang et al., *Virology Journal* 8, 108, 2011).

The method herein reported describes the development of the first real-time quantitative multiplex fluoro-isothermal amplification assay for detection and identification of bacterial, viral and parasitic pathogens, as well as simultaneous quantification of pathogen burden in biological samples (e.g. blood plasma and serum). The method utilizes 2 to 3 pairs of pathogen-specific oligonucleotides including fluorogenic oligonucleotides that produces real time nucleic acid amplification results of graphs representing different pathogens or different genotypes/species of a particular pathogen. This also enables instant visualization of different colors for different pathogens as well as detection and quantitation.

This assay is based on fluorogenic auto cycling strand-displacement DNA synthesis (Walker et al. *Nucleic Acids Res.* 20: 1691-1696, 1992; Notomi et al. *Nucleic Acids Res.* 28: e63, 2000; Marras. *Mol Biotechnology.* 3 8: 247-255, 2008). Specially developed pathogen-specific flourophores and oligonucleotides simultaneously hybridize to the target nucleic acids in a sample and emit distinctive detection signals. The amplification process is accomplished within about 10 to 40 minutes, utilizing a portable real-time multichannel fluorospectrophotometric heat source or device. Here, a novel approach at multiple pathogen detection, identification, and quantitation by isothermal real time amplification is reported. This new detection method could be useful in alleviating differential diagnostic challenges in resource-limited environments of the developing as well as developed world settings clinical and point-of-care settings.

Experimental Methods

Preparation of Samples for Amplification

DNA and total RNA are extracted from standard reference and genotyping plasma panels of WHO International Standard (OptiQuant-AcroMetrix/Life Technology, Benicia, Calif., USA and Sera Care, Milford, Mass., USA, respectively). Nucleic acids are also extracted from clinical donor plasma specimens using the QiaAmp Viral RNA mini kit and the QiAamp DNA Blood Mini Kit modified protocol (Qiagen, Germantown, Md., USA) as previously described (Nyan et al. *Clin Infect Dis.* 59:16-23, 2014). Second, clinical specimens are also subjected to lysis utilizing the New Lysis Buffer, making samples directly available for amplification without further extraction procedure. Third, samples are directly applied in the reaction mixture which enables lysis and simultaneous amplification of nucleic acid due to the lytic effect of the novel reaction buffer.

Design of Oligonucleotides

Several full-length sequences of pathogens including bacteria, viruses, and protozoans pathogens were obtained from the EMLB and GenBank databases and analyzed using CLUSTALW-2 and CLUSTAL-Omega. Pathogen-specific Forward outer primer (F3), Reverse outer primer (R3), Forward Inner primer (FIP), Reverse Inner primer (RIP), Loop Forward primer (LF), and Loop Reverse primer (LR) were manually designed. Further, the F3, R3, LF, or LR primers were designed as bi-labeled loop fluorescent probes. The loops are held in a hairpin-loop conformation by 5 to 7 nucleotides long complementary stem-sequences at both ends (5'-3' or vice versa) and tagged with desirable reporter-fluorophore or quencher. Fluorophores include 6-carboxyfluorescein (6-Fam), tetrachlorofluorescein (Tet), or Texas-Red or other desirable reporter dyes, while quenchers include black hole quencher-1, 2, and 3 (BHQ1, 2, and 3) or other desirable quenchers.

Standards and Controls

Quantitated HIV, HCV, and HBV plasma panels of WHO International Standards, (OptiQuant-AcroMetrix/Life Technology, and Sera Care, USA) are subjected to nucleic extraction. Armored RNA standards of Dengue and West Nile viruses (Asuragen, Tex., USA) are also used as standard controls. DNA and RNA were serially diluted in nuclease-free water, and used in amplification reactions.

Multiplex Amplification Assay

Nucleic acid detection, identification, and quantitation of the various targeted pathogens is performed by real-time (reverse-transcription)-isothermal amplification process in a 25 µL reaction mixture. The mixture comprises of about 10 to 12.5 µL of Lysis Reaction Buffer (LRB) and a mixed pathogen-specific oligonucleotide sets including pathogen-specific hair-pin loop fluorooligonucleotides (about 0.1 to 1 µM) of the target bacteria, viruses, and/or parasites. About Five (5) units of RnaseOut, 5 U of cloned AMV reverse-transcriptase (Invitrogen, Frederick, USA), and 8-10 Units of Bst DNA polymerase (New England Biolabs, MA, USA), are added to catalyze the reaction. Sample subjected to heat-treatment, lysis buffer treatment or nucleic acid extraction (e.g. EBOV, MERS CoV, HIV, HCV, HBV, TRY, DENV, MTB, WNV, PLM, ZKV, and CHIKV) is applied to the mixture as template volume of 1-10 µL. An assay internal positive control of approximately $100\text{-}10^6$ IU per reaction (or equivalent copies per reaction) and no-template (water) control is included in all amplification runs to control for assay efficiency and reagent integrity. Normal human plasma also serves as negative control. Amplification-reactions are conducted at about 60° C. for about 20-40 minutes on a portable real-time (multichannel) fluorospectrophotometric heating device.

Analysis of Results and Quantitation Nucleic Acid

During the process of amplification, results are read on the real-time (multichannel) fluorospectrophotometric heating device. The device reveals simple graphs at different wavelengths (e.g. 400 to 740 nm) having amplitudes that represent fluorescent emission of amplified nucleic acids of a specific pathogen (see illustration in FIG. 9: HIV, HBV, WNV, and HCV; and FIG. 10: HIV, HBV, WNV, PLM, CMV, DENV, TRY, and LE). The quantity of the amplified nucleic acid is calculated by the device against the negative control and a predetermined internal control. Naked eye UV and/or blue-light visualization of reaction tubes reveals fluorescence glow only in reaction tubes with amplified nucleic acid of the pathogens of interest (see FIGS. 8B and 8D). This is applicable to detecting and identifying multiple pathogens of interest.

Specificity and Sensitivity

Assay sensitivity was evaluated by testing 10-fold serial dilutions of quantitated HBV-DNA and HCV-RNA, with results demonstrating detection of approximately 10 IU/reaction of nucleic acid, while the assay has demonstrated a high specificity. Evaluation of the assay diagnostic sensitivity with clinical human plasma specimens (including HIV, WNV, DENV, HBV, and HCV) detection of 36 of 37 (97%) infected specimens when the respective fluorooligonucleotides of HIV, WNV, DENV, HBV, and HCV were used (see table 4). The assay diagnostic specificity was tested using control plasma (n=52) using normal human plasma, plasma infected with Cytomegalovirus and parvovirus against pathogen-specific primers and fluorooligonucleotides of HIV, WNV, DENV, HBV, and HCV, respectively. The results revealed a 100% diagnostic specificity as demonstrated by no detection of negative control samples (see Table 4).

TABLE 3

Clinical donor specimens tested by Isothermal Multiplex Assay

| Specimens | Number Tested | Isothermal Multiplex Assay | ¶Procleix test |
|---|---|---|---|
| A. Negative Clinical specimens (n = 52) | | Diagnostic Specificity (Test-Negative) | |
| Normal Human Plasma | 28 | 28 | 28 |
| Cytomegalovirus | 15 | 15 | 15 |
| Parvovirus | 9 | 9 | 9 |
| Total | 52 | 52 | 52 |
| Percent Negative | | 100% | 100% |
| B. Positive Clinical Specimens (n = 37) | | Diagnostic Sensitivity (Test-Positive) | |
| Human immunodeficiency virus | 6 | 5 | 6 |
| Hepatitis B virus | 9 | 9 | 9 |
| Hepatitis C virus | 10 | 10 | 10 |
| Dengue virus | 5 | 5 | 5 |
| West Nile virus | 7 | 7 | 7 |
| Total | 37 | 36 | 37 |
| Percent Positive | | 97% | 100% |

¶Procleix data based on selected cohort;
Abbreviation: NA, not applicable

The data demonstrate the potential application of this method for detection, identification, and quantification of multiple bacterial, viral and parasitic targets. The assay revealed a high diagnostic sensitivity and specificity (see Table 4). The summation of these results suggest that this assay could be employed for analysis of patients' blood samples, donor screening for blood-borne pathogens, and investigating the epidemiological trend of infectious pathogens in endemic regions.

It should be recognized that the above described embodiments to which the principles of the disclosure applies are possible examples of illustrative implementation, set forth to provide a clear understanding of this disclosure, and should not be considered as limiting the scope of the invention. Many other variations and further modifications are intended to be made to the above described embodiments without departing from the scope of this invention, rather intended to be included within the scope of this disclosure as well as defined and protected by the following claims.

We claim:

1. A method of isothermal detection of a plurality of pathogens, the method comprising:
   providing a sample;
   extracting nucleic acid from the sample;
   mixing the sample with amplification or detection reagents;
   placing the sample mixture on a thermal heating device for a predetermined period of time;
   amplifying the extracted nucleic acid; and
   detecting at least two pathogens in real time from the extracted nucleic acid,
   wherein the step of detecting further comprises:
   contacting the sample with two or more sets of real time loop-mediated isothermal amplification (LAMP) primers and probes, each primer and probe comprising a nucleic acid sequence having at least 90 to 99% sequence identity to any one of SEQ ID NOs 1-306, wherein the sets are selected from the group consisting of (a) sets of (RT)-LAMP primers specific for HCV nucleic acid comprising four to six primers consisting of the nucleic acid sequences of SEQ ID NOs 1-68;
   (b) sets of (RT)-LAMP primers specific for HBV nucleic acid comprising four to six primers consisting of the nucleic acid sequences of SEQ ID NOs 69-86;
   (c) sets of (RT)-LAMP primers specific for HEV nucleic acid comprising four to six primers consisting of the nucleic acid sequences of SEQ ID NOs 87-100;

(d) sets of (RT)-LAMP primers specific for HIV nucleic acid comprising four to six primers consisting of the nucleic acid sequences of SEQ ID NOs 101-112;
(e) sets of (RT)-LAMP primers specific for WNV nucleic acid comprising four to six primers consisting of the nucleic acid sequences of SEQ ID NOs 113-118;
(f) sets of (RT)-LAMP primers specific for DENV nucleic acid comprising four to six primers consisting of the nucleic acid sequences of SEQ ID NOs 119-130;
(g) sets of (RT)-LAMP primers specific for CHIKV nucleic acid comprising four to six primers consisting of the nucleic acid sequences of SEQ ID NOs 131-143;
(h) sets of (RT)-LAMP primers specific for CMV nucleic acid comprising four to six primers consisting of the nucleic acid sequences of SEQ ID NOs 144-150;
(i) sets of (RT)-LAMP primers specific for PLM nucleic acid comprising four to six primers consisting of the nucleic acid sequences of SEQ ID NOs 151-156;
(j) sets of (RT)-LAMP primers specific for EBOV nucleic acid comprising four to six primers consisting of the nucleic acid sequences of SEQ ID NOs 157-169;
(k) sets of (RT)-LAMP primers specific for MARV nucleic acid comprising four to six primers consisting of the nucleic acid sequences of SEQ ID NOs 170-175;
(l) sets of (RT)-LAMP primers specific for YFV nucleic acid comprising four to six primers consisting of the nucleic acid sequences of SEQ ID NOs 176-181;
(m) sets of (RT)-LAMP primers specific for LE nucleic acid comprising four to six primers consisting of the nucleic acid sequences of SEQ ID NOs 182-187;
(n) sets of (RT)-LAMP primers specific for LFV nucleic acid comprising four to six primers consisting of the nucleic acid sequences of SEQ ID NOs 188-209;
(o) sets of (RT)-LAMP primers specific for MTB nucleic acid comprising four to six primers consisting of the nucleic acid sequences of SEQ ID NOs 210-221;
(p) sets of (RT)-LAMP primers specific for MERS CoV nucleic acid comprising four to six primers consisting of the nucleic acid sequences of SEQ ID NOs 222-235;
(q) sets of (RT)-LAMP primers specific for PAB19 nucleic acid comprising four to six primers consisting of the nucleic acid sequences of SEQ ID NOs 236-246;
(r) sets of (RT)-LAMP primers specific for JEV nucleic acid comprising four to six primers consisting of the nucleic acid sequences of SEQ ID NOs 247-258;
(s) sets of (RT)-LAMP primers specific for SARS CoV nucleic acid comprising four to six primers consisting of the nucleic acid sequences of SEQ ID NOs 259-276;
(t) sets of (RT)-LAMP primers specific for TRY nucleic acid comprising four to six primers consisting of the nucleic acid sequences of SEQ ID NOs 277-294; and
(u) sets of (RT)-LAMP primers specific for ZKV nucleic acid comprising four to six primers consisting of the nucleic acid sequences of SEQ ID NOs 295-306.

2. The method of claim 1, wherein the samples contain pathogens comprising at least two or more bacteria, viruses, and/or protozoans for example Chikunguya virus (CHIKV) nucleic acid, Cytomegalovirus (CMV) nucleic acid, Dengue virus (DENV) nucleic, Ebola virus (EBOV) nucleic acid, Hepatitis B virus (HBV) nucleic acid, Hepatitis C virus (HCV) nucleic acid, Human immunodeficiency virus (HIV) nucleic acid, Hepatitis E virus (HEV) nucleic acid, Japanese Encephalitis virus (JEV), *Leishmania* (LE) nucleic acid, Lassa fever virus (LFV) nucleic acid, Marburg virus (MARV) nucleic acid, Middle Eastern Respiratory Syndrome Corona virus (MERS CoV) nucleic acid, Parvovirus (PAB19) nucleic acid, *Plasmodium* (PLM) nucleic acid, Severe Acute Respiratory Syndrome Corona virus (SARS CoV) nucleic acid, *Trypanosoma* (TRY) nucleic acid, West Nile virus (WNV) nucleic acid, Yellow fever virus (YFV) nucleic acid and/or Zika virus (ZKV) nucleic acid.

3. The method of claim 1, wherein the predetermined period of amplification reaction time comprises a range of about 10 to 40 minutes.

4. The method of claim 1, wherein the SEQ ID Nos 1-306 comprise at least one of the following: CHIKV nucleic acid, CMV nucleic acid, DENV nucleic, EBOV nucleic acid, HBV nucleic acid, HCV nucleic acid, HIV nucleic acid, HEV nucleic acid, JEV nucleic acid, LE nucleic acid, LFV nucleic acid, MARV nucleic acid, MERS CoV nucleic acid, PAB19 nucleic acid, PLM nucleic acid, SARS CoV nucleic acid, TRY nucleic acid, a WNV nucleic acid, YFV nucleic acid and/or ZKV nucleic acid.

5. The method of claim 1, wherein the step of extracting the nucleic acid from the sample comprises heating the sample at a temperature of about 30° C. to about 110° C.

6. The method of claim 1, wherein the step of extracting the nucleic acid from the sample comprises applying a lysis buffer to the sample in ratios of about 1:3 to about 1:100 and incubated for about 2 to about 10 minutes.

7. The method of claim 1, wherein the sample comprises blood, plasma, serum, urine, saliva, sperm, vaginal fluid, tissue biopsy, vomitus, fine needle aspirate, cerebrospinal fluid, bronchial aspirate, perspiration, mucus, fecal matter, synovial fluid, swabs, lymphatic fluid, tears, tracheal aspirate and/or a surgical specimen.

8. The method of claim 1, further comprising: contacting the samples with a reverse transcriptase, DNA polymerase, deoxynucleotide, and RNAse inhibitor.

9. The method of claim 1, wherein the method comprises contacting the sample with:
(a) sets of (RT)-LAMP primers specific for HCV nucleic acid comprising four to six primers consisting of the nucleic acid sequences of SEQ ID NOs 1-68;
(b) sets of (RT)-LAMP primers specific for HBV nucleic acid comprising four to six primers consisting of the nucleic acid sequences of SEQ ID NOs 69-86;
(c) sets of (RT)-LAMP primers specific for HEV nucleic acid comprising four to six primers consisting of the nucleic acid sequences of SEQ ID NOs 87-100;
(d) sets of (RT)-LAMP primers specific for HIV nucleic acid comprising four to six primers consisting of the nucleic acid sequences of SEQ ID NOs 101-112;
(e) sets of (RT)-LAMP primers specific for WNV nucleic acid comprising four to six primers consisting of the nucleic acid sequences of SEQ ID NOs 113-118;
(f) sets of (RT)-LAMP primers specific for DENV nucleic acid comprising four to six primers consisting of the nucleic acid sequences of SEQ ID NOs 119-130;

(g) sets of (RT)-LAMP primers specific for CHIKV nucleic acid comprising four to six primers consisting of the nucleic acid sequences of SEQ ID NOs 131-143;
(h) sets of (RT)-LAMP primers specific for CMV nucleic acid comprising four to six primers consisting of the nucleic acid sequences of SEQ ID NOs 144-150;
(i) sets of (RT)-LAMP primers specific for PLM nucleic acid comprising four to six primers consisting of the nucleic acid sequences of SEQ ID NOs 151-156;
(j) sets of (RT)-LAMP primers specific for EBOV nucleic acid comprising four to six primers consisting of the nucleic acid sequences of SEQ ID NOs 157-169;
(k) sets of (RT)-LAMP primers specific for MARV nucleic acid comprising four to six primers consisting of the nucleic acid sequences of SEQ ID NOs 170-175;
(l) sets of (RT)-LAMP primers specific for YFV nucleic acid comprising four to six primers consisting of the nucleic acid sequences of SEQ ID NOs 176-181;
(m) sets of (RT)-LAMP primers specific for LE nucleic acid comprising four to six primers consisting of the nucleic acid sequences of SEQ ID NOs 182-187;
(n) sets of (RT)-LAMP primers specific for LFV nucleic acid comprising four to six primers consisting of the nucleic acid sequences of SEQ ID NOs 188-209;
(o) sets of (RT)-LAMP primers specific for MTB nucleic acid comprising four to six primers consisting of the nucleic acid sequences of SEQ ID NOs 210-221;
(p) sets of (RT)-LAMP primers specific for MERS CoV nucleic acid comprising four to six primers consisting of the nucleic acid sequences of SEQ ID NOs 222-235;
(q) sets of (RT)-LAMP primers specific for PAB19 nucleic acid comprising four to six primers consisting of the nucleic acid sequences of SEQ ID NOs 236-246;
(r) sets of (RT)-LAMP primers specific for JEV nucleic acid comprising four to six primers consisting of the nucleic acid sequences of SEQ ID NOs 247-258;
(s) sets of (RT)-LAMP primers specific for SARS CoV nucleic acid comprising four to six primers consisting of the nucleic acid sequences of SEQ ID NOs 259-276;
(t) sets of (RT)-LAMP primers specific for TRY nucleic acid comprising four to six primers consisting of the nucleic acid sequences of SEQ ID NOs 277-294; and
(u) sets of (RT)-LAMP primers specific for ZKV nucleic acid comprising four to six primers consisting of the nucleic acid sequences of SEQ ID NOs 295-306.

10. The method claim 1, wherein the sample is contacted with the two or more sets of (RT)-LAMP primers and probes consisting of the nucleic acid of SEQ ID No 1-306 for real time multiplex isothermal amplification of the nucleic acids of two or more of the pathogens in a sample including human immunodeficiency virus (HIV), Ebola virus species (Zaire, Sudan, Tai-Forest, Reston, Bundibugyo), Marburg virus (MBV), Yellow fever virus (YFV), hepatitis-B virus (HBV), Lassa fever virus (LFV), hepatitis-C virus (HCV), hepatitis-E virus (HEV), dengue virus (DENV), Chikungunya virus (CHIKV), Japanese Encephalitis virus (JEV), Middle Eastern Respiratory Syndrome Corona virus (MERS CoV), *Mycobacterium* species (MTB), Severe Acute Respiratory Syndrome Corona virus (SARS CoV), West Nile (WNV) virus, Cytomegalovirus (CMV), Parvovirus (PAB19), *Plasmodium* species (PLM), *Leishmania* species (LE), *Trypanosoma* species (TRY) and Zika virus (ZKV) nucleic acids.

11. The method of claim 1, wherein the sample is contacted with the two or more sets of (RT)-LAMP primers and probes consisting of the nucleic acid of SEQ ID No 1-306 in a single reaction vessel for real time multiplex isothermal amplification of the nucleic acids of two or more of the pathogens in a sample at temperature of about 40° C. to about 75° C.

12. The method of claim 1 for rapid real-time multiplex isothermal detection, identification and quantitation of the presence of two or more of the nucleic acid of SEQ ID No 1-306 of pathogens simultaneously or in parallel in a single reaction vessel in real-time on a portable real-time multichannel fluorospectrophotometric heating device.

13. The method of claim 1 wherein samples are contacted with the two or more sets of primers and probes comprising nucleic acid sequence having at least 95-99% sequence identity to any one of SEQ ID NOs 1-306 specific for pathogen including EBOV, MARV, HCV, HBV, HIV, LE, PLM, TRY, LFV, MTB, MERS CoV, SARS CoV, CMV, PAB19, DENV, WNV, JEV, YFV, HEV, CHIKV, and ZKV nucleic acid, amplification of the EBOV, MARV, HCV, HBV, HIV, LE, PLM, TRY, LFV, MTB, MERS CoV, SARS CoV, CMV, PAB19, DENV, WNV, JEV, YFV, HEV, CHIKV, and ZKV nucleic acid, thereby producing EBOV, MARV, HCV, HBV, HIV, LE, PLM, TRY, LFV, MTB, MERS CoV, SARS CoV, CMV, PAB19, DENV, WNV, JEV, YFV, HEV, CHIKV, ZKV pathogen-specific amplification signals as dots, amplification, dissociation, and/or melt curves, thereby detecting the presence of EBOV, MARV, HCV, HBV, HIV, LE, PLM, TRY, LFV, MTB, MERS CoV, SARS CoV, CMV, PAB19, DENV, WNV, JEV, YFV, HEV, CHIKV, and ZKV nucleic acid in the sample, measurable in real-time on a portable real-time multichannel fluorospectrophotometric heating device.

14. The method of claim 1, wherein the two or more sets of (RT)-LAMP primers and probes comprise one or more primers and probes comprising a nucleic acid sequence having at least 95-99% sequence identity to any one of SEQ ID NOs 1-306, wherein at least one primer in the pathogen-specific set of the (RT)-LAMP primers comprises a detectable label that comprises a reporter-fluorophore and fluorescence quencher.

15. A kit for performing the method according to claim 1, wherein the kit comprises two or more sets of real time loop-mediated isothermal amplification (LAMP) primers and probes, each primer and probe comprising a nucleic acid sequence having at least 90 to 99% sequence identity to any one of SEQ ID NOs 1-306, wherein the sets are selected from the group consisting of
(a) sets of (RT)-LAMP primers specific for HCV nucleic acid comprising four to six primers consisting of the nucleic acid sequences of SEQ ID NOs 1-68;
(b) sets of (RT)-LAMP primers specific for HBV nucleic acid comprising four to six primers consisting of the nucleic acid sequences of SEQ ID NOs 69-86;
(c) sets of (RT)-LAMP primers specific for HEV nucleic acid comprising four to six primers consisting of the nucleic acid sequences of SEQ ID NOs 87-100;
(d) sets of (RT)-LAMP primers specific for HIV nucleic acid comprising four to six primers consisting of the nucleic acid sequences of SEQ ID NOs 101-112;
(e) sets of (RT)-LAMP primers specific for WNV nucleic acid comprising four to six primers consisting of the nucleic acid sequences of SEQ ID NOs 113-118;
(f) sets of (RT)-LAMP primers specific for DENV nucleic acid comprising four to six primers consisting of the nucleic acid sequences of SEQ ID NOs 119-130;
(g) sets of (RT)-LAMP primers specific for CHIKV nucleic acid comprising four to six primers consisting of the nucleic acid sequences of SEQ ID NOs 131-143;

(h) sets of (RT)-LAMP primers specific for CMV nucleic acid comprising four to six primers consisting of the nucleic acid sequences of SEQ ID NOs 144-150;
(i) sets of (RT)-LAMP primers specific for PLM nucleic acid comprising four to six primers consisting of the nucleic acid sequences of SEQ ID NOs 151-156;
(j) sets of (RT)-LAMP primers specific for EBOV nucleic acid comprising four to six primers consisting of the nucleic acid sequences of SEQ ID NOs 157-169;
(k) sets of (RT)-LAMP primers specific for MARV nucleic acid comprising four to six primers consisting of the nucleic acid sequences of SEQ ID NOs 170-175;
(l) sets of (RT)-LAMP primers specific for YFV nucleic acid comprising four to six primers consisting of the nucleic acid sequences of SEQ ID NOs 176-181;
(m) sets of (RT)-LAMP primers specific for LE nucleic acid comprising four to six primers consisting of the nucleic acid sequences of SEQ ID NOs 182-187;
(n) sets of (RT)-LAMP primers specific for LFV nucleic acid comprising four to six primers consisting of the nucleic acid sequences of SEQ ID NOs 188-209;
(o) sets of (RT)-LAMP primers specific for MTB nucleic acid comprising four to six primers consisting of the nucleic acid sequences of SEQ ID NOs 210-221;
(p) sets of (RT)-LAMP primers specific for MERS CoV nucleic acid comprising four to six primers consisting of the nucleic acid sequences of SEQ ID NOs 222-235;
(q) sets of (RT)-LAMP primers specific for PAB19 nucleic acid comprising four to six primers consisting of the nucleic acid sequences of SEQ ID NOs 236-246;
(r) sets of (RT)-LAMP primers specific for JEV nucleic acid comprising four to six primers consisting of the nucleic acid sequences of SEQ ID NOs 247-258;
(s) sets of (RT)-LAMP primers specific for SARS CoV nucleic acid comprising four to six primers consisting of the nucleic acid sequences of SEQ ID NOs 259-276;
(t) sets of (RT)-LAMP primers specific for TRY nucleic acid comprising four to six primers consisting of the nucleic acid sequences of SEQ ID NOs 277-294; and
(u) sets of (RT)-LAMP primers specific for ZKV nucleic acid comprising four to six primers consisting of the nucleic acid sequences of SEQ ID NOs 295-306.

* * * * *